(12) United States Patent
Hopkins et al.

(10) Patent No.: US 10,196,392 B2
(45) Date of Patent: Feb. 5, 2019

(54) FUSED HETEROCYCLIC COMPOUNDS AS SELECTIVE BMP INHIBITORS

(71) Applicant: Vanderbilt University, Nashville, TN (US)

(72) Inventors: Corey R. Hopkins, Nolensville, TN (US); Charles C. Hong, Nolensville, TN (US); Craig W. Lindsley, Brentwood, TN (US); Darren W. Engers, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/652,100

(22) Filed: Jul. 17, 2017

(65) Prior Publication Data

US 2017/0313701 A1 Nov. 2, 2017

Related U.S. Application Data

(62) Division of application No. 14/432,472, filed as application No. PCT/US2013/032588 on Mar. 15, 2013, now Pat. No. 9,738,636.

(60) Provisional application No. 61/707,661, filed on Sep. 28, 2012.

(51) Int. Cl.
| | |
|---|---|
| *A61K 31/4709* | (2006.01) |
| *A61K 31/5025* | (2006.01) |
| *A61K 31/519* | (2006.01) |
| *C07D 471/04* | (2006.01) |
| *C07D 487/04* | (2006.01) |
| *C07D 519/00* | (2006.01) |

(52) U.S. Cl.
CPC ........ *C07D 471/04* (2013.01); *A61K 31/4709* (2013.01); *A61K 31/5025* (2013.01); *A61K 31/519* (2013.01); *C07D 487/04* (2013.01); *C07D 519/00* (2013.01)

(58) Field of Classification Search
None
See application file for complete search history.

(56) References Cited

U.S. PATENT DOCUMENTS

| 4,810,705 A | 3/1989 | Bourguignon et al. |
| 2010/0120761 A1 | 5/2010 | Berdini et al. |
| 2010/0210641 A1 | 8/2010 | Shaw et al. |
| 2011/0098471 A1 | 4/2011 | Katoh et al. |
| 2013/0029964 A1 | 1/2013 | Kazumasa et al. |

FOREIGN PATENT DOCUMENTS

| CN | 101679408 A | 3/2010 |
| CN | 101827844 A | 9/2010 |
| EP | 1503757 A2 | 2/2005 |
| EP | 2212323 B1 | 8/2012 |
| JP | 47-047396 | 11/1972 |
| JP | 60-224691 | 3/1989 |
| JP | 2003-514907 | 5/2001 |
| JP | 2004-522777 | 8/2002 |
| JP | 2005-530745 | 11/2003 |
| JP | 2008531574 | 8/2006 |
| JP | 2010-513448 | 7/2008 |
| JP | 2010-520245 | 9/2008 |
| JP | 2010-522765 | 10/2008 |
| JP | 2010-523576 | 10/2008 |
| JP | 2010-531875 | 12/2008 |
| JP | 2010-534633 | 1/2009 |
| JP | 2011-522866 | 12/2009 |
| JP | 2012-521354 | 9/2010 |
| WO | 2001/038326 A2 | 5/2001 |
| WO | WO 2001/38326 | 5/2001 |
| WO | WO 2002/066480 | 8/2002 |
| WO | 2013/092595 A2 | 11/2003 |
| WO | WO 2003/092595 | 11/2003 |
| WO | 2006/091671 A2 | 8/2006 |
| WO | WO 2006/091671 | 8/2006 |
| WO | WO 2008/045393 | 4/2008 |
| WO | 2008/078091 A1 | 7/2008 |
| WO | 2008/078100 A2 | 7/2008 |
| WO | WO 2008/078100 | 7/2008 |
| WO | WO 2008/107125 | 9/2008 |
| WO | WO 2008/121687 | 10/2008 |
| WO | WO 2008/124323 | 10/2008 |
| WO | WO 2009/002534 | 12/2008 |
| WO | 2009/013335 A1 | 1/2009 |
| WO | WO 2009/013335 | 1/2009 |
| WO | 2009/050183 A2 | 4/2009 |
| WO | 2009/114180 A1 | 9/2009 |

(Continued)

OTHER PUBLICATIONS

Squires, et al.,; Potent, Selective Inhibitors of Fibroblast Growth Factor Receptor Define Fibroblast Growth Factor Dependence in Preclinical Cancer Models; Molecular Cancer Therapeutics; 2011; 10(9); pp. 1542-1552.

Chen, et al., Developing and applying a gene functional association network for anti-angiogenic kinase inhibitor activity assessment in an angiogenesis co-culture model; BMC Genomics; 2008; vol. 9; pp. 1-16.

Yurugi, et al.; Studies on the Syntheses of N-Heterocyclic compounds XIV syntheses of 7-Phenyl-s-triazolo(4,3-a} pyridine derivatives; Yakugaku Zasshi; 1973; 93(5); pp. 642-647.

Wu, et al., Design and synthesis of 3,7-diarylimidazopyridines as inhibitors of the VEGF-receptor KDR, Bioorganic & Medicinal Chemistry Letters 14 (2004) 909-912.

Aiguade, et al., Novel triazolopyridylbenzamides as potent and selective p38a inhibitors, Bioorganic & Medicinal Chemistry Letters 22 (2012) 3431-3436.

(Continued)

*Primary Examiner* — Samantha L Shterengarts
(74) *Attorney, Agent, or Firm* — Stites & Harbison PLLC; Richard S. Myers, Jr.

(57) ABSTRACT

The present invention provides small molecule inhibitors of BMP signaling. These compounds may be used to modulate cell growth, differentiation, proliferation, and apoptosis, and thus may be useful for treating diseases or conditions associated with BMP signaling, including inflammation, cardiovascular disease, hematological disease, cancer, and bone disorders, as well as for modulating cellular differentiation and/or proliferation.

15 Claims, No Drawings

(56) References Cited

FOREIGN PATENT DOCUMENTS

| WO | 2009/157423 | 12/2009 |
| WO | 2009150240 | 12/2009 |
| WO | 2010/083145 | 7/2010 |
| WO | 2010/108074 | 9/2010 |
| WO | 2010/119285 | 10/2010 |
| WO | 2011/136264 A1 | 11/2011 |
| WO | WO 2011/136264 | 11/2011 |
| WO | 2012/088266 | 6/2012 |
| WO | 2013/016452 A2 | 1/2013 |
| WO | 2014/138088 A1 | 9/2014 |
| WO | 2014/160203 A2 | 10/2014 |

OTHER PUBLICATIONS

Cross, E. E. et al., 'Application of small organic molecules reveals cooperative TGF β and BMP regulation of mesothelial cell behaviors', ACS Chemical Biology, 2011, vol. 6, pp. 952-961.

Hong, C. C. et al., 'Applications of small molecule BMP inhibitors in physiology and disease', Cytokine & Growth Factor Reviews, 2009, vol. 20, pp. 409-418.

Hao, J. et al., 'In vivo structure-activity relationship study of dorsomorphin analogues identifies selective VEGF and BMP inhibitors', ACS Chemical Biology, 2010, vol. 5, No. 2, pp. 245-253.

Wu Zhicai et al: "Design and synthesis of 1-5 3.7-diarylimidazopyridines as inhibitors of the VEGF-receptor KDR". Bioorganic & Medicinal Chemistry Letters. Pergamon. Amsterdam. NL. vo 1 • 14. No. 4. Feb. 23, 2004 (Feb. 23, 2004). pp. 909-912.

Pigeon et al. J. Biol. Chem. 276:7811-7819, 2001.

Fraenkel et al. J. Clin. Invest. 115:1532-1541, 2005.

Nicolas et al. Proc. Natl. Acad. Sci. U.S.A. 99:4596-4601, 2002.

Nicolas et al. Nat. Genet. 34:97-101, 2003.

Nemeth et al. Science 306:2090-2093, 2004.

FUSED HETEROCYCLIC COMPOUNDS AS SELECTIVE BMP INHIBITORS

RELATED APPLICATIONS

This application is a Divisional Application of U.S. patent application Ser. No. 14/432,472, filed Mar. 30, 2015, which is the U.S. National Stage of International Patent Application No. PCT/US2013/032588, filed Mar. 15, 2013, which claims the benefit of priority to U.S. Patent Application No. 61/707,661, filed Sep. 28, 2012, the entire contents of each of which are expressly incorporated herein by reference in their entirety.

BACKGROUND OF THE INVENTION

Signaling involving the Transforming Growth Factor (3 (TGF-β) superfamily of ligands is central to a wide range of cellular processes, including cell growth, differentiation, and apoptosis. TGF-β signaling involves binding of a TGF-β ligand to a type II receptor (a serine/threonine kinase), which recruits and phosphorylates a type I receptor. The type I receptor then phosphorylates a receptor-regulated SMAD (R-SMAD; e.g., SMAD1, SMAD2, SMAD3, SMAD5, SMAD8 or SMAD9), which binds to SMAD4, and the SMAD complex then enters the nucleus where it plays a role in transcriptional regulation. The TGF superfamily of ligands includes two major branches, characterized by TGF-β/activin/nodal and Bone Morphogenetic Proteins (BMPs).

Signals mediated by bone morphogenetic protein (BMP) ligands serve diverse roles throughout the life of vertebrates. During embryogenesis, the dorsoventral axis is established by BMP signaling gradients formed by the coordinated expression of ligands, receptors, co-receptors, and soluble antagonists (Massague et al. Nat. Rev. Mol. Cell. Biol. 1:169-178, 2000). Excess BMP signaling causes ventralization, an expansion of ventral at the expense of dorsal structures, while diminished BMP signaling causes dorsalization, an expansion of dorsal at the expense of ventral structures (Nguyen et al. Dev. Biol. 199: 93-110, 1998; Furthauer et al. Dev. Biol. 214:181-196, 1999; Mintzer et al. Development 128:859-869, 2001; Schmid et al. Development 127:957-967, 2000). BMPs are key regulators of gastrulation, mesoderm induction, organogenesis, and endochondral bone formation, and regulate the fates of multipotent cell populations (Zhao, Genesis 35:43-56, 2003). BMP signals also play critical roles in physiology and disease, and are implicated in primary pulmonary hypertension, hereditary hemorrhagic telangiectasia syndrome, fibrodysplasia ossificans progressiva, and juvenile polyposis syndrome (Waite et al. Nat. Rev. Genet. 4:763-773, 2003; Papanikolaou et al. Nat. Genet. 36:77-82, 2004; Shore et al. Nat. Genet. 38:525-527, 2006).

The BMP signaling family is a diverse subset of the TGF-β superfamily (Sebald et al. Biol. Chem. 385:697-710, 2004). Over twenty known BMP ligands are recognized by three distinct type II (BMPRII, ActRIIa, and ActRIIb) and at least three type I (ALK2, ALK3, and ALK6) receptors. Dimeric ligands facilitate assembly of receptor heteromers, allowing the constitutively-active type II receptor serine/threonine kinases to phosphorylate type I receptor serine/threonine kinases. Activated type I receptors phosphorylate BMP-responsive (BR-) SMAD effectors (SMADs 1, 5, and 8) to facilitate nuclear translocation in complex with SMAD4, a co-SMAD that also facilitates TGF signaling. In addition, BMP signals can activate intracellular effectors such as MAPK p38 in a SMAD-independent manner (Nohe et al. Cell Signal 16:291-299, 2004). Soluble BMP antagonists such as noggin, chordin, gremlin, and follistatin limit BMP signaling by ligand sequestration.

A role for BMP signals in regulating expression of hepcidin, a peptide hormone and central regulator of systemic iron balance, has also been suggested (Pigeon et al. J. Biol. Chem. 276:7811-7819, 2001; Fraenkel et al. J. Clin. Invest. 115:1532-1541, 2005; Nicolas et al. Proc. Natl. Acad. Sci. U.S.A. 99:4596-4601, 2002; Nicolas et al. Nat. Genet. 34:97-101, 2003). Hepcidin binds and promotes degradation of ferroportin, the sole iron exporter in vertebrates. Loss of ferroportin activity prevents mobilization of iron to the bloodstream from intracellular stores in enterocytes, macrophages, and hepatocytes (Nemeth et al. Science 306:2090-2093, 2004). The link between BMP signaling and iron metabolism represents a potential target for therapeutics.

Given the tremendous structural diversity of the BMP and TGF-β superfamily at the level of ligands (>25 distinct ligands at present) and receptors (three type I and three type II receptors that recognize BMPs), and the heterotetrameric manner of receptor binding, traditional approaches for inhibiting BMP signals via soluble receptors, endogenous inhibitors, or neutralizing antibodies are not practical or effective. Endogenous inhibitors such as noggin and follistatin have limited specificity for ligand subclasses. Single receptors have limited affinity for ligand, whereas ligand heterotetramers exhibit rather precise specificity for particular ligands. Neutralizing antibodies are specific for particular ligands or receptors and are also limited by the structural diversity of this signaling system. Thus, there is a need in the art for pharmacologic agents that specifically antagonize BMP signaling pathways and that can be used to manipulate these pathways in therapeutic or experimental applications, such as those listed above.

SUMMARY

In accordance with the purpose(s) of the invention, as embodied and broadly described herein, the invention, in one aspect, relates to compounds useful as modulators of the BMP signaling pathway, methods of making same, pharmaceutical compositions comprising same, and methods of treating disorders associated with BMP signaling.

Disclosed is a method for the treatment of a disease state associated with modulating the BMP signaling pathway in a subject comprising administering to a subject in need thereof at least one compound in a dosage and amount effective to treat the disease state in the subject, the compound having a structure represented by the following formula (I):

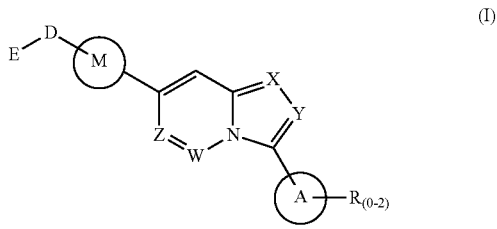

wherein:
W, X, Y, and Z are independently N or CH;
A is substituted or unsubstituted and selected from cycloalkyl, heterocycloalkyl, aryl or heteroaryl;

R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;

M is substituted or unsubstituted and is selected from aryl or heteroaryl;

D is selected from a bond, O, $CR_1R_2$ or NH or $NR_1$ or $NR_1R_2$ or $S(O)_{0-2}R_1R_2$;

E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;

$R_1$ is selected from H, alkyl, aryl, heteraryl, $COR_1$; and $R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Also disclosed are methods for modulating the BMP signaling pathway comprising administering to a subject in need thereof at least one compound in a dosage and amount effective to modulate BMP signaling, the compound having a structure represented by the following formula (I):

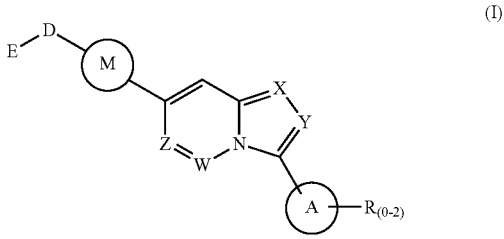

wherein:

W, X, Y, and Z are independently N or CH;

A is substituted or unsubstituted and selected from cycloalkyl, heterocycloalkyl, aryl or heteroaryl;

R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;

M is substituted or unsubstituted and is selected from aryl or heteroaryl;

D is selected from a bond, O, $CR_1R_2$ or NH or $NR_1$ or $NR_1R_2$ or $S(O)_{0-2}R_1R_2$;

E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;

$R_1$ is selected from H, alkyl, aryl, heteraryl, $COR_1$; and $R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Also disclosed are methods for the treatment of anemia, including iron deficiency, and anemia of chronic disease, comprising administering to a subject in need thereof at least one compound in a dosage and amount effective to treat the anemia, the compound having a structure represented by the following formula (I):

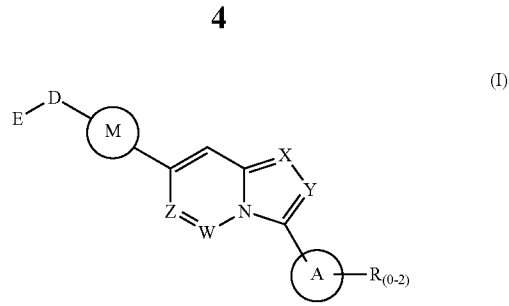

wherein:

W, X, Y, and Z are independently N or CH;

A is substituted or unsubstituted and selected from cycloalkyl, heterocycloalkyl, aryl or heteroaryl;

R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;

M is substituted or unsubstituted and is selected from aryl or heteroaryl;

D is selected from a bond, O, $CR_1R_2$ or NH or $NR_1$ or $NR_1R_2$ or $S(O)_{0-2}R_1R_2$;

E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;

$R_1$ is selected from H, alkyl, aryl, heteraryl, $COR_1$; and $R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Also disclosed are methods for the treatment of fibrodysplasia ossificans progressiva (FOP), comprising administering to a subject in need thereof at least one compound in a dosage and amount effective to treat FOP, the compound having a structure represented by the following formula (I):

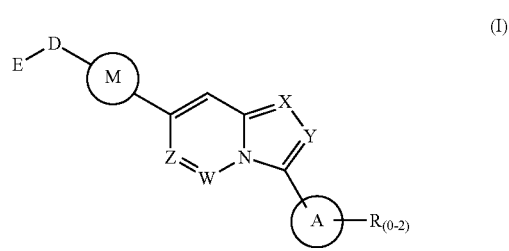

wherein:

W, X, Y, and Z are independently N or CH;

A is substituted or unsubstituted and selected from cycloalkyl, heterocycloalkyl, aryl or heteroaryl;

R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;

M is substituted or unsubstituted and selected from aryl or heteroaryl;

D is selected from a bond, O, $CR_1R_2$ or NH or $NR_1$ or $NR_1R_2$ or $S(O)_{0-2}R_1R_2$;

E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;

$R_1$ is selected from H, alkyl, aryl, heteraryl, $COR_1$; and $R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Also disclosed are methods of inhibiting the oncogenesis, growth, or metastasis of solid tumors, including breast, prostate carcinomas, bone, lung, and renal cell carcinomas, comprising administering to a subject in need thereof at least one compound in a dosage and amount effective to inhibit ontogenesis, the compound having a structure represented by the following formula (I):

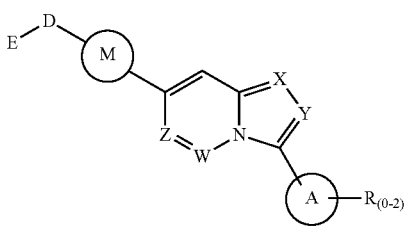

(I)

wherein:

W, X, Y, and Z are independently N or CH;

A is substituted or unsubstituted and selected from cycloalkyl, heterocycloalkyl, aryl or heteroaryl;

R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;

M is substituted or unsubstituted and selected from aryl or heteroaryl;

D is selected from a bond, O, $CR_1R_2$ or NH or $NR_1$ or $NR_1R_2$ or $S(O)_{0-2}R_1R_2$;

E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;

$R_1$ is selected from H, alkyl, aryl, heteraryl, $COR_1$; and $R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Also disclosed are methods of augmenting the inflammatory or immune response administering to a subject in need thereof at least one compound in a dosage and amount effective to augment the response, the compound having a structure represented by the following formula (I):

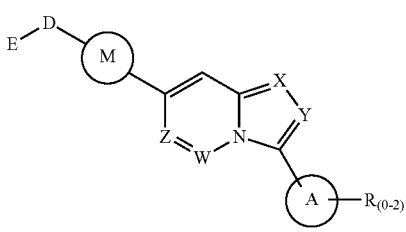

(I)

wherein:

W, X, Y, and Z are independently N or CH;

A is substituted or unsubstituted and selected from cycloalkyl, heterocycloalkyl, aryl or heteroaryl;

R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;

M is substituted or unsubstituted and is selected from aryl or heteroaryl;

D is selected from a bond, O, $CR_1R_2$ or NH or $NR_1$ or $NR_1R_2$ or $S(O)_{0-2}R_1R_2$;

E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;

$R_1$ is selected from H, alkyl, aryl, heteraryl, $COR_1$; and $R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Also disclosed are methods of treating pathologic bone function administering to a subject in need thereof at least one compound in a dosage and amount effective to treat pathologic bone function, the compound having a structure represented by the formula (I):

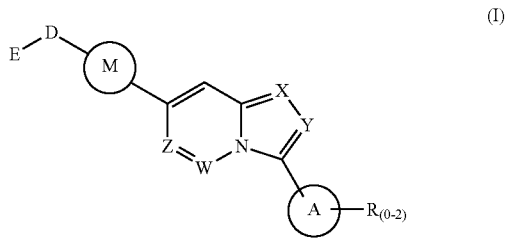

(I)

wherein:

W, X, Y, and Z are independently N or CH;

A is substituted or unsubstituted and selected from cycloalkyl, heterocycloalkyl, aryl or heteroaryl;

R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;

M is substituted or unsubstituted and is selected from aryl or heteroaryl;

D is selected from a bond, O, $CR_1R_2$ or NH or $NR_1$ or $NR_1R_2$ or $S(O)_{0-2}R_1R_2$; E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;

$R_1$ is selected from H, alkyl, aryl, heteraryl, $COR_1$; and $R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Also disclosed are methods for treating ectopic or maladaptive bone formation in a subject in need thereof, comprising administering to a subject in need thereof at least one compound in a dosage and amount effective to treat ectopic or maladaptive bone formation, the compound having a structure represented by the following formula (I):

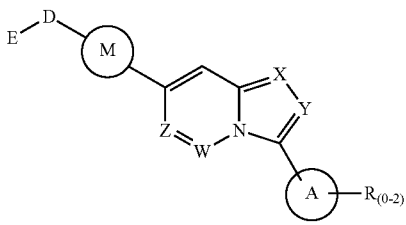

wherein:
W, X, Y, and Z are independently N or CH;
A is substituted or unsubstituted and selected from cycloalkyl, heterocycloalkyl, aryl or heteroaryl;
R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;
M is substituted or unsubstituted and is selected from aryl or heteroaryl;
D is selected from a bond, O, $CR_1R_2$ or NH or $NR_1$ or $NR_1R_2$ or $S(O)_{0-2}R_1R_2$;
E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;
$R_1$ is selected from H, alkyl, aryl, heteraryl, $COR_1$; and
$R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Also disclosed are methods of treating a skin disease in a subject in need thereof, comprising administering to a subject in need thereof at least one compound in a dosage and amount effective to treat the skin disease, the compound having a structure represented by the following formula (I):

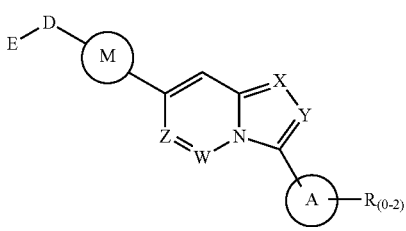

wherein:
W, X, Y, and Z are independently N or CH;
A is substituted or unsubstituted and selected from cycloalkyl, heterocycloalkyl, aryl or heteroaryl;
R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;
M is substituted or unsubstituted and is selected from aryl or heteroaryl;
D is selected from a bond, O, $CR_1R_2$ or NH or $NR_1$ or $NR_1R_2$ or $S(O)_{0-2}R_1R_2$;
E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;
$R_1$ is selected from H, alkyl, aryl, heteraryl, $COR_1$; and
$R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Also disclosed are methods of treating hypertension in a subject in need thereof, comprising administering to a subject in need thereof at least one compound in a dosage and amount effective to treat hypertension, the compound having a structure represented by the following formula (I):

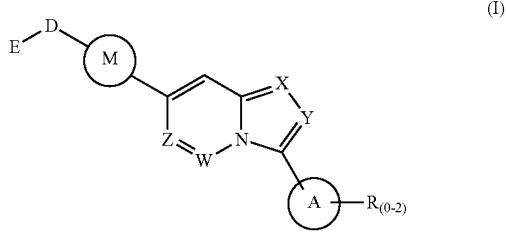

wherein:
W, X, Y, and Z are independently N or CH;
A is substituted or unsubstituted and selected from cycloalkyl, heterocycloalkyl, aryl or heteroaryl;
R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;
M is substituted or unsubstituted and is selected from aryl or heteroaryl;
D is selected from a bond, O, $CR_1R_2$ or NH or $NR_1$ or $NR_1R_2$ or $S(O)_{0-2}R_1R_2$;
E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;
$R_1$ is selected from H, alkyl, aryl, heteraryl, $COR_1$; and
$R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Also disclosed are methods of treating ventricular hypertrophy in a subject in need thereof, comprising administering to a subject in need thereof at least one compound in a dosage and amount effective to treat ventricular hypertrophy, the compound having a structure represented by the following formula (I):

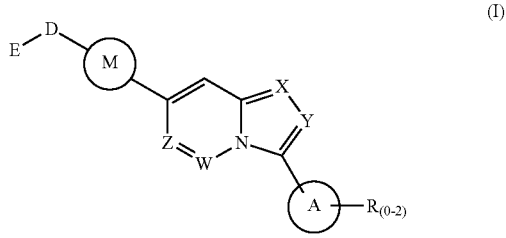

wherein:
W, X, Y, and Z are independently N or CH;
A is substituted or unsubstituted and selected from cycloalkyl, heterocycloalkyl, aryl or heteroaryl;

R is selected from H, CF$_3$, halogen, CN, alkyl, aryl, heteroaryl, NR$_1$R$_2$, COR$_1$R$_2$, CR$_1$R$_2$, S(O)$_{0-2}$NR$_1$R$_2$; S(O)$_{0-2}$R$_1$R$_2$;

M is substituted or unsubstituted and is selected from aryl or heteroaryl;

D is selected from a bond, O, CR$_1$R$_2$ or NH or NR$_1$ or NR$_1$R$_2$ or S(O)$_{0-2}$R$_1$R$_2$;

E is selected from H, CF$_3$, halogen, CN, alkyl, aryl, heteroaryl, C$_3$-C$_{12}$ cycloalkyl or C$_3$-C$_{12}$ cycloheteroalkyl or —(CH$_2$)$_x$—C$_3$-C$_{12}$ cycloalkyl or —(CH$_2$)$_x$—C$_3$-C$_{12}$ cycloheteroalkyl;

R$_1$ is selected from H, alkyl, aryl, heteraryl, COR$_1$; and

R$_2$ is selected from H, alkyl, aryl, heteraryl, COR$_1$, and further, R$_1$ and R$_2$ can form a C$_3$-C$_{12}$ cycloalkyl or C$_3$-C$_{12}$ cycloheteroalkyl containing O, N or S; or a pharmaceutically acceptable salt thereof, or a pharmaceutically acceptable derivative thereof.

Also disclosed are methods of treating spinal cord injury and neuropathy in a subject in need thereof, comprising administering to a subject in need thereof at least one compound in a dosage and amount effective to treat spinal cor, the compound having a structure represented by the following formula (I):

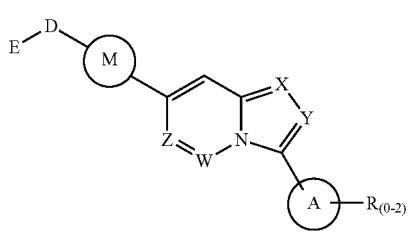

(I)

wherein:

W, X, Y, and Z are independently N or CH;

A is substituted or unsubstituted and selected from cycloalkyl, heterocycloalkyl, aryl or heteroaryl;

R is selected from H, CF$_3$, halogen, CN, alkyl, aryl, heteroaryl, NR$_1$R$_2$, COR$_1$R$_2$, CR$_1$R$_2$, S(O)$_{0-2}$NR$_1$R$_2$; S(O)$_{0-2}$R$_1$R$_2$;

M is substituted or unsubstituted and is selected from aryl or heteroaryl;

D is selected from a bond, O, CR$_1$R$_2$ or NH or NR$_1$ or NR$_1$R$_2$ or S(O)$_{0-2}$R$_1$R$_2$;

E is selected from H, CF$_3$, halogen, CN, alkyl, aryl, heteroaryl, C$_3$-C$_{12}$ cycloalkyl or C$_3$-C$_{12}$ cycloheteroalkyl or —(CH$_2$)$_x$—C$_3$-C$_{12}$ cycloalkyl or —(CH$_2$)$_x$—C$_3$-C$_{12}$ cycloheteroalkyl;

R$_1$ is selected from H, alkyl, aryl, heteraryl, COR$_1$; and

R$_2$ is selected from H, alkyl, aryl, heteraryl, COR$_1$, and further, R$_1$ and R$_2$ can form a C$_3$-C$_{12}$ cycloalkyl or C$_3$-C$_{12}$ cycloheteroalkyl containing O, N or S; or a pharmaceutically acceptable salt thereof, or a pharmaceutically acceptable derivative thereof.

Also disclosed are methods of treating atherosclerosis in a subject in need thereof, comprising administering to a subject in need thereof at least one compound in a dosage and amount effective to modulate BMP signaling, the compound having a structure represented by the following formula (I):

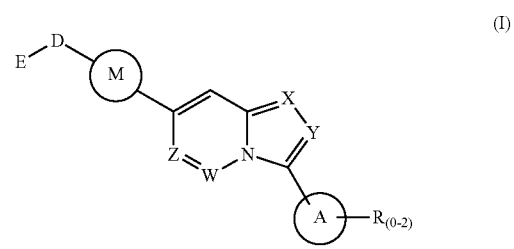

(I)

wherein:

W, X, Y, and Z are independently N or CH;

A is substituted or unsubstituted and selected from cycloalkyl, heterocycloalkyl, aryl or heteroaryl;

R is selected from H, CF$_3$, halogen, CN, alkyl, aryl, heteroaryl, NR$_1$R$_2$, COR$_1$R$_2$, CR$_1$R$_2$, S(O)$_{0-2}$NR$_1$R$_2$; S(O)$_{0-2}$R$_1$R$_2$;

M is substituted or unsubstituted and is selected from aryl or heteroaryl;

D is selected from a bond, O, CR$_1$R$_2$ or NH or NR$_1$ or NR$_1$R$_2$ or S(O)$_{0-2}$R$_1$R$_2$;

E is selected from H, CF$_3$, halogen, CN, alkyl, aryl, heteroaryl, C$_3$-C$_{12}$ cycloalkyl or C$_3$-C$_{12}$ cycloheteroalkyl or —(CH$_2$)$_x$—C$_3$-C$_{12}$ cycloalkyl or —(CH$_2$)$_x$—C$_3$-C$_{12}$ cycloheteroalkyl;

R$_1$ is selected from H, alkyl, aryl, heteraryl, COR$_1$; and

R$_2$ is selected from H, alkyl, aryl, heteraryl, COR$_1$, and further, R$_1$ and R$_2$ can form a C$_3$-C$_{12}$ cycloalkyl or C$_3$-C$_{12}$ cycloheteroalkyl containing O, N or S; or a pharmaceutically acceptable salt thereof, or a pharmaceutically acceptable derivative thereof.

Also disclosed are methods for treating acute megakaryoblastic leukemia, comprising administering to a subject in need thereof at least one compound in a dosage and amount effective to propagate a cell, the compound having a structure represented by the following formula (I):

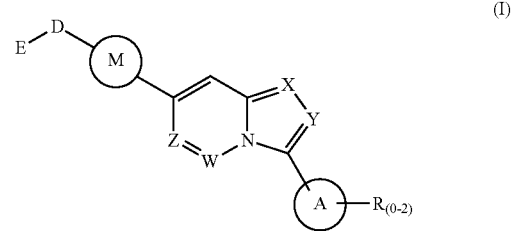

(I)

wherein:

W, X, Y, and Z are independently N or CH;

A is substituted or unsubstituted and selected from cycloalkyl, heterocycloalkyl, aryl or heteroaryl;

R is selected from H, CF$_3$, halogen, CN, alkyl, aryl, heteroaryl, NR$_1$R$_2$, COR$_1$R$_2$, CR$_1$R$_2$, S(O)$_{0-2}$NR$_1$R$_2$; S(O)$_{0-2}$R$_1$R$_2$;

M is substituted or unsubstituted and is selected from aryl or heteroaryl;

D is selected from a bond, O, CR$_1$R$_2$ or NH or NR$_1$ or NR$_1$R$_2$ or S(O)$_{0-2}$R$_1$R$_2$;

E is selected from H, CF$_3$, halogen, CN, alkyl, aryl, heteroaryl, C$_3$-C$_{12}$ cycloalkyl or C$_3$-C$_{12}$ cycloheteroalkyl or —(CH$_2$)$_x$—C$_3$-C$_{12}$ cycloalkyl or —(CH$_2$)$_x$—C$_3$-C$_{12}$ cycloheteroalkyl;

R$_1$ is selected from H, alkyl, aryl, heteraryl, COR$_1$; and $R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Also disclosed are methods for at least one of promoting or enhancing liver restoration of liver mass, treating liver damage, treating liver disease, or treating acetaminophen overdose in a subject in need thereof, comprising administering to a subject in need thereof at least one compound in a dosage and amount effective to propagate a cell, the compound having a structure represented by the following formula (I):

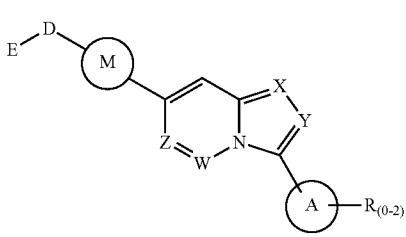

(I)

wherein:
W, X, Y, and Z are independently N or CH;
A is substituted or unsubstituted and selected from cycloalkyl, heterocycloalkyl, aryl or heteroaryl;
R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;
M is substituted or unsubstituted and is selected from aryl or heteroaryl;
D is selected from a bond, O, $CR_1R_2$ or NH or $NR_1$ or $NR_1R_2$ or $S(O)_{0-2}R_1R_2$;
E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;
$R_1$ is selected from H, alkyl, aryl, heteraryl, $COR_1$; and
$R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Also disclosed are methods for at least one of treating heart disease, treating heart damage, promoting, inducing, or enhancing modulation of epicardial activation and epithelial-to-mesenchyme transition; or a method of inducing, enhancing, or promoting cardiomyocyte formation; comprising administering to a subject in need thereof at least one compound in a dosage and amount effective to propagate a cell, the compound having a structure represented by the following formula (I):

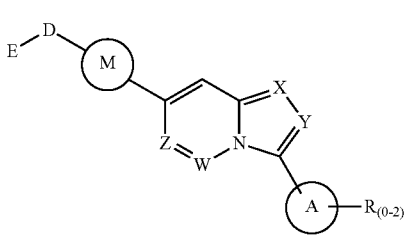

(I)

wherein:
W, X, Y, and Z are independently N or CH;
A is substituted or unsubstituted and selected from cycloalkyl, heterocycloalkyl, aryl or heteroaryl;
R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;
M is substituted or unsubstituted and is selected from aryl or heteroaryl;
D is selected from a bond, O, $CR_1R_2$ or NH or $NR_1$ or $NR_1R_2$ or $S(O)_{0-2}R_1R_2$;
E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;
$R_1$ is selected from H, alkyl, aryl, heteraryl, $COR_1$; and
$R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Also disclosed are methods for at least one of propagation, engraftment, and differentiation of progenitor cells, comprising administering to a subject in need thereof at least one compound in a dosage and amount effective to propagate a cell, the compound having a structure represented by the following formula (I):

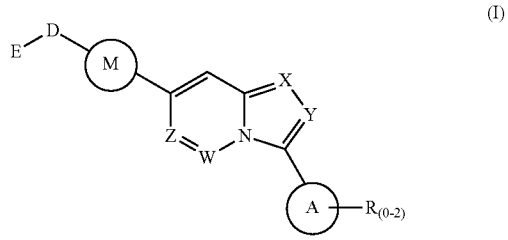

(I)

wherein:
W, X, Y, and Z are independently N or CH;
A is substituted or unsubstituted and selected from cycloalkyl, heterocycloalkyl, aryl or heteroaryl;
R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;
M is substituted or unsubstituted and is selected from aryl or heteroaryl;
D is selected from a bond, O, $CR_1R_2$ or NH or $NR_1$ or $NR_1R_2$ or $S(O)_{0-2}R_1R_2$;
E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;
$R_1$ is selected from H, alkyl, aryl, heteraryl, $COR_1$; and
$R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Also disclosed are also disclosed are compounds and compositions that comprises the compounds disclosed herein. The compounds disclosed herein include those having a structure represented by the formula (I):

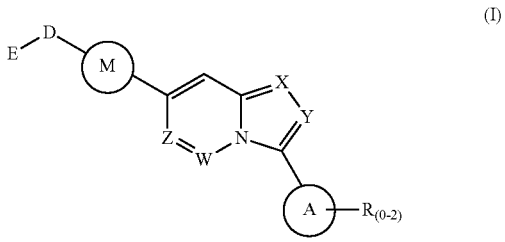

wherein:

W, X, Y, and Z are independently N or CH;

A is substituted or unsubstituted and selected from cycloalkyl, heterocycloalkyl, aryl or heteroaryl;

R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;

M is substituted or unsubstituted and is selected from aryl or heteroaryl;

D is selected from a bond, O, $CR_1R_2$ or NH or $NR_1$ or $NR_1R_2$ or $S(O)_{0-2}R_1R_2$;

E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;

$R_1$ is selected from H, alkyl, aryl, heteraryl, $COR_1$; and $R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Other embodiments of the present invention include methods of treating at least one of myocardial ischemic injury, retinopathy of prematurity, diabetic retinopathy, and wet macular degeneration, aortic valve calcification (both native and prosthetic), vascular calcification, diabetic nephropathy and renal fibrosis, hereditary spastic paraplegias, dystrophic phenotype in Duchenne Muscular Dystrophy, inflammatory bowel disease, childhood leukemias, cancer metastasis by targeting lymphatics and primary tumor growth; and methods of promoting liver regeneration and healing following acute injury, including hepatotoxin exposure such as Tylenol overdose; by administering an effective amount of a compound of the present invention to a subject in need thereof.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

As used herein, the term "subject" refers to a target of administration. The subject of the herein disclosed methods can be a vertebrate, such as a mammal, a fish, a bird, a reptile, insect, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment that includes modulation of the BMP signaling pathway.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by inhibition of bone morphogenetic protein activity" means having been subjected to a physical examination by a person of skill, for example, a physician, and found to have a condition that can be diagnosed or treated by a compound or composition that can favorably inhibit BMP or BMP activity. As a further example, "diagnosed with a need for inhibition of BMP or BMP activity" refers to having been subjected to a physical examination by a person of skill, for example, a physician, and found to have a condition characterized by abnormal BMP activity. Such a diagnosis can be in reference to a disorder, such as fibrodysplasia ossificans progressiva, and the like, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder related to abnormal BMP activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by a formula —(CH$_2$)$_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by a formula —C(O)H. Throughout this specification "C(O)" is a short hand notation for a carbonyl group, i.e., C═O.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "carboxylic acid" as used herein is represented by a formula —C(O)OH.

The term "ester" as used herein is represented by a formula —OC(O)$A^1$ or —C(O)O$A^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by a formula —$(A^1O(O)C-A^2-C(O)O)_a$— or —$(A^1O(O)C-A^2-OC(O))_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by a formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by a formula —$(A^1O-A^2O)_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by a formula —OH.

The term "ketone" as used herein is represented by a formula $A^1C(O)A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by a formula —$N_3$.

The term "nitro" as used herein is represented by a formula —$NO_2$.

The term "nitrile" as used herein is represented by a formula —CN.

The term "silyl" as used herein is represented by a formula —SiA$^1$A$^2$A$^3$, where A$^1$, A$^2$, and A$^3$ can be, independently, hydrogen or an optionally substituted alkyl, cycloalkyl, alkoxy, alkenyl, cycloalkenyl, alkynyl, cycloalkynyl, aryl, or heteroaryl group as described herein.

The term "sulfo-oxo" as used herein is represented by a formulas —S(O)A$^1$, —S(O)$_2$A$^1$, —OS(O)$_2$A$^1$, or —OS(O)$_2$OA$^1$, where A$^1$ can be hydrogen or an optionally substituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by a formula —S(O)$_2$A$^1$, where A$^1$ can be hydrogen or an optionally substituted alkyl, cycloalkyl, alkenyl, cycloalkenyl, alkynyl, cycloalkynyl, aryl, or heteroaryl group as described herein. The term "sulfone" as used herein is represented by a formula A$^1$S(O)$_2$A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein. The term "sulfoxide" as used herein is represented by a formula A'S(O)A$^2$, where A$^1$ and A$^2$ can be, independently, an optionally substituted alkyl, cycloalkyl, alkenyl, cycloalkenyl, alkynyl, cycloalkynyl, aryl, or heteroaryl group as described herein.

The term "thiol" as used herein is represented by a formula —SH.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

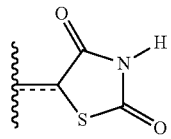

regardless of whether thiazolidinedione is used to prepare the compound. In some aspects the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some aspects, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Typically, inorganic radicals do not comprise metalloids elements such as boron, aluminum, gallium, germanium, arsenic, tin, lead, or tellurium, or the noble gas elements, unless otherwise specifically indicated elsewhere herein.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "hydrolysable residue" is meant to refer to a functional group capable of undergoing hydrolysis, e.g., under basic or acidic conditions. Examples of hydrolysable residues include, without limitation, residues of acid halides or activated carboxylic acids, residues of trialkylsilyl halides, residues of alkyloxymethyl halides, and various other protecting groups known in the art (see, for example, "Protective Groups in Organic Synthesis," T. W. Greene, P. G. M. Wuts, Wiley-Interscience, 1999).

The term "leaving group" refers to an atom (or a group of atoms) with electron withdrawing ability that can be displaced as a stable species, taking with it the bonding electrons. Examples of suitable leaving groups include sulfonate esters, including, but not limited to, triflate, mesylate, tosylate, brosylate, and halides.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Of course, when a variable is present in more than one instance, it may be the same or different in each occurrence. In other words, each variable is independent from the other. In some aspects, a structure of a compound can be represented by a formula:

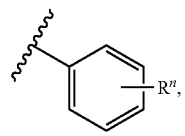

which is understood to be equivalent to a formula:

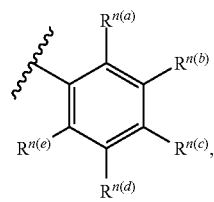

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance. Likewise, when a group R is defined as four substituents, R is understood to represent four independent substituents, $R^a$, $R^b$, $R^c$, and $R^d$. Unless indicated to the contrary, the substituents are not limited to any particular order or arrangement.

The following abbreviations are used herein. DMF: dimethyl formamide. EtOAc: ethyl acetate. THF: tetrahydrofuran. DIPEA or DIEA: diisopropylethylamine. HOBt: 1-hydroxybenzotriazole. EDC: 1-ethyl-3-[3-dimethylaminopropyl]carbodiimide hydrochloride. DMSO: dimethylsulfoxide. DMAP: 4-Dimethylaminopyridine. RT: Room temperature. h: Hours. Min: Minutes. DCM: Dichloromethane. MeCN: Acetonitrile. MeOH: methanol. iPrOH: 2-Propanol. n-BuOH: 1-Butanol.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds, or pharmaceutically acceptable derivatives thereof, useful as BMP inhibitors. In general, it is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

In one aspect, the present invention relates to compounds having a structure represented by the following formula (I):

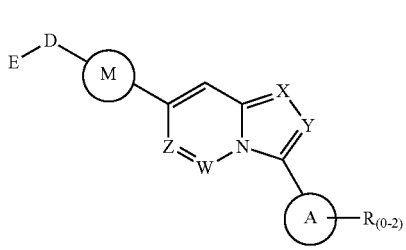

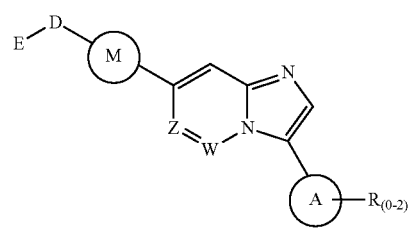

wherein:

W, X, Y, and Z are independently N or CH;

A is substituted or unsubstituted and selected from cycloalkyl, heterocycloalkyl, aryl or heteroaryl;

R is selected from H, $CF_3$, halogen, CN, alkyl, aryl, heteroaryl, $NR_1R_2$, $COR_1R_2$, $CR_1R_2$, $S(O)_{0-2}NR_1R_2$, $S(O)_{0-2}R_1R_2$;

M is substituted or unsubstituted and selected from aryl or heteroaryl;

D is selected from a bond, O, $CR_1R_2$ or NH or $NR_1$ or $NR_1R_2$ or $S(O)_{0-2}R_1R_2$;

E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;

$R_1$ is selected from H, alkyl, aryl, heteraryl, $COR_1$; and $R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Also disclosed are compounds of formula (I), where Z, X, and Y together help form:

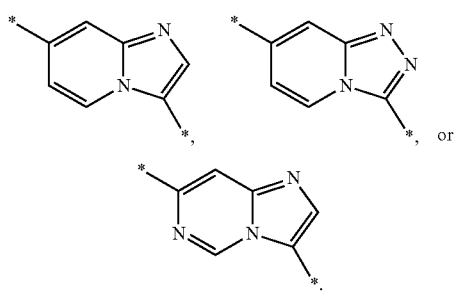

Also disclosed are compounds of formula (I), where Z, X, and Y together help form:

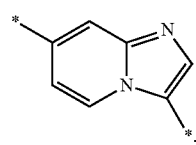

Also disclosed are compounds having a structure represented by the following formula (II):

wherein:

W and Z are independently N or CH;

A is substituted or unsubstituted and is selected from cycloalkyl, heterocycloalkyl, aryl or heteroaryl;

R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;

M is substituted or unsubstituted and selected from aryl or heteroaryl;

D is selected from a bond, O, $CR_1R_2$ or NH or $NR_1$ or $NR_1R_2$ or $S(O)_{0-2}R_1R_2$;

E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;

$R_1$ is selected from H, alkyl, aryl, heteraryl, $COR_1$; and $R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Also disclosed are compounds having a structure represented by the following formula (III)

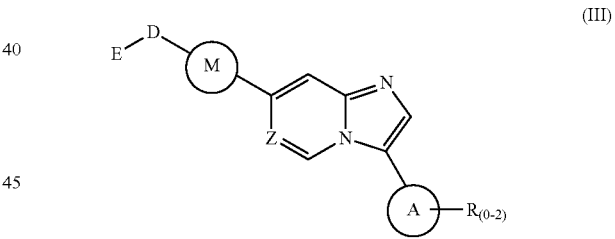

wherein:

Z is N or CH;

A is substituted or unsubstituted and is selected from cycloalkyl, heterocycloalkyl, aryl or heteroaryl;

R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;

M is substituted or unsubstituted and selected from aryl or heteroaryl;

D is selected from a bond, O, $CR_1R_2$ or NH or $NR_1$ or $NR_1R_2$ or $S(O)_{0-2}R_1R_2$;

E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;

$R_1$ is selected from H, alkyl, aryl, heteraryl, $COR_1$; and $R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

Also disclosed are compounds of formula (I), wherein

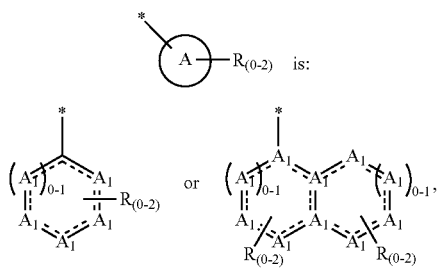 is:

wherein $A_1$ is independently O, $CR_1R_2$ or NH or $NR_1$ or $NR_1R_2$, or can join with another $A_1$ to form $C_3$-$C_{12}$ cycloalkyl or $C_3$-$C_{12}$ cycloalkenyl or aryl or heteroaryl or $C_3$-$C_{12}$ heterocycloalkyl or $C_3$-$C_{12}$ heterocycloalkenyl or 3-8 membered ring comprising C, O, S, and/or N.

Also disclosed are compounds of formula (I), wherein M is optionally substituted with one or more R, and is selected from $C_3$-$C_{12}$ cycloalkyl or $C_3$-$C_{12}$ cycloalkenyl or aryl or heteroaryl or $C_3$-$C_{12}$ heterocycloalkyl or $C_3$-$C_{12}$ heterocycloalkenyl or 3-8 membered ring comprising C, O, S, and/or N.

Also disclosed are compounds where M is optionally substituted phenyl or pyridine.

Also disclosed are compounds of formula (I), where M, D, and E together form:

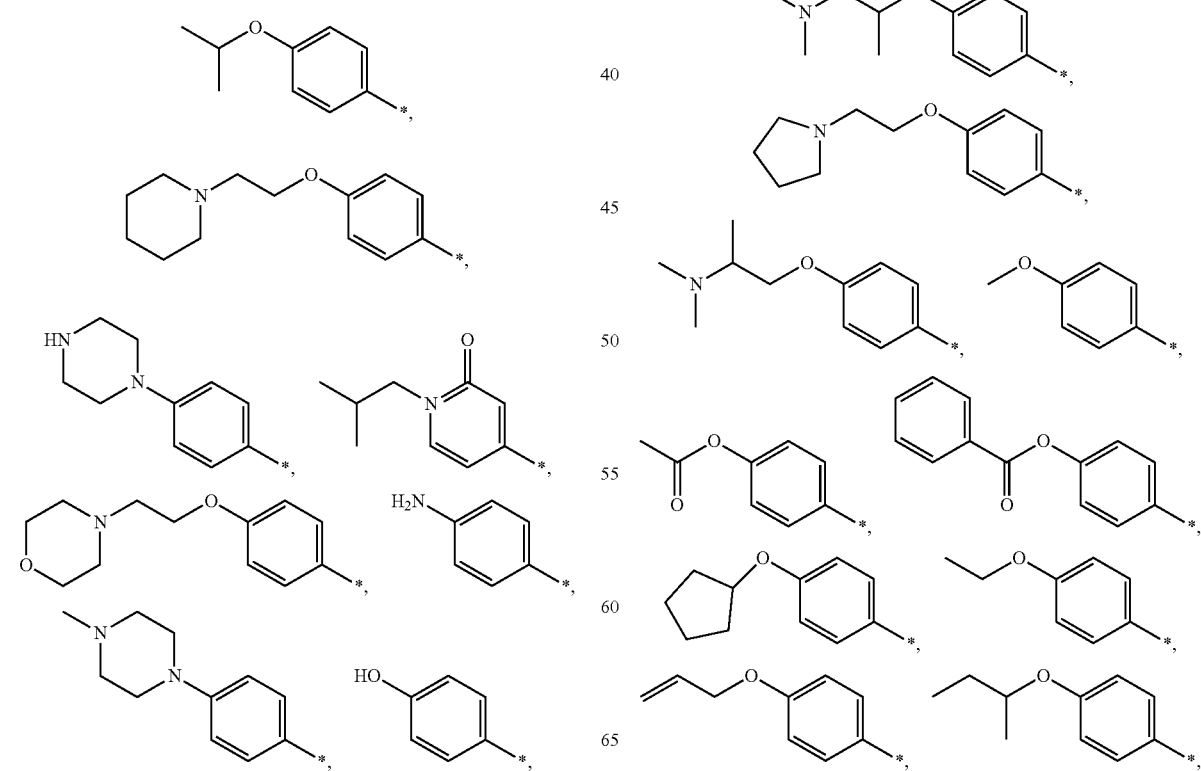

-continued

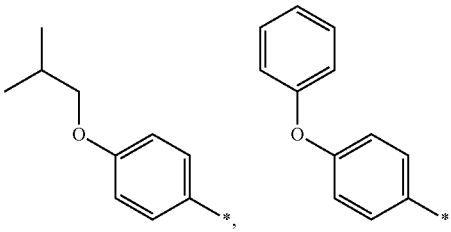

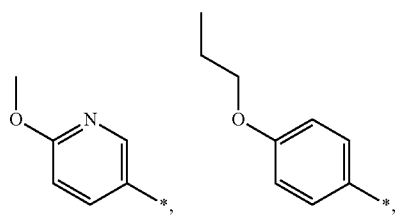

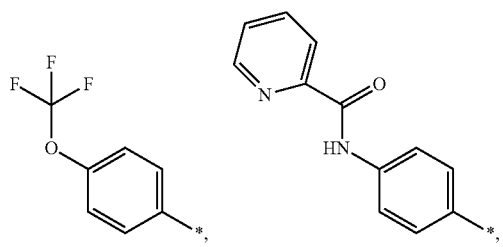

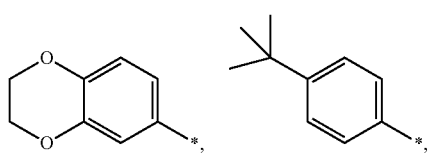

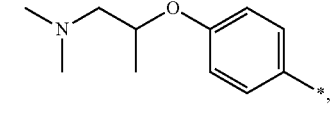

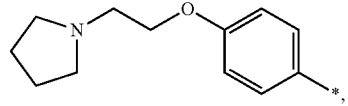

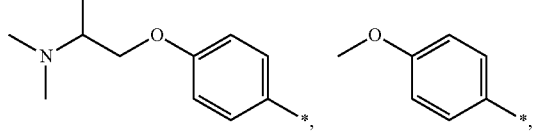

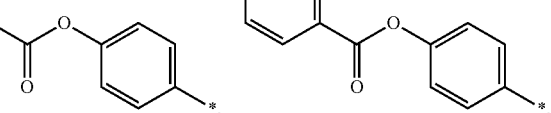

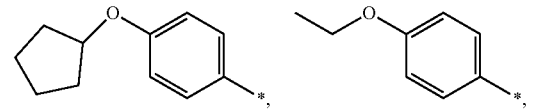

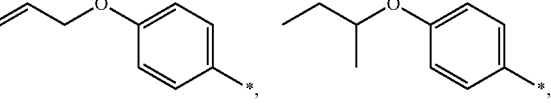

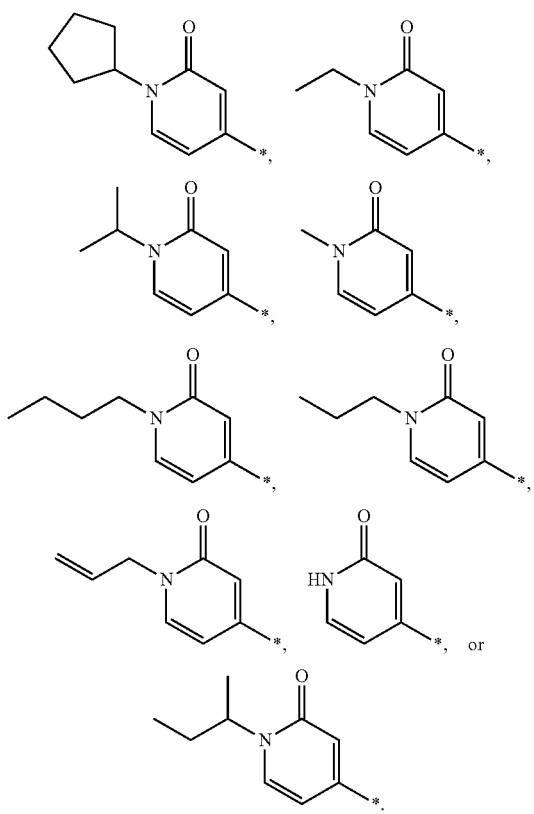
Also disclosed are compounds of formula (I), where A is chosen from the following:
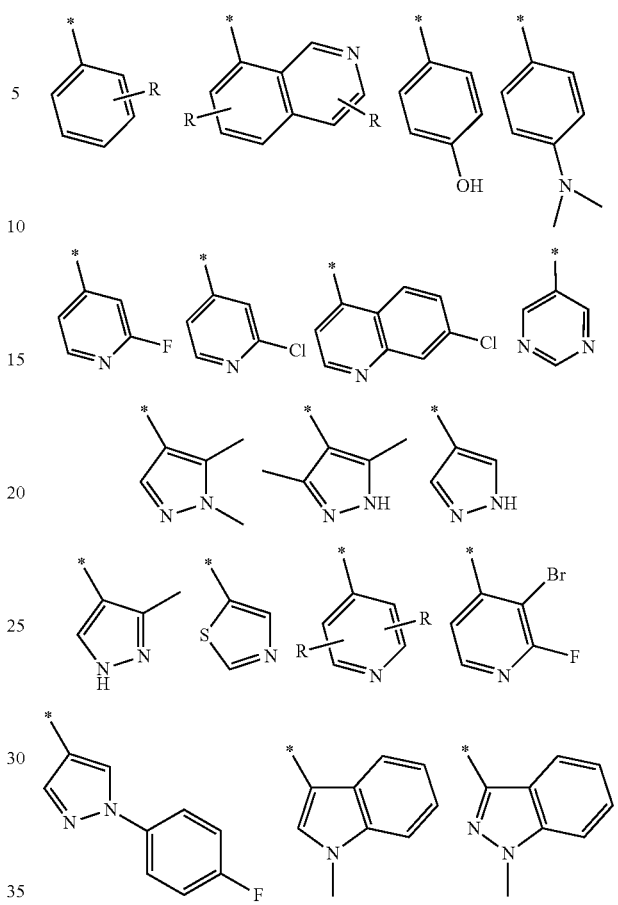
Also disclosed are compound of formula (I), of the following formula:
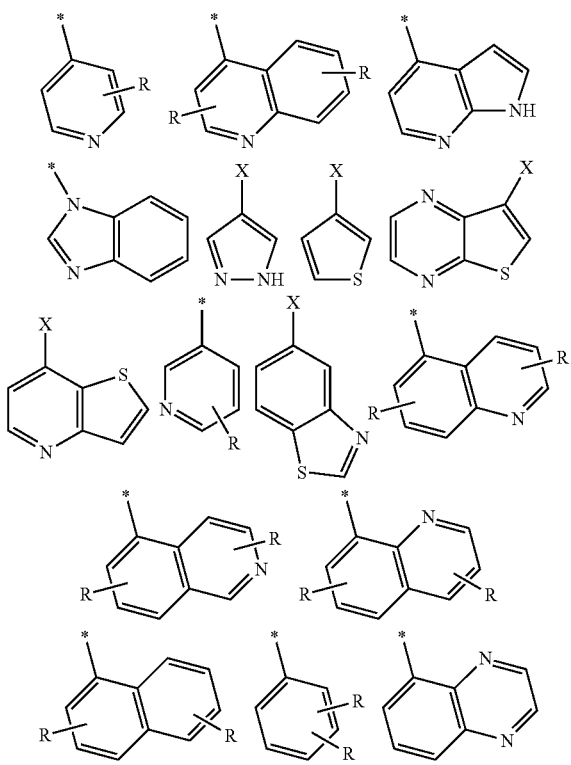

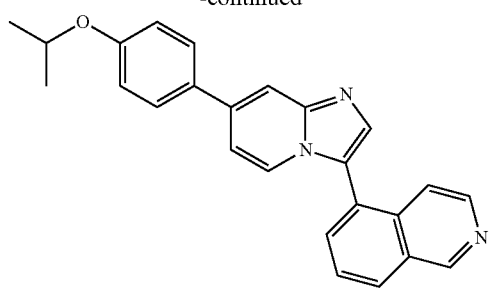
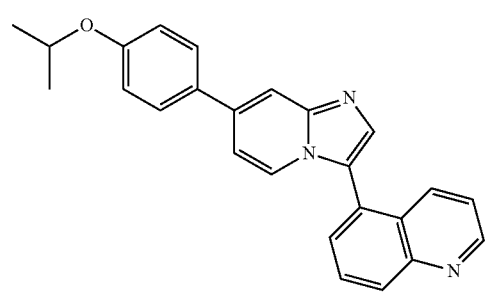 [SMILES: CC(C)Oc1ccc(-c2ccn3c(-c4cccc5ncccc45)cnc3c2)cc1]
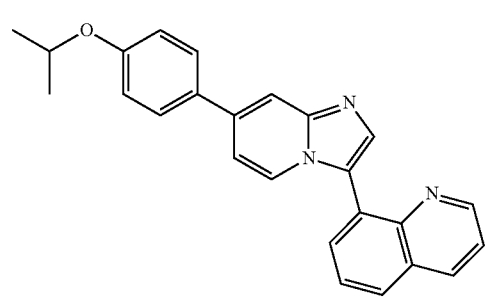 [SMILES: CC(C)Oc1ccc(-c2ccn3c(-c4cccc5cccnc45)cnc3c2)cc1]
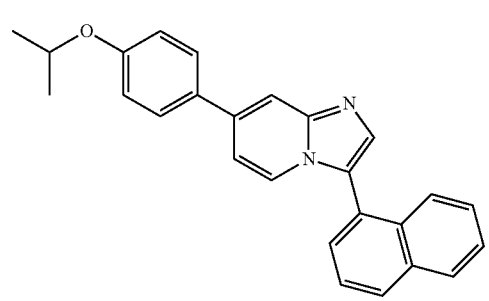 [SMILES: CC(C)Oc1ccc(-c2ccn3c(-c4cccc5ccccc45)cnc3c2)cc1]
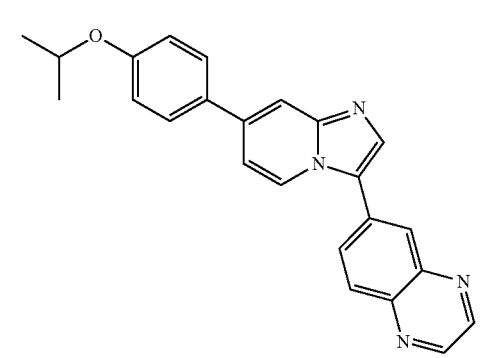 [SMILES: CC(C)Oc1ccc(-c2ccn3c(-c4ccc5nccnc5c4)cnc3c2)cc1]
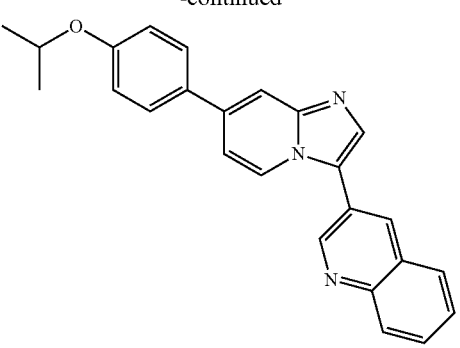
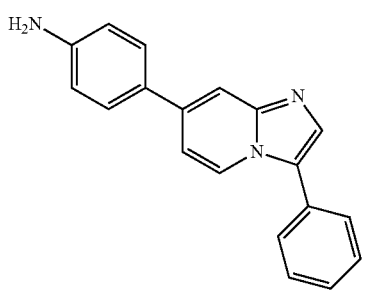 [SMILES: Nc1ccc(-c2ccn3c(-c4ccccc4)cnc3c2)cc1]
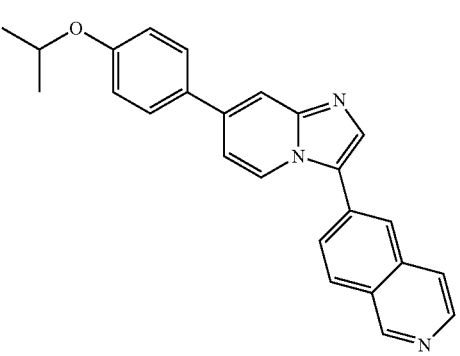 [SMILES: CC(C)Oc1ccc(-c2ccn3c(-c4ccc5cnccc5c4)cnc3c2)cc1]
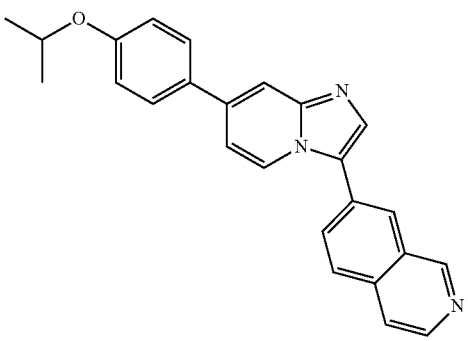 [SMILES: CC(C)Oc1ccc(-c2ccn3c(-c4ccc5ccncc5c4)cnc3c2)cc1]
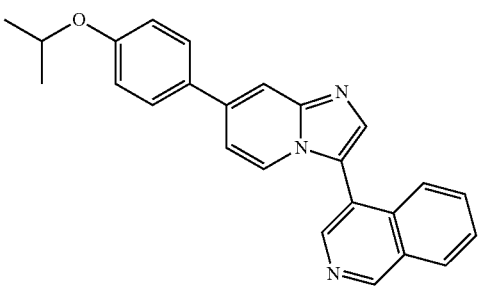 [SMILES: CC(C)Oc1ccc(-c2ccn3c(-c4cncc5ccccc45)cnc3c2)cc1]

33
-continued
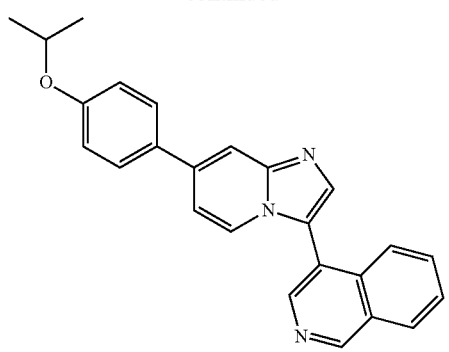
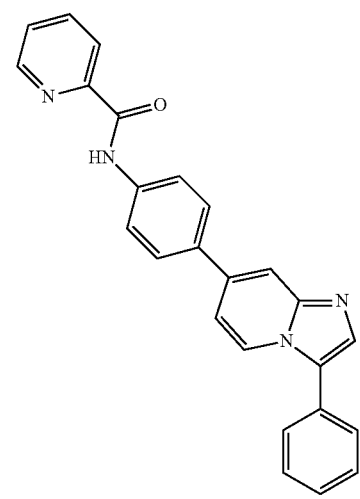
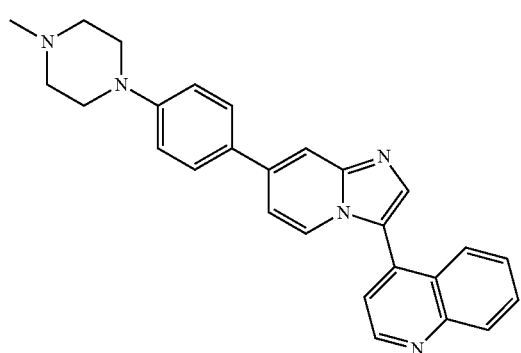 [SMILES: CN1CCN(c2ccc(-c3ccn4c(-c5ccnc6ccccc56)cnc4c3)cc2)CC1]
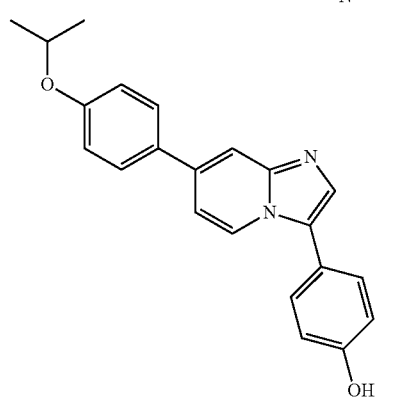
34
-continued
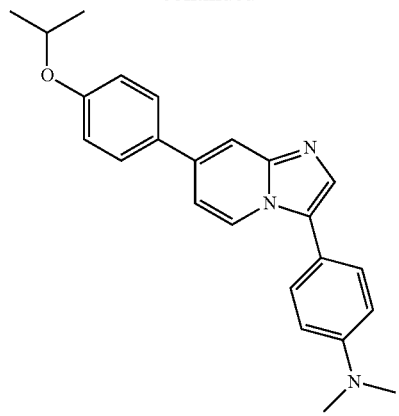
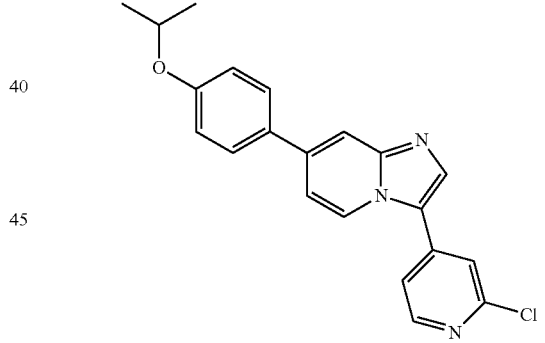
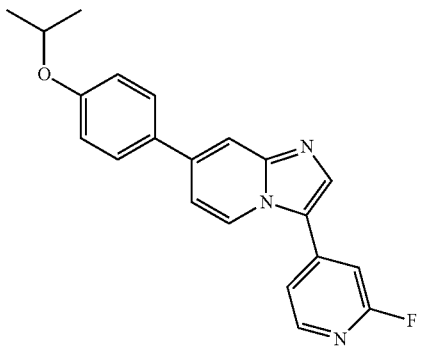

35
-continued
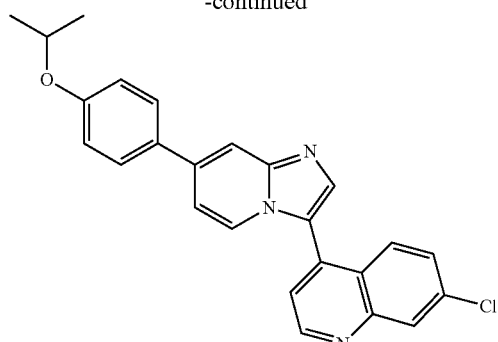
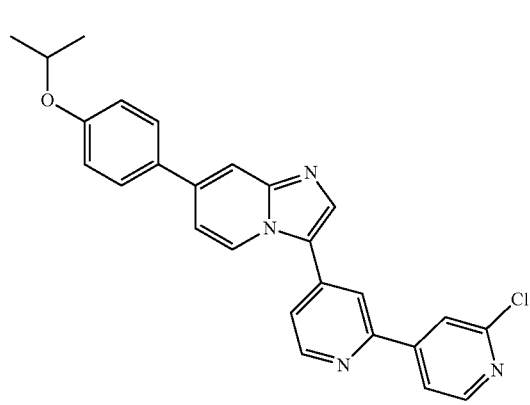
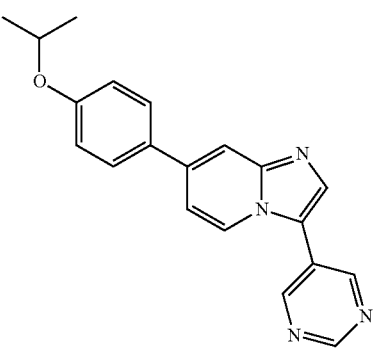
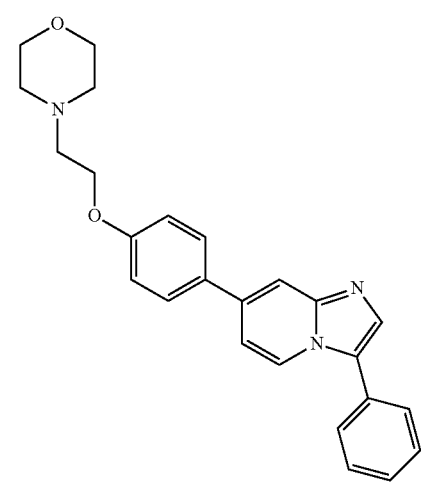
36
-continued
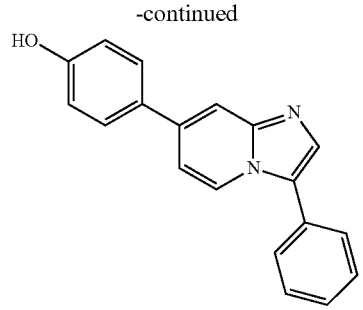
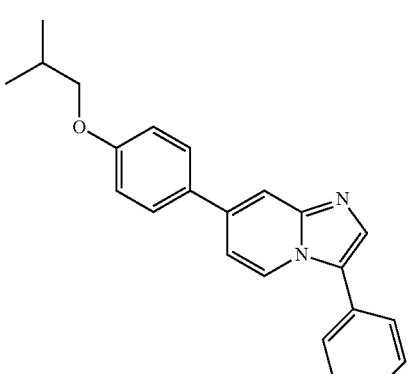
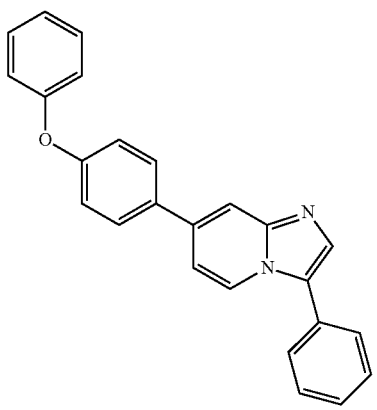
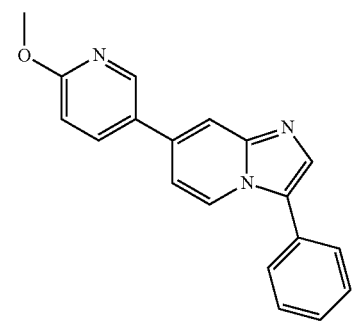

37
-continued
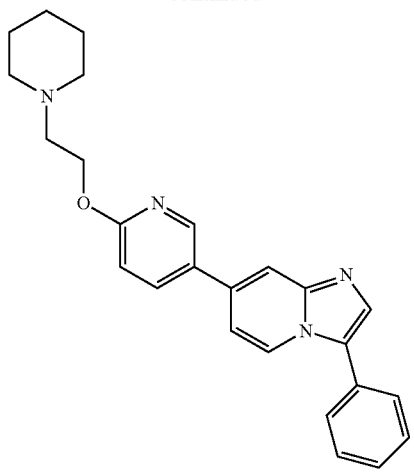
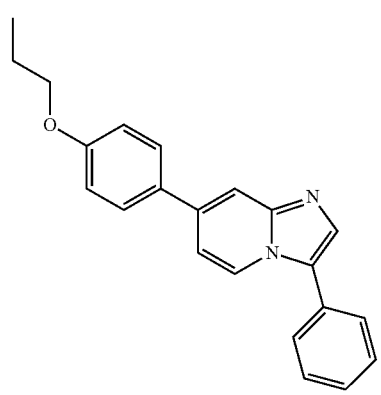
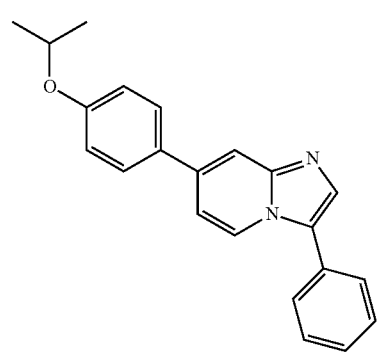
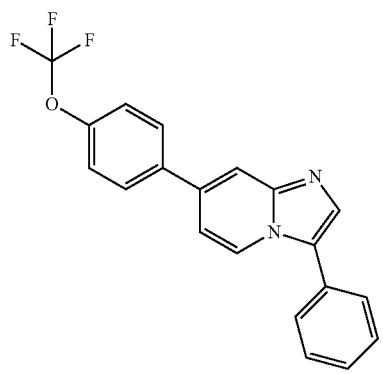
38
-continued
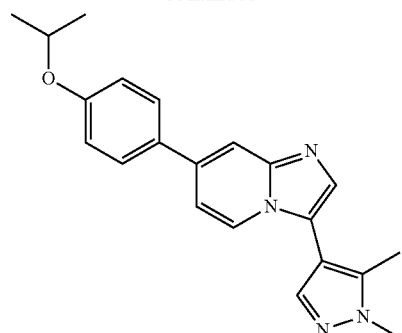
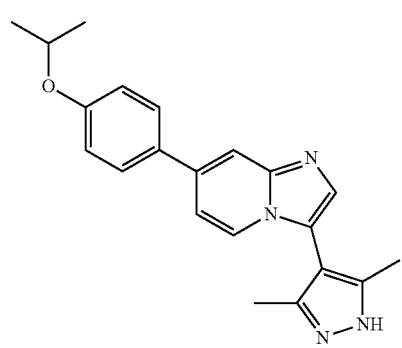
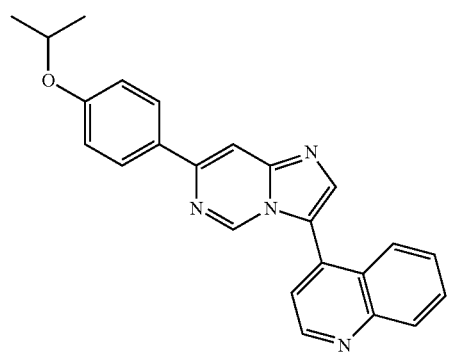
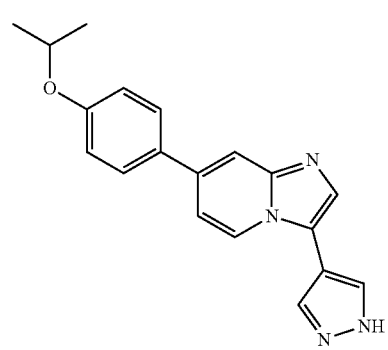

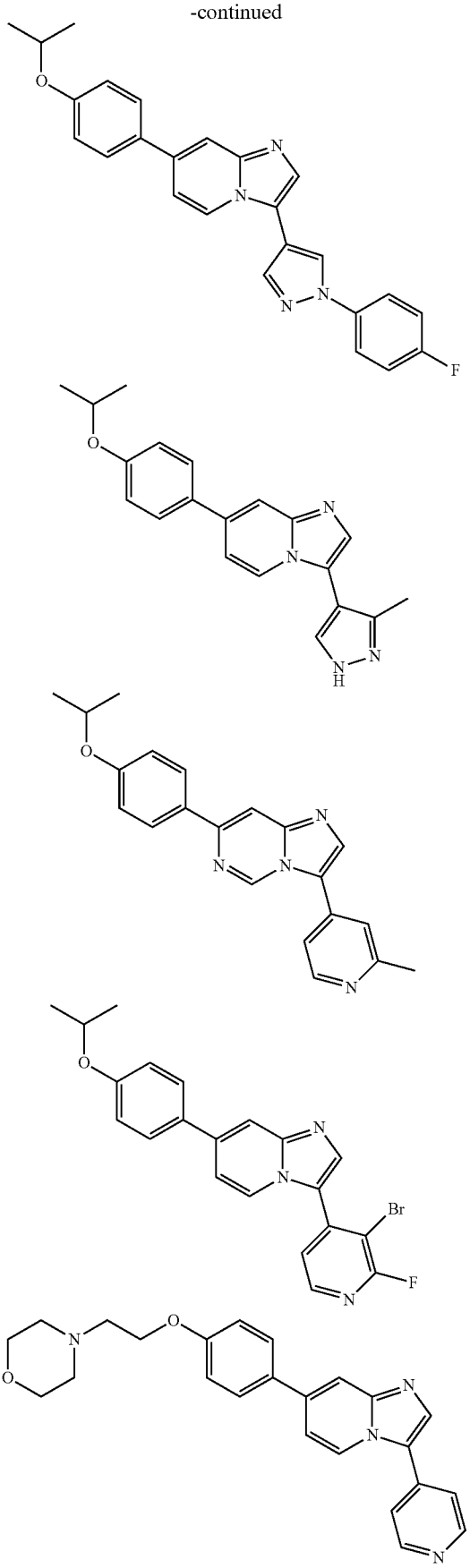
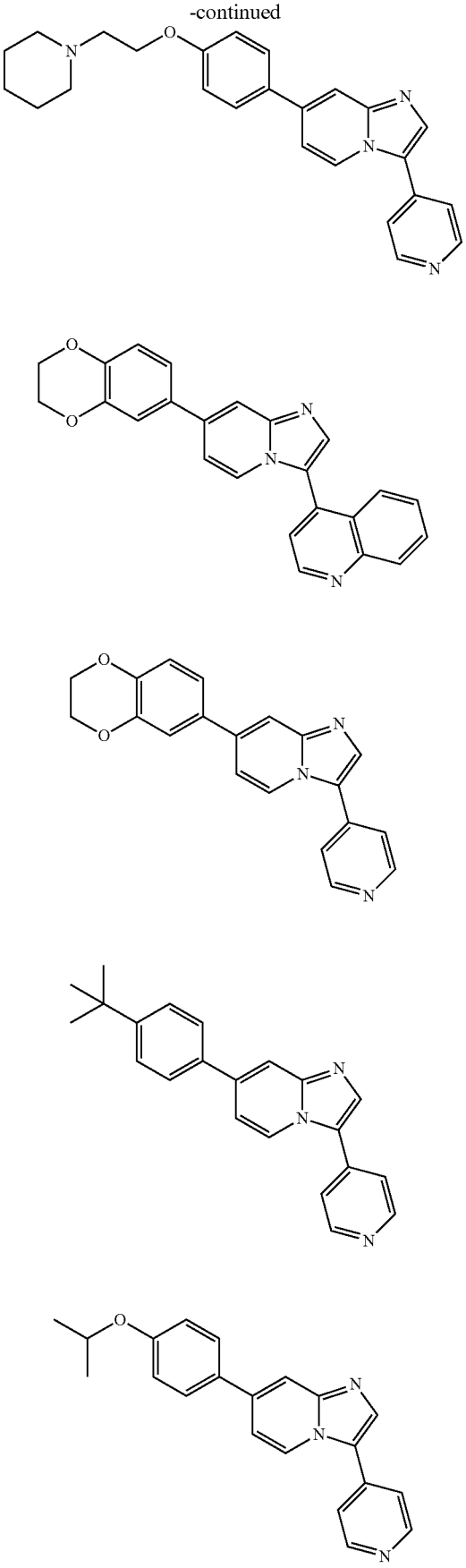

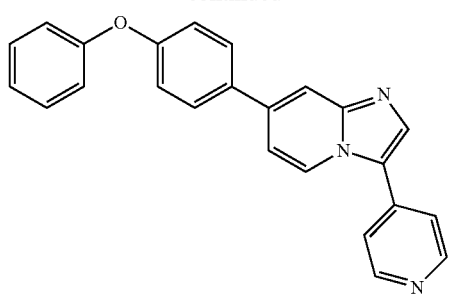
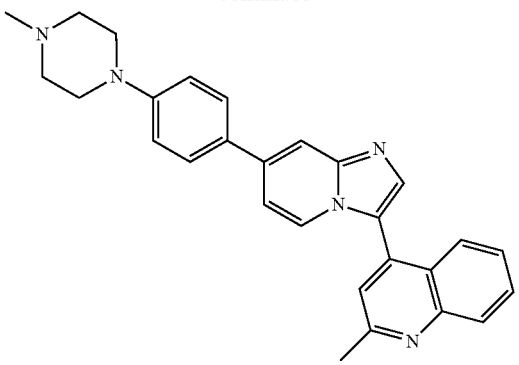 [SMILES: Cc1cc(-c2cnc3cc(-c4ccc(N5CCN(C)CC5)cc4)ccn23)c2ccccc2n1]
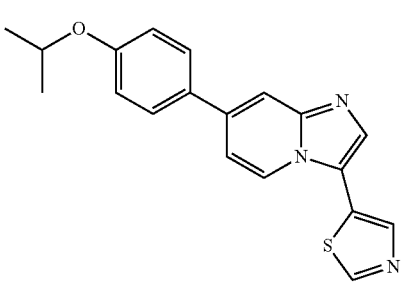
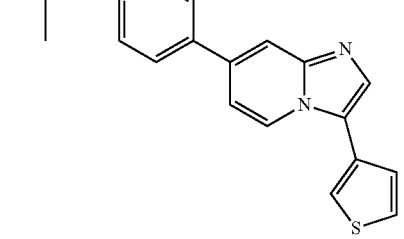
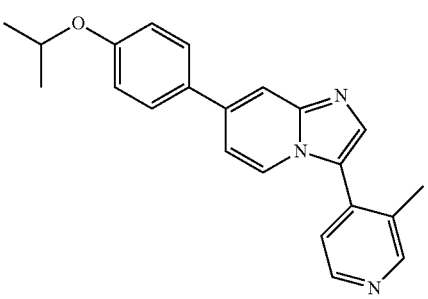 [SMILES: Cc1cnccc1-c1cnc2cc(-c3ccc(OC(C)C)cc3)ccn12]
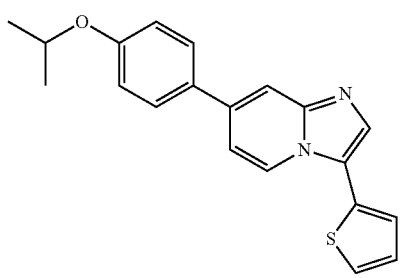

-continued
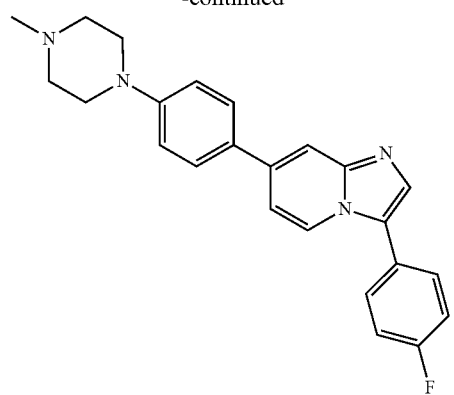
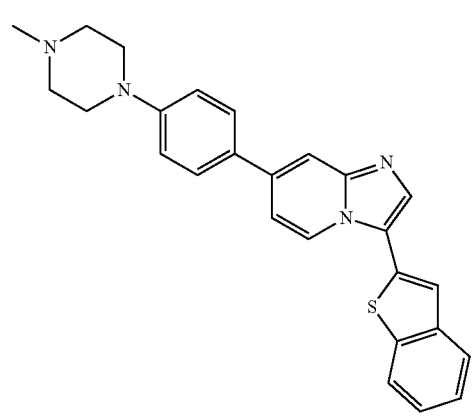
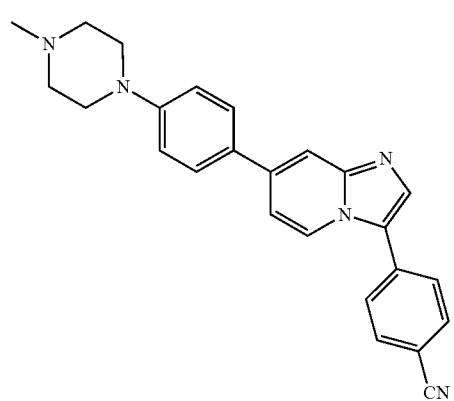 [SMILES: CN1CCN(c2ccc(-c3ccn4c(-c5ccc(C#N)cc5)cnc4c3)cc2)CC1]
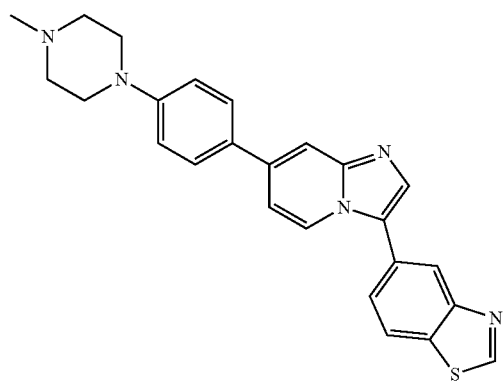
-continued
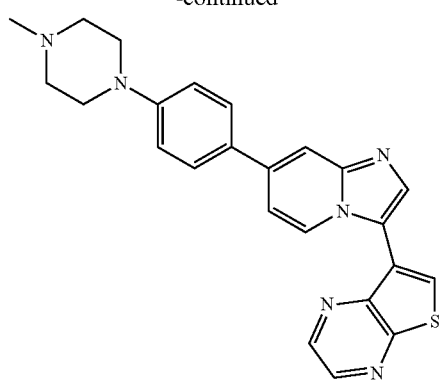
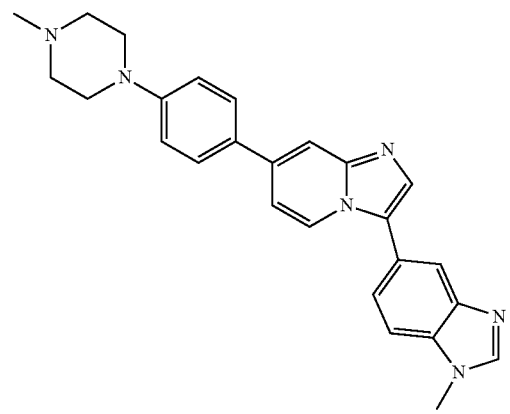
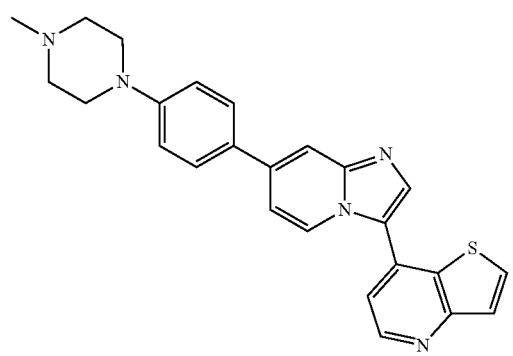 [SMILES: CN1CCN(c2ccc(-c3ccn4c(-c5ccnc6ccsc56)cnc4c3)cc2)CC1]
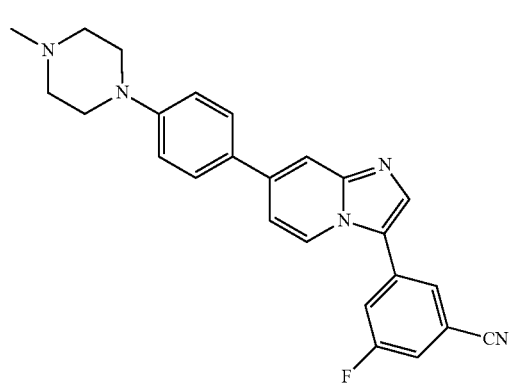 [SMILES: CN1CCN(c2ccc(-c3ccn4c(-c5cc(F)cc(C#N)c5)cnc4c3)cc2)CC1]

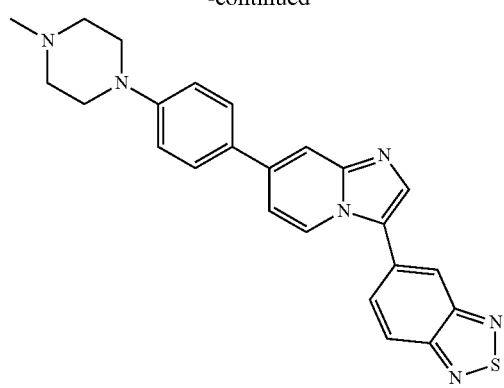
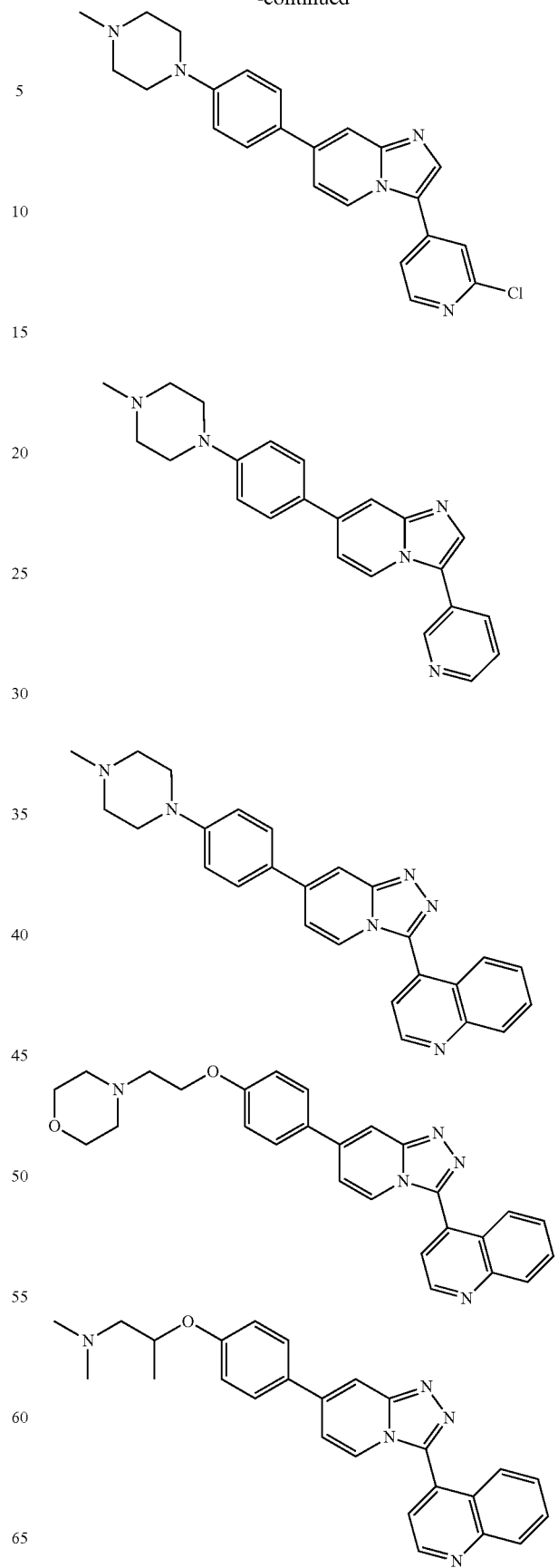

47
-continued
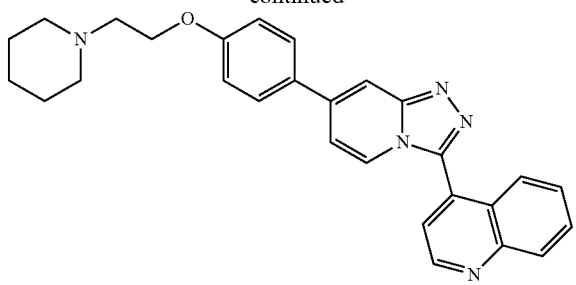
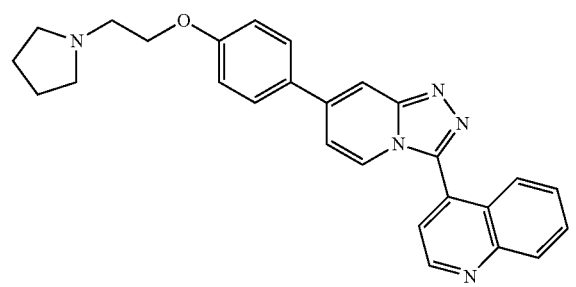 [SMILES: c1ccc2c(-c3nnc4cc(-c5ccc(OCCN6CCCC6)cc5)ccn34)ccnc2c1]
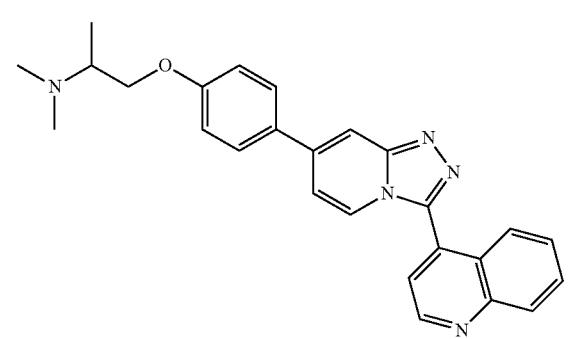 [SMILES: CC(COc1ccc(-c2ccn3c(-c4ccnc5ccccc45)nnc3c2)cc1)N(C)C]
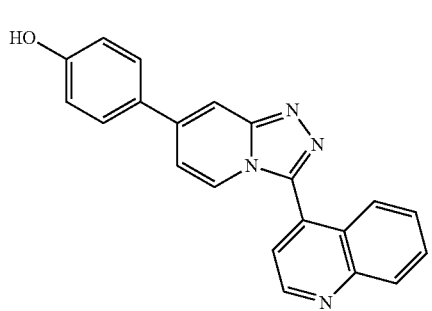 [SMILES: Oc1ccc(-c2ccn3c(-c4ccnc5ccccc45)nnc3c2)cc1]
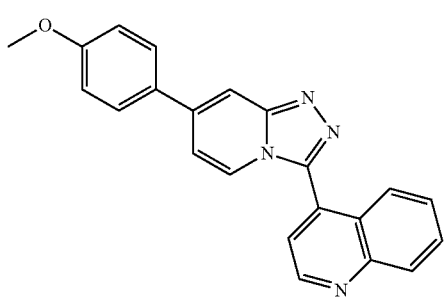 [SMILES: COc1ccc(-c2ccn3c(-c4ccnc5ccccc45)nnc3c2)cc1]
48
-continued
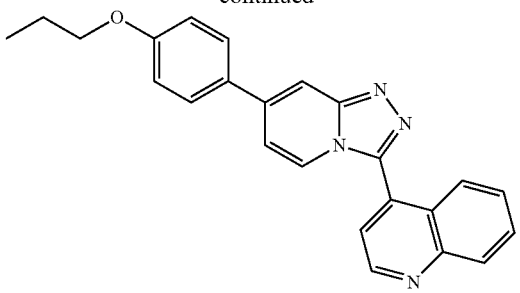
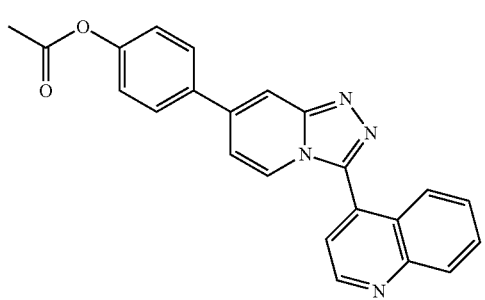 [SMILES: CC(=O)Oc1ccc(-c2ccn3c(-c4ccnc5ccccc45)nnc3c2)cc1]
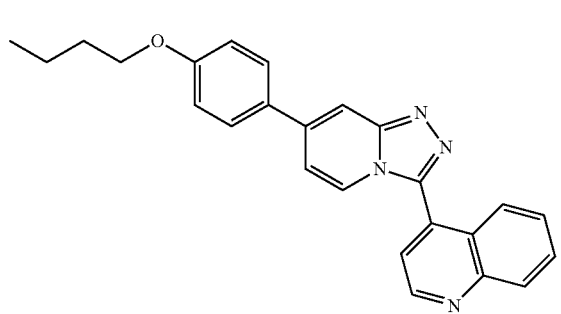 [SMILES: CCCCOc1ccc(-c2ccn3c(-c4ccnc5ccccc45)nnc3c2)cc1]
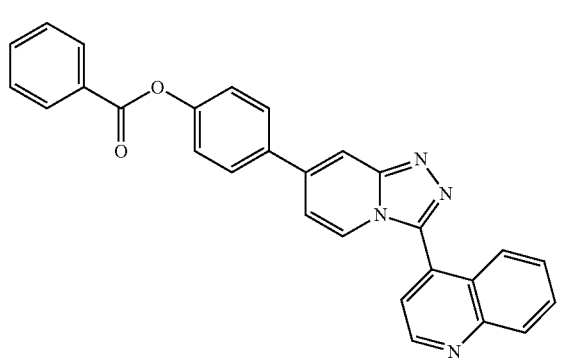 [SMILES: O=C(Oc1ccc(-c2ccn3c(-c4ccnc5ccccc45)nnc3c2)cc1)c1ccccc1]

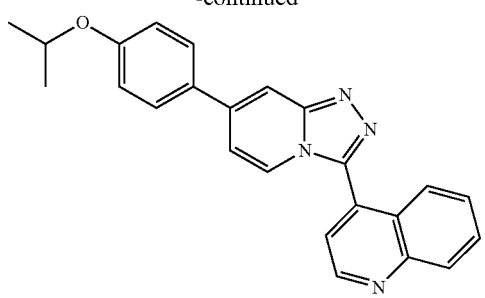
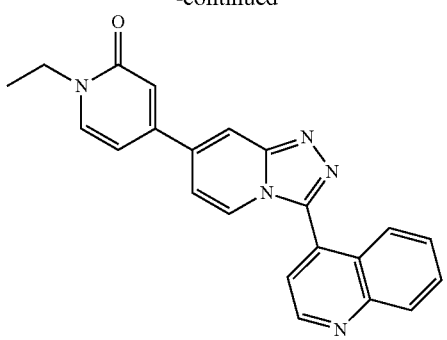
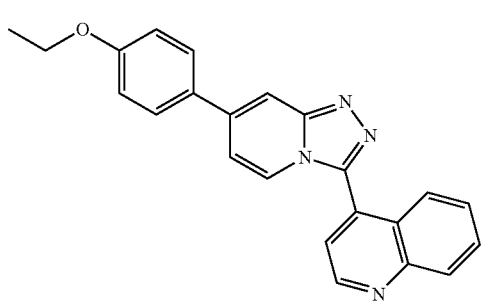 [SMILES: CCOc1ccc(-c2ccn3c(-c4ccnc5ccccc45)nnc3c2)cc1]
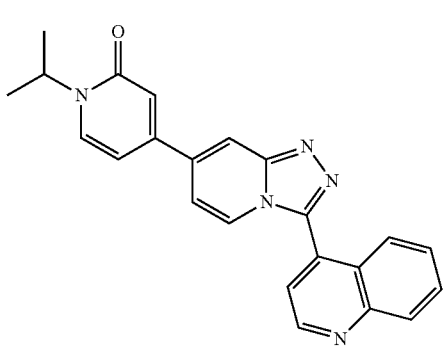
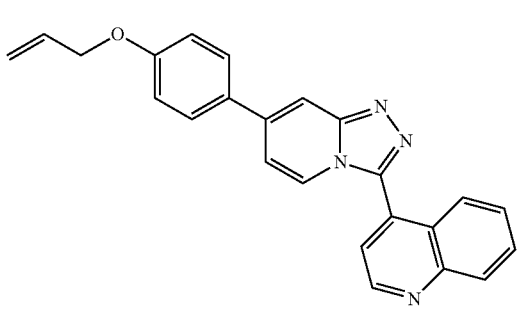 [SMILES: C=CCOc1ccc(-c2ccn3c(-c4ccnc5ccccc45)nnc3c2)cc1]
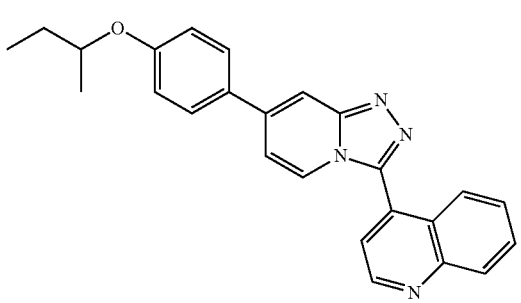 [SMILES: CCC(C)Oc1ccc(-c2ccn3c(-c4ccnc5ccccc45)nnc3c2)cc1]
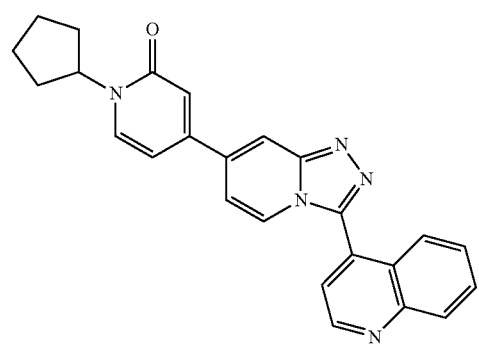 [SMILES: O=c1cc(-c2ccn3c(-c4ccnc5ccccc45)nnc3c2)ccn1C1CCCC1]
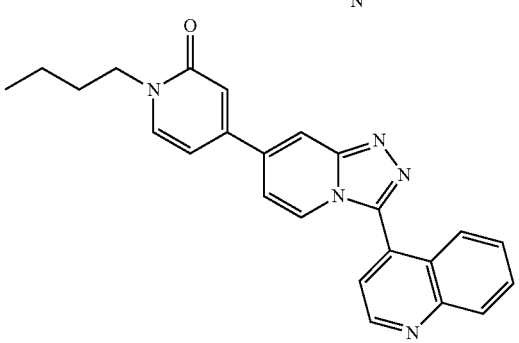
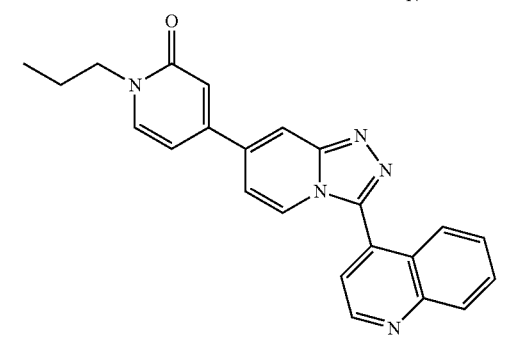

In yet other aspects, the invention relates to compounds having a structure represented by formula (I):

$$R_1 \underset{R_3}{\overset{Cy}{\diagdown}} \underset{Y_2}{\overset{Y_3}{\diagdown}} \underset{Y_1}{\overset{X_1}{\diagdown}} \underset{X_4}{\overset{R_4}{\diagdown}} \underset{X_3}{\overset{X_2}{\diagdown}} \underset{W}{\overset{D}{\diagdown}} \underset{R_2}{\overset{Z}{\diagdown}};$$

wherein:
$X_1$ is N, O, or $CR_1$;
$X_2$, and $X_4$ are independently N or $CR_1$;
$X_3$ is C or N;
$Y_1$, $Y_2$, and $Y_3$ are independently N or $CR_1$;
D is C or N;
W is N or O;
$W_1$ is N, O or C;
Cy is optionally substituted with one or more $R_1$, and is selected from $C_3$-$C_{12}$ cycloalkyl or $C_3$-$C_{12}$ cycloalkenyl or aryl or heteroaryl or $C_3$-$C_{12}$ heterocycloalkyl or $C_3$-$C_{12}$ heterocycloalkenyl or 3-8 membered ring comprising C, O, S, and/or N.

$R_1$-$R_4$ are independently selected from hydrogen, halogen, $C_{1-10}$ alkyl, $C_{3-10}$ cycloalkyl, $OC_{1-10}$ alkyl (which may contain a $C_{3-8}$ membered ring containing C, O, S or N, optionally substituted with one or more $R^4$), $NR_1C_{1-10}$ alkyl (which may contain a $C_{3-8}$ membered ring containing C, O, S or N, optionally substituted with one or more $R^4$), CN or $CF_3$;
Z is optionally substituted with one or more $R_1$, and is selected from $C_3$-$C_{12}$ cycloalkyl or $C_3$-$C_{12}$ cycloalkenyl or aryl or heteroaryl or $C_3$-$C_{12}$ heterocycloalkyl or $C_3$-$C_{12}$ heterocycloalkenyl or 3-8 membered ring comprising C, O, S, and/or N.

Also disclosed are compounds wherein, above, is wherein $A_1$ is independently O, $CR_1R_2$ or NH or $NR_1$ or $NR_1R_2$, or can join with another $A_1$ to form $C_3$-$C_{12}$ cycloalkyl or $C_3$-$C_{12}$ cycloalkenyl or aryl or heteroaryl or $C_3$-$C_{12}$ heterocycloalkyl or $C_3$-$C_{12}$ heterocycloalkenyl or 3-8 membered ring comprising C, O, S, and/or N.

Also disclosed are compounds wherein:

(I)

wherein:
$X_1$ is N, O, or $CR_1$;
$X_2$, and $X_4$ are independently N or $CR_1$;
$X_3$ is C or N;
$Y_1$, $Y_2$, and $Y_3$ are independently N or $CR_1$;
Cy is a bond, or forms a ring that is optionally substituted with one or more $R_1$, and is selected from $C_3$-$C_{12}$ cycloalkyl or $C_3$-$C_{12}$ cycloalkenyl or aryl or heteroaryl or $C_3$-$C_{12}$ heterocycloalkyl or $C_3$-$C_{12}$ heterocycloalkenyl or 3-8 membered ring comprising C, O, S, and/or N.
$R_1$-$R_4$ are independently selected from hydrogen, halogen, $C_{1-10}$ alkyl, $C_{3-10}$ cycloalkyl, $OC_{1-10}$ alkyl (which may contain a $C_{3-8}$ membered ring containing C, O, S or N, optionally substituted with one or more $R^4$), $NR_1C_{1-10}$ alkyl (which may contain a $C_{3-8}$ membered ring containing C, O, S or N, optionally substituted with one or more $R^4$), CN or $CF_3$;

Z is optionally substituted with one or more $R_1$, and is selected from $C_3$-$C_{12}$ cycloalkyl or $C_3$-$C_{12}$ cycloalkenyl or aryl or heteroaryl or $C_3$-$C_{12}$ heterocycloalkyl or $C_3$-$C_{12}$ heterocycloalkenyl or 3-8 membered ring comprising C, O, S, and/or N.

In one aspect, the invention relates to compounds having a structure represented by formula (I):

(I)

wherein:
$X_1$, $X_2$, $X_3$ and $X_4$ are independently N or $CR_1$;
X is N, O, or $CR_1$;
$X_3$ is C or N;
$Y_1$, $Y_2$, and $Y_3$ are independently N or $CR_1$;
$R_1$-$R_4$ are independently selected from hydrogen, halogen, $C_{1-10}$ alkyl, $C_{3-10}$ cycloalkyl, $OC_{1-10}$ alkyl (which may contain a $C_{3-8}$ membered ring containing C, O, S or N, optionally substituted with one or more $R^4$), CN or $CF_3$;
Z is optionally substituted with one or more $R_1$, and is selected from $C_3$-$C_{12}$ cycloalkyl or $C_3$-$C_{12}$ cycloalkenyl or aryl or heteroaryl or $C_3$-$C_{12}$ heterocycloalkyl or $C_3$-$C_{12}$ heterocycloalkenyl or 3-8 membered ring comprising C, O, S, and/or N.

Also disclosed are compounds of the following formula:

wherein the variables are defined above.
Also disclosed are compounds of the following formula:

wherein
(i) $X_1$ is O, $X_2$ is N, and X, $X_3$, $X_4$, $Y_1$, $Y_2$, and $Y_3$ are independently C or $CR_1$;
(ii) $X_1$ is O, $X_2$ is N, $Y_1$ is N, and X, $X_3$, $X_4$, $Y_2$, and $Y_3$ are independently C or $CR_1$;
(iii) $X_1$ is N, $X_4$ is N, and $X_2$, $X_3$, $X_4$, $Y_1$, $Y_2$, and $Y_3$ are independently C or $CR_1$;
(iv) $X_1$ is N, $X_2$ is N, $Y_1$ is N, and X, $X_3$, $X_4$, $Y_2$, and $Y_3$ are independently C or $CR_1$;
(v) $X_1$ is N, $X_2$ is N, $Y_2$ is N, and X, $X_3$, $X_4$, $Y_2$, and $Y_3$ are independently C or $CR_1$; or
(vi) $X_1$ is N, $X_3$ is N, and $X_2$, $X_3$, $X_4$, $Y_1$, $Y_2$, and $Y_3$ are independently C or $CR_1$;
and wherein the remaining variables are defined above.

Also disclosed are compounds of the following formula:

wherein the variables are defined above.
Also disclosed are compounds of the following formula:

wherein the variables are defined above.
Also disclosed are compounds of the following formula:

wherein the variables are defined above.
Also disclosed are compounds of the following formula:

wherein the variables are defined above.

Also disclosed are compounds of the following formula:

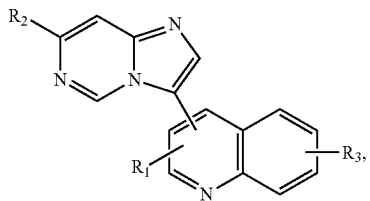

wherein the variables are defined above.

Also disclosed are compounds of the following formula:

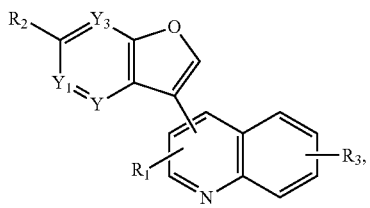

wherein the variables are defined above.

Also disclosed are compounds of the following formula:

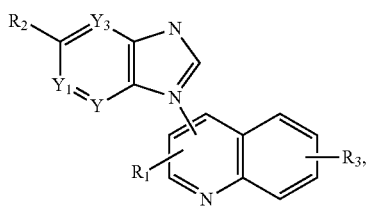

wherein the variables are defined above.

Also disclosed are the following compounds:

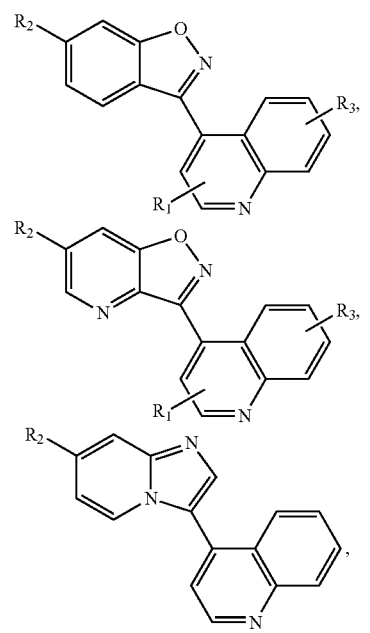

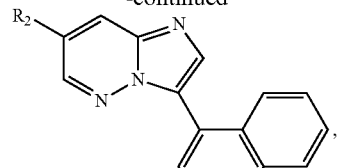

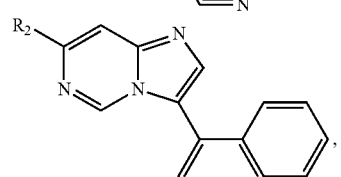

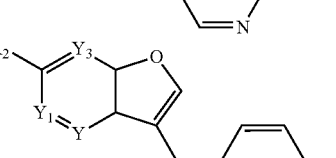

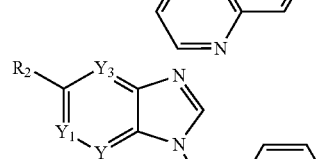, and

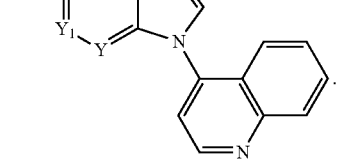.

The compounds disclosed herein can include all salt forms, for example, salts of both basic groups, inter alia, amines, as well as salts of acidic groups, inter alia, carboxylic acids. The following are non-limiting examples of anions that can form salts with protonated basic groups: chloride, bromide, iodide, sulfate, bisulfate, carbonate, bicarbonate, phosphate, formate, acetate, propionate, butyrate, pyruvate, lactate, oxalate, malonate, maleate, succinate, tartrate, fumarate, citrate, and the like. The following are non-limiting examples of cations that can form salts of acidic groups: ammonium, sodium, lithium, potassium, calcium, magnesium, bismuth, lysine, and the like.

The analogs (compounds) of the present disclosure are arranged into several categories to assist the formulator in applying a rational synthetic strategy for the preparation of analogs which are not expressly exampled herein. The arrangement into categories does not imply increased or decreased efficacy for any of the compositions of matter described herein.

C. Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids" includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention can comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require BMP inhibition, an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

Further disclosed herein are pharmaceutical compositions comprising one or more of the disclosed BMP inhibitors and a pharmaceutically acceptable carrier. Accordingly, the pharmaceutical compositions of the present invention include those that contain one or more other active ingredients, in addition to a compound of the present invention.

The above combinations include combinations of a disclosed compound not only with one other active compound, but also with two or more other active compounds. Likewise, disclosed compounds may be used in combination with other drugs that are used in the prevention, treatment, control, amelioration, or reduction of risk of the diseases or conditions for which disclosed compounds are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient can be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent may be coadministered, either in concomitant therapy or in a fixed combination.

In one aspect, the compound can be employed in combination with a second compound with the known side effect of modulating BMP signaling pathways.

In the treatment of conditions which require inhibition of BMP, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15. 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In one aspect, the invention relates to pharmaceutical compositions comprising a compound having a structure represented by the following formula (I):

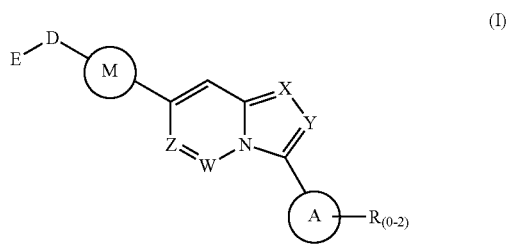

wherein:
W, X, Y, and Z are independently N or CH;
A is substituted or unsubstituted and selected from cycloalkyl, heterocycloalkyl, aryl or heteroaryl;
R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;
M is substituted or unsubstituted and is selected from aryl or heteroaryl;
D is selected from a bond, O, $CR_1R_2$ or NH or $NR_1$ or $NR_1R_2$ or $S(O)_{0-2}R_1R_2$;
E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;
$R_1$ is selected from H, alkyl, aryl, heteraryl, $COR_1$; and $R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S.

D. Methods of Using the Compounds and Compositions

1. Treatment Methods

BMPs and TGF-β signaling pathways are essential to normal organogenesis and pattern formation, as well as the normal and pathological remodeling of mature tissues. Defects in the BMP signaling pathway are implicated in a number of congenital and acquired disease processes, including Hereditary Hemorrhagic Telangectasia syndrome, Primary Pulmonary Hypertension, Juvenile Familial Polyposis, as well as sporadic renal cell and prostate carcinomas. It has been suggested that in certain disease states associated with defective signaling components, attenuated BMP signaling might be a cause, while our findings have suggested that in some contexts excess BMP signaling might be pathogenic (Waite et al. Nat. Rev. Genet. 4:763-773, 2005; Yu et. J. Biol. Chem. 280:24443-24450, 2003). The ability to modulate BMP signaling experimentally would provide a means for investigating therapy, and for determining the root causes of these conditions.

A. Treatment of Anemia, Including Iron Deficiency and Anemia of Chronic Disease

For a review, see Weiss et al. N. Engl. J. Med. 352:1011-1023, 2005. Anemia of inflammation (also called anemia of chronic disease) can be seen in patients with chronic infections, autoimmune diseases (such as systemic lupus erythematosis and rheumatoid arthritis, and Castleman's disease), inflammatory bowel disease, cancers (including multiple myeloma), and renal failure. Anemia of inflammation is often caused by maladaptive expression of the peptide hormone hepcidin. Hepcidin causes degradation of ferroportin, a critical protein that enables transport of iron from intracellular stores in macrophages and from intestinal epithelial cells. Many patients with renal failure have a combination of erythropoietin deficiency and excess hepcidin expression. BMP signaling induces expression of hepcidin and inhibiting hepcidin expression with BMP antagonists increases iron levels. Compounds as described herein can be used to treat anemia due to chronic disease or inflammation and associated hyperhepcidinemic states.

The inflammatory cytokine IL-6 is thought to be the principal cause of elevated hepcidin expression in inflammatory states, based upon the elevation of IL-6 in anemia of inflammation of diverse etiologies, the effects of chronic IL-6 administration in vivo, and the protection against anemia in rodents deficient in IL-6 (Weiss et al. N. Engl. J. Med. 352:1011-1023, 2005). It has been shown that stimulating hepatoma cell lines with IL-6 induces hepcidin expression, while treatment with a BMP antagonist abrogates IL-6-induced hepcidin expression (Yu et al. Nat. Chem. Biol. 4:33-41, 2008). Moreover, we have found that BMP antagonists can inhibit hepcidin expression induced by injection of pathogenic bacteria in vivo (see Example 8). It has also been shown that systemic iron administration in mice and zebrafish rapidly activates BMP-responsive-SMADs and hepcidin expression in the liver, and that BMP antagonism effectively blocks these responses (Yu et al. Nat. Chem. Biol. 4:33-41, 2008). The functional importance of BMP signaling in iron regulation is supported by our finding that BMP antagonists can inhibit hepcidin expression and raise serum iron levels in vivo (see Example 7). Taken together these data suggest that iron- and inflammation-mediated regulation of hepcidin and circulating iron levels require BMP signaling. Compounds as described herein may be used to alter iron availability in diverse circumstances for therapeutic benefit.

Compounds as described herein may be used in anemic states to (i) augment the efficacy of dietary iron or oral iron supplementation (which is safer than intravenous administration of iron) to increase serum iron concentrations; (ii) augment build up of hemoglobin in the blood in anticipation of surgery or to enable blood donation for self in anticipation of surgery; and (iii) enhance the efficacy of erythropoietin and its relatives, thereby enabling lower doses of erythropoietin to be administered for anemia while minimizing known toxicities and side effects of erythropoietin (i.e., hypertension, cardiovascular events, and tumor growth).

B. Treatment of Fibrodysplasia Ossificans Progressiva (FOP)

FOP is caused by the presence of a constitutively-active mutant form of ALK2 in affected individuals (Shore et al. Nat. Genet. 38:525-527, 2006). A specific inhibitor of BMP signaling such as a compound as described herein can be used to prevent excessive bone formation in response to trauma, musculoskeletal stress or inflammation. Such a compound could also be used to aid in regression of pathologic bone. The BMP inhibitor could be administered systemically or locally to concentrate or limit effects to areas of trauma or inflammation.

A BMP inhibitor as described herein may be used as chronic therapy to suppress spontaneous bone formation in individuals who are highly susceptible. Transient therapy may be used to prevent abnormal bone formation in FOP individuals who develop osteomas or pathologic bone most frequently in association with trauma by administration before, during, or even after the traumatic incident. Transient therapy with BMP inhibitors as described herein could be used before, during or immediately after necessary or emergent medical or surgical procedures (and even important immunizations and tooth extractions) in individuals with FOP, to prevent pathologic calcification. Combination therapy with other bone inhibiting agents, immune modulatory or anti-inflammatory drugs (such as NSA/Ds, steroids, cyclosporine, cyclophosphamide, azathioprine, methotrexate, rituximab, etanercept, or similar drugs) may increase the effectiveness of BMP antagonists in inhibiting heterotopic bone formation in this disorder.

A mouse model of FOP has been developed in which expression of a constitutively-active mutant form of ALK2 is induced by injecting the popliteal fossa of a genetically-modified mouse with an adenovirus directing expression of Cre recombinase. This model reproduces the ectopic calcification and disability seen in FOP patients. Twice daily administration of compound 13 (3 mg/kg ip) prevented the ectopic calcification and disability (see Example 10).

C. Treatment of Cancers

Excessive BMP signaling, which could arise due to over-expression of BMPs, or, paradoxically, as a result of loss of BMP type II receptor expression, may contribute to the oncogenesis, growth or metastasis of certain solid tumors, including breast, prostate carcinomas, bone, lung, and renal cell carcinomas (Yu et al. J. Biol. Chem. 280:24443-24450, 2008; Waite et al. Nat. Rev. Genet. 4:763-773, 2003; Alarmo et al. Genes, Chromosomes Cancer 45:411-419, 2006; Kim et al. Cancer Res. 60:2840-2844, 2000; Kim et al. Clin. Cancer Res. 9:6046-6051, 2003; Kim et al. Oncogene 23:7651-7659, 2004). If increased BMP activity associated with BMP over-expression or BMP type II receptor deficiency contributes to the pathogenesis of disease, then inhibiting BMP signaling activity using compounds as described herein at the level of BMP type I receptors (downstream of both ligands and type II receptor) could be an effective means of normalizing BMP signaling activity and potentially inhibiting tumor growth or metastasis.

Compounds as described herein can be used to slow or arrest the growth or metastasis of such tumor cells (as well as other tumor constituent cell types) for clinical benefit, either as adjunctive or primary chemotherapy. Also, BMP inhibitors as described herein may be used to interfere with the bone metastatic properties of certain types of cancers (e.g., adenocarcinoma, such as prostate and breast carcinomas). In addition, compounds as described herein can be used to inhibit osteoblastic activity in tumors that either form bone or are bone-derived, such as osteosarcomas (as adjunctive or primary chemotherapy). Further, compounds as described herein can be used to inhibit osteoclastic activity (also regulated by BMPs through the action of its target gene RANKL), which is pathologically increased in conditions such as multiple myeloma and other bone-targeted tumors. Application of BMP inhibitors in these conditions may reduce the presence of osteolytic lesions and bone fractures due to tumor involvement.

D. Immune Modulation Via BMP Antagonists

BMPs have been reported to attenuate the inflammatory or immune response (Choi et al. Nat. Immunol. 7:1057-1065, 2006; Kersten et al. BMC Immunol. 6:9, 2005), which can impair an individual's ability to fight infections (i.e., viral, bacterial, fungal, parasitic, or tuberculosis). Inhibitors of BMP signaling as described herein may thus augment the inflammatory or immune response enabling individuals to clear infections more rapidly.

Lymphocytes and other immune cells express BMP receptors on their cell surfaces, and there is growing evidence that BMPs regulate the development and maturation of various humoral and cellular immunologic compartments, and regulate humoral and cellular immune responses in mature organisms. The effects of BMP signals on immune cells are likely to be context-specific, as is commonly known for the effects of numerous cytokines of immunologic importance, and thus whether they augment or diminish the development or function of particular lymphocyte populations must be empirically determined. BMP antagonism using compounds as described herein may be an effective strategy for intentionally biasing the development of cellular, innate, or humoral immune compartments for therapy, or a strategy for the therapeutic deviation of immune responses in mature immune systems. These strategies may target inborn disorders of cellular, innate, or humoral immunity, or target disorders in which immune responses are inappropriately weak (e.g., as an adjuvant to promote successful antigen sensitization when immunization is difficult or ineffective by other means), or target disorders in which immune responses are excessive or inappropriate (e.g., autoimmunity and autosensitization). BMP antagonists as described herein may also be effective in some contexts for the intentional induction of immune tolerance (i.e., in allotransplantation or autoimmunity).

E. Treatment of Pathologic Bone Formation

Compounds as described herein can be used to ameliorate pathologic bone formation/bone fusion in inflammatory disorders, such as ankylosing spondylitis or other "seronegative" spondyloarthropathies, in which autoimmunity and inflammation in such disorders appear to stimulate bone formation. One application of the compounds would be to prevent excess bone formation after joint surgery, particularly in patients with ankylosing spondylitis or rheumatoid arthritis. Compounds as described herein can also be used to prevent calcinosis (dystrophic soft-tissue calcification) in diseases such as systemic lupus erythematosus, scleroderma, or dermatomyositis.

Blunt traumatic injury to muscles can cause abnormal bone formation within muscle in certain individuals, resulting in a disorder called myositis ossificans traumatica (Cushner et al. Orthop. Rev. 21:1319-1326, 1992.). Head trauma and burn injury can also induce heterotopic bone formation markedly impairing patient rehabilitation and recovery. Treatment with a BMP inhibitor as described herein, optionally in addition to anti-inflammatory medications usually prescribed for such a condition (eg. non-steroidal anti-inflammatory drugs such as indomethacin or ibuprofen) may help to prevent the formation of pathologic bone in predisposed individuals, or to help lessen or regress lesions in individuals recently or remotely affected. Very rarely other muscles have been described to develop ossification in the presence of injury or trauma, including heart muscle, and similar treatment with a BMP inhibitor as described herein could be helpful in those circumstances.

F. Treatment of Ectopic or Maladaptive Bone Formation

BMP signals and their transcriptional targets are implicated in intimal and medial vascular remodeling and calcification in Monckeberg's vascular calcification disease and in atheromatous vascular disease (Bostrom et al. J. Clin. Invest. 91:1800-1809, 1993; Tyson et al. Arterioscler. Thromb. Vasc. Biol. 23:489-494, 2003). BMPs and BMP-induced osteodifferentation are also implicated in cardiac valvular calcification. Native cardiac valves can calcify particularly when they are already abnormal. A classic example is bicuspid aortic valve—these valves typically become calcified leading to stenosis. Patients with calcific aortic valve stenosis often require cardiac surgery for valve replacement. Abnormal calcification can adversely affect the function of prosthetic vascular grafts or cardiac valves. For example, prosthetic heart valves become calcified leading to narrowing and often leakage.

Compounds as described herein can be used to inhibit vascular or valvular calcific disease alone or in combination with atheromatous disease, renal disease, renal osteodystrophy or parathyroid disease.

Compounds as described herein can be used to inhibit calcification of prosthetic vascular or valvular materials by systemic or local administration or direct incorporation into prosthesis materials or other implants (e.g., in admixture with a polymer that coats or constitutes all or part of the implant or prosthesis).

In some instances, it is desired to delay fracture healing following a bone fracture, or to purposely inhibit fracture healing in certain locations to prevent impairment of function by maladaptive bone formation. For example, if a fracture occurs and for medical or practical reasons surgery cannot be performed immediately, fracture healing may be temporarily "suspended" by use of a BMP inhibitor as described herein, until definitive surgery or manipulation can be performed. This could prevent the need for subsequent intentional re-fracture in order to ensure correct apposition of bone fragments, for example. It is expected that upon stopping a BMP inhibitor normal fracture healing processes would ensue if the period of treatment is relatively short. In other cases, any amount of novel bone growth might impair function, such as when fracture affects a joint directly. In these cases, global or local inhibition of BMP activity (by systemic or local delivery of a BMP antagonist as described herein via diffusion from a local implant or matrix) may be used to inhibit fracture healing or prevent fracture calluses at the critical areas.

G. Treatment of Skin Diseases

Expansion of cultured keratinocytes—In vitro, BMPs inhibit keratinocyte proliferation and promote differentiation (reviewed in Botchkarev et al. Differentiation 72:512-526, 2004). In patients in need of skin grafting (eg. after burns), skin grafts are made from cultured keratinocytes. The keratinocytes may be derived from other animals (xenografts), but these are only temporary as they will be rejected by the immune system. Keratinocytes can be derived from the patient themselves and can be grown into sheets of cells in the laboratory (cultured epithelial autografts). The patient will not reject keratinocytes derived from his/her own body. Addition of BMP antagonists as described herein to keratinocyte cultures can be used to facilitate keratinocyte proliferation enabling patients to receive grafts sooner.

Improved epithelialization—BMP6 is highly expressed in skin injury, and high levels of BMP6 are detected in chronic human wounds of different etiologies (Kaiser et al. J. Invest. Dermatol. 111:1145-1152, 1998). In mice overexpressing BMP6 in their skin, reepithelialization and healing skin wounds were significantly delayed (Kaiser et al. J. Invest. Dermatol. 111:1145-1152, 1998). Improved epithelialization can reduce scar formation. Topical or systemic administration of BMP antagonists as described herein can be used to augment epithelialization of skin wounds, for example, in the treatment of pressure ulcers (bed sores) or non-healing or poorly-healing skin ulcers (e.g., in patients with peripheral vascular disease, diabetes mellitus, venous incompetence). Compounds would also be expected to decrease scar formation.

Promotion of hair growth—Growth of hair follicles on the scalp is cyclic with three phases: anagen (the growth phase), catagen (the involutional phase), and telogen (resting phase). Recent evidence suggests that BMP signals delay the transition from telogen to anagen (Plikus et al. Nature 451:340-344, 2008). Inhibition of BMP signaling using compounds as described herein can shorten the telogen phase and increase the number of follicles in the anagen phase. Compounds as described herein can be used to treat circumstances wherein hair follicles are insufficient or when hairs are being lost more frequently than they are grown. These circumstances include androgenetic alopecia (male pattern balding), alopecia greata, and telogen effluvium.

Treatment of psoriasis—Psoriasis is an inflammatory skin disorder which sometimes occurs following skin trauma and the ensuing repair and inflammation (Koebner phenomenon). BMPs may participate in repair and inflammatory mechanisms that cause psoriasis, since over-expression of BMP6 in the skin of mice leads to skin lesions similar to those seen in patients with psoriasis (Blessing et al. J. Cell. Biol. 135:227-239, 1996). Compounds as described herein may be administered topically or systemically to treat established psoriasis or prevent its development after skin injury.

Treatment of corneal scarring—BMP6 expression is associated with conjunctival scarring (Andreev et al. Exp. Eye Res. 83:1162-1170, 2006). Compounds as described herein can be used to prevent or treat corneal scarring and the resulting blindness.

H. Treatment of Systemic Hypertension

Infusion of BMP4 induces systemic hypertension in mice (Miriyala et al. Circulation 113:2818-2825, 2006). Vascular smooth muscle cells express a variety of BMP ligands. BMPs increase the expression of voltage gated potassium channels and thereby increase constriction of vascular smooth muscle (Fantozzi et al. Am. J. Physiol. Lung Cell. Mol. Physiol. 291:L993-1004, 2006). Compounds as described herein that inhibit BMP signaling can be used to reduce blood pressure. Sustained reduction of blood pressure in patients with hypertension would be expected to prevent myocardial infarction, congestive heart failure, cerebrovascular accidents, and renal failure. BMP inhibitors as described herein can be used to target the hypertension in specific vascular beds, such as in pulmonary hypertension via local delivery (e.g., via aerosol).

I. Treatment of Pulmonary Hypertension

BMP signaling contributes to the pathogenesis of pulmonary hypertension. For example, mice with decreased BMP4 levels are protected from the pulmonary hypertension and pulmonary vascular remodeling induced by breathing low oxygen concentrations for prolonged periods (Frank et al. Circ. Res. 97:496-504, 2005). Moreover, mutations in the gene encoding the type II BMP receptor (BMPRII) are frequently found in patients with sporadic and familial pulmonary arterial hypertension. It might be anticipated that decreased BMP signaling might cause pulmonary hypertension. However, Yu and colleagues (Yu et al. J. Biol. Chem. 280:24443-24450, 2008) reported that BMPRII deficiency paradoxically increases BMP signaling by subsets of BMP ligands, and thus increased BMP signaling using compounds as described herein may actually contribute to the development of pulmonary hypertension.

Compounds as described herein can used to prevent the development of pulmonary arterial hypertension in patients at risk for the disease (e.g., patients with BMPRII mutations) or to treat patients with idiopathic or acquired pulmonary arterial hypertension. Decreased pulmonary hypertension in individuals treated with the compounds described herein would be expected to decrease shortness of breath, right ventricular hypertrophy, and right ventricular failure.

J. Treatment of Ventricular Hypertrophy

BMP-10 levels are increased in the hypertrophied ventricles of rats with hypertension, and this BMP ligand induces hypertrophy in cultured neonatal rat ventricular myocytes (Nakano et al. Am. J. Physiol. Heart. Circ. Physiol. 293:H3396-3403, 2007). Inhibition of BMP-10 signaling with compounds as described herein can to prevent/treat ventricular hypertrophy. Ventricular hypertrophy can lead to congestive heart failure due to diastolic dysfunction. Compounds described herein would be expected to prevent/treat congestive heart failure.

K. Treatment of Neurologic Disorders

Treatment of spinal cord injury and neuropathy—BMPs are potent inhibitors of axonal regeneration in the adult spinal cord after spinal cord injury (Matsuura et al. J. Neurochem. 2008). Expression of BMPs is reported to be elevated in oligodendrocytes and astrocytes around the injury site following spinal cord contusion. Intrathecal administration of noggin, a BMP inhibitor, led to enhanced locomotor activity and significant regrowth of the corticospinal tract after spinal cord contusion.

RGMa inhibits axonal growth and recovery after spinal cord injury, as well as synapse re-formation, effects which are blocked by an antibody directed against RGMa (Hata et al. J. Cell. Biol. 173:47-58, 2006; Kyoto et al. Brain Res. 1186:74-86, 2007). RGMa enhances BMP signaling (Babitt et al. J. Biol. Chem. 280:29820-29827, 2005) suggesting that BMP signaling may be responsible for preventing axonal growth and recovery.

Based on these considerations, compounds as described herein would be expected to increase axonal growth and recovery after spinal cord injury. Compounds as described herein would be expected to prevent/treat neuropathies associated with a wide spectrum of disorders including diabetes mellitus. Compounds as described herein would be expected to treat both the pain and motor dysfunction associated with neuropathies.

Treatment of neurologic disorders associated with central nervous system inflammation—BMP4 and 5 have been detected in multiple sclerosis and Creutzfeldt-Jakob disease lesions (Deininger et al. Acta Neuropathol. 90:76-79, 1995). BMPs have also been detected in mice with experimental autoimmune encephalomyelitis, an animal model of multiple sclerosis (Ara et al. J. Neurosci. Res. 86:125-135, 2008). Compounds as described herein may be used to prevent or treat multiple sclerosis as well as other neurologic disorders associated with central nervous system inflammation, or maladaptive injury repair processes mediated by BMP signals.

Treatment of dementias—Inhibitors of BMP signaling can promote neurogenesis in mouse neural precursor cells (Koike et al. J. Biol. Chem. 282:15843-15850, 2007). Compounds as described herein can be used to augment neurogenesis in a variety of neurologic disorders associated with accelerated loss of neurons including cerebrovascular accidents and Alzheimer's Disease, as well as other dementias.

Altering memory and learning—BMP signaling has an important role in the development and maintenance of neurons involved in memory and cognitive behavior. For example, mice deficient in the BMP antagonist, chordin, have enhanced spatial learning but less exploratory activity in a novel environment (Sun et al. J. Neurosci. 27:7740-7750, 2007). Compounds as described herein can be used to alter or prevent memory or learning, for example, inducing amnesia for anesthesia or in other situations likely to cause distress, or to prevent Post-Traumatic Stress Disorder.

L. Treatment of Atherosclerosis

Abundant evidence suggests that BMP ligands are pro-inflammatory and pro-atherogenic in the blood vessel wall (Chang et al. Circulation 116:1258-1266, 2007). Knocking-down expression of BMP4 decreased inflammatory signals, whereas knocking-down BMP antagonists (egfollistatin or noggin) increased inflammatory signals. Compounds as described herein can be used to reduce vascular inflammation associated with atherosclerosis, autoimmune disease, and other vasculitides. By decreasing atherosclerosis, it would be anticipated that compounds as described herein would decrease acute coronary syndromes (angina pectoris and heart attack), transient ischemic attacks, stroke, peripheral vascular disease, and other vascular ischemic events. Moreover, in so far as atherosclerosis contributes to the pathogenesis of aneurysm formation, compounds as described herein can be used to slow the progression of aneurysm formation decreasing the frequency of aneurismal structure and the requirement for vascular surgery.

As BMPs and many of the BMP-induced gene products that affect matrix remodeling are overexpressed in early atherosclerotic lesions, BMP signals may promote plaque formation and progression (Bostrom et al. J Clin Invest. 91: 1800-1809. 1993; Dhore et al. Arterioscler Thromb Vasc Biol. 21: 1998-2003. 2001). BMP signaling activity in the atheromatous plaque may thus represent a form of maladaptive injury-repair, or may contribute to inflammation. Over time, BMP signals may also induce resident or nascent vascular cell populations to differentiate into osteoblast-like cells, leading to intimal and medial calcification of vessels (Hruska et al. Circ Res. 97: 105-112. 2005). Calcific vascular disease, or arteriosclerosis, is associated with decreased vascular distensibility, and increased risk of cardiovascular events and mortality, and is particularly problematic when associated with underlying atherosclerotic disease (Bostrom et al. Crit Rev Eukaryot Gene Expr. 10: 151-158. 2000). Both atherosclerotic and calcific lesions may be amenable to regression, however, if signals which contribute to their progression can be intercepted (Sano et al. Circulation. 103: 2955-2960. 2001). In certain aspects, compound 13 or another inhibitor of BMP type I receptor activity may be used to limit the progression of atheromatous plaques and vascular calcification in vivo.

M. Propagation, Engraftment and Differentiation of Progenitor Cells Including Embryonic and Adult Stem Cells In Vitro and In Vivo BMP signals are crucial for regulating the differentiation and regeneration of precursor and stem cell populations, in some contexts and tissues preventing (while in other contexts directing) differentiation towards a lineage. Compounds as described herein can be used to (i) maintain a pluripotential state in stem cell or multipotent cell populations in vivo or in vitro; (ii) expand stem cell or multipotent cell populations in vivo or in vitro; (iii) direct differentiation of stem cell or multipotent cell populations in vivo or in vitro; (iv) manipulate or direct the differentiation of stem cell or multipotent cell populations in vivo or in vitro, either alone or in combination or in sequence with other treatments; and (v) modulate the de-differentiation of differentiated cell populations into multipotent or progenitor populations.

Numerous stem cell and precursor lineages require BMP signals in order to determine whether they will expand, differentiate towards specific tissue lineages, home in and integrate with particular tissue types, or undergo programmed cell death. Frequently BMP signals interact with signals provided by growth factors (bFGF, PDGF, VEGF, HBEGF, PlGF, and others), Sonic Hedgehog (SHH), notch, and Wnt signaling pathways to effect these changes (Okita et al. Curr. Stem Cell Res. Ther. 1:103-111, 2006). Compounds as described herein can be used to direct the differentiation of stem cells (e.g., embryonic stem cells) or tissue progenitor cells towards specific lineages for therapeutic application (Park et al. Development 131:2749-2762, 2004; Pashmforoush et al. Cell 117:373-386, 2004). Alternatively for certain cell populations, BMP inhibitors as described herein may be effective in preventing differentiation and promoting expansion, in order to produce sufficient numbers of cells to be effective for a clinical application. The exact combination of BMP antagonist and growth factor or signaling molecule may be highly specific to each cell and tissue type.

For example, certain embryonic stem cell lines require co-culture with leukemia inhibitory factor (LIF) to inhibit differentiation and maintain the pluripotency of certain cultured embryonic stem cell lines (Okita et al. Curr. Stem Cell Res. Ther. 1:103-111, 2006). Use of a BMP inhibitor as described herein may be used to maintain pluripotency in the absence of LIF. Other ES cell lines require coculture with a specific feeder cell layer in order to maintain pluripotency. Use of a BMP inhibitor as described herein, alone or in combination with other agents, may be effective in maintaining pluripotency when concerns of contamination with a feeder cell layer, or its DNA or protein components would complicate or prevent use of cells for human therapy.

In another example, in some circumstances antagonizing BMP signals with a protein such as noggin shortly before cessation of LIF in culture is able to induce differentiation into a cardiomyocyte lineage (Yuasa et al. Nat. Biotechnol. 23:607-611, 2005). Use of a pharmacologic BMP antagonist as described herein may achieve similar if not more potent effects. Such differentiated cells could be introduced into diseased myocardium therapeutically. Alternatively, such treatment may actually be more effective on engrafted precursor cells which have already homed in to diseased myocardium. Systemic therapy with a protein antagonist of BMP such as noggin would be prohibitively expensive and entail complicated dosing. Delivery of a BMP antagonist as described herein, systemically or locally, could bias the differentiation of such precursor cells into functioning cardiomyocytes in situ.

N. Application of Compounds with Varying Degrees of Selectivity: Compounds which Inhibit BMP Signaling Via Particular BMP Type I Receptors, or Compounds which Also Affect Signaling Via TGF-$\beta$, Activin, AMP Kinase, or VEGF Receptors ALK-specific antagonists—Dorsomorphin inhibits the activity of the BMP type I receptors, ALK2, ALK3, and ALK6. Dorsomorphin inhibits ALK2 and ALK3 to a greater extent than it does ALK6 (Yu et al. Nat. Chem. Biol. 4:33-41, 2008). Several of the compounds described herein will have relative greater selectivity for particular BMP type I receptors. The pathogenesis of certain diseases might be attributed to the dysfunctional signaling of one particular receptor. For example, fibrodysplasia ossificans progressiva is a disease caused by aberrant (constitutively active) ALK2 function (Yu et al. Nat. Chem. Biol. 4:33-41, 2008). In such instances, compounds as described herein which specifically antagonize the function a subset of the BMP type I receptors may have the advantage of reduced toxicity or side effects, or greater effectiveness, or both.

Some compounds as described herein may have a high degree of selectivity for BMP vs. TGF-$\beta$, Activin, AMP kinase, and VEGF receptor signaling. Other compounds may be less specific and may target other pathways in addition to BMP signaling. In the treatment of tumors, for example, agents which inhibit BMP signaling as well as one or more of the above pathways can have beneficial effects (e.g. decrease tumor size), when molecular phenotyping of specific patients' tumors reveals dysregulation of multiple pathways.

O. Applications of Compounds in Species Other than Human

Compounds as described herein can be used to treat subjects (e.g., humans, domestic pets, livestock, or other animals) by use of dosages and administration regimens that are determined to be appropriate by those of skill in the art, and these parameters may vary depending on, for example, the type and extent of the disorder treated, the overall health status of the subject, the therapeutic index of the compound, and the route of administration. Standard clinical trials can be used to optimize the dose and dosing frequency for any particular pharmaceutical composition of the invention. Exemplary routes of administration that can be used include oral, parenteral, intravenous, intra-arterial, subcutaneous, intramuscular, topical, intracranial, intraorbital, ophthalmic, intraventricular, intracapsular, intraspinal, intracisternal, intraperitoneal, intranasal, aerosol, or administration by suppository. Methods for making formulations that can be used in the invention are well known in the art and can be found, for example, in Remington: The Science and Practice of Pharmacy (20th edition, Ed., A. R. Gennaro), Lippincott Williams & Wilkins, 2000.

P. Inhibition of BMP Signaling in Insects

Some of the compounds as described herein may have activity against, and perhaps even selectivity for the BMP receptors of arthropods versus those of chordates. Inhibiting BMP signaling in arthropod larvae or eggs is likely to cause severe developmental abnormalities and perhaps compromise their ability to reproduce, e.g., via the same dorsalization that is observed in zebrafish and drosophila when this pathway is inhibited. If BMP antagonists as described herein have very strong selectivity for arthropod BMP receptors versus those of humans, they may be used as insecticides or pest control agents that are demonstrably less toxic or more environmentally sound than current strategies.

Q. Additional Embodiments of the Present Invention

As stated above, the compounds of the present invention can be used various other methods of treatment. For example, the compounds of the present invention can be used for methods to reduce myocardial ischemic injury (Pachori A K. Journal of Molecular and Cellular Cardiology 2010, 48:1255-65); methods for treating retinopathy of prematurity, diabetic retinopathy, and wet macular degeneration (Zhu D, Deng X, Xu J, Hinton D R. Aging 2009; 1:740-745; Zhu D, Wu J, Spee C, Ryan S J, Hinton Dr, Journal of Biological Chemistry 2009; 284:9529-9539); methods for treating aortic valve calcification (both native and prosthetic) (Ankeny R F, Thouranin V H, Weiss D, Vega J D, Taylor W R, Nerem R M, Jo H. PLoS ONE 2011; 6:e20969); methods for treat vascular calcification (Shao J-S, et al. Ann N.Y. Acad. Sciences 2007, 1117:40-50; Mohler E R, et al. Circulation 2001, 103:1522-1528); methods for treating diabetic nephropathy and renal fibrosis (Kishi S et al. Journal of Biological Chemistry 2011; 286: 32162-69; Patel S R and Dressler G R. Trends in Molecular Medicine 2005:11:512); methods for treating hereditary spastic paraplegias (Tsang H T H et al, Human Molecular Genetics 2009:18:3805-3821; Blackstone C, O'Kane C J, Reid E. Nature Neuroscience 2011; 12:31); methods for treating dystrophic phenotype in Duchenne Muscular Dystrophy (Shi S, et al. Neurobiology of Disease 2011, 41:353-360; Shi S, et al. Cell Mol Life Sci. 2013, 70:407-23); methods for treating inflammatory bowel disease (Wang, L, Trebicka, E, Fu, Y, Ellenbogen, S, Hong, C C, Babitt, J L, Lin, H Y, Cherayil, B J. The bone morphogenetic protein-hepcidin axis as a therapeutic target in inflammatory bowel disease. *Inflammatory Bowel Diseases* 2012; 18:112-119. PMID:21351217); method for treating childhood leukemia (Crispino J D and Le Beau M M. Cancer Cell 2012; 22:567; Gruber T A, et al. Cancer Cell 2012; 22:683-697); methods for treating cancer metastasis by targeting lymphatics and primary tumore growth (Farnsworth R H, et al. Cancer Res 2011; 71:6547-57); and methods for promoting liver regeneration and healing following acute injury, including hepatotoxin exposure, such as acetaminophen overdose (Do N, et al. Am J Physiol Gastrointest Liver Physiol 2012; 303: G1220-7).

2. Co-Administration Methods

The disclosed compounds may be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) may be administered by a route and in an amount commonly used therefore, contemporaneously or sequentially with a disclosed compound. When a disclosed compound is used contemporaneously with one or more other drugs, a pharmaceutical composition in unit dosage form containing such drugs and the compound is preferred. However, the combination therapy can also be administered on overlapping schedules. It is also envisioned that the combination of one or more active ingredients and a disclosed compound can be more efficacious than either as a single agent.

In certain instances BMP antagonists as described herein may be used in combination with other current or future drug therapies, because the effects of inhibiting BMP alone may be less optimal by itself, and/or may be synergistic or more highly effective in combination with therapies acting on distinct pathways which interact functionally with BMP signaling, or on the BMP pathway itself. Some examples of combination therapies could include the following.

Coadministration of erythropoietin (Epogen) and BMP antagonists as described herein may be especially effective for certain types of anemia of inflammation, as described above, particularly in diseases such as end-stage renal disease in which chronic inflammation and erythropoietin insufficiency both act to promote anemia.

Tyrosine kinase receptor inhibitors, such as SU-5416, and BMP antagonists as described herein may have synergistic effects at inhibiting angiogenesis, particularly for anti-angiogenic therapy against tumors. BMP signals (BMP-4) are thought to be critical for the commitment of stem or precursor cells to a hematopoietic/endothelial common progenitor, and may promote the proliferation, survival, and migration of mature endothelial cells necessary for angiogenesis (Park et al. Development 131:2749-2762, 2004). Thus antagonism of BMP signals using compounds as described herein may provide additional inhibition of angiogenesis at the level of endothelial precursors and cells. Similarly, co-treatment with BMP antagonists as described herein and other tyrosine kinase receptor inhibitors such as imatinib (Gleevec) could be used to inhibit vascular remodeling and angiogenesis of certain tumors.

The combination of a sonic hedgehog agonist and a BMP antagonist as described herein may be particularly useful for promoting hair growth, as SHH activity is known to stimulate the transition of follicles out of telogen (resting) phase (Paladini et al. J. Invest. Dermatol. 125:638-646, 2005), while inhibiting the BMP pathway shortens the telogen phase (Plikus et al. Nature 451:340-344, 2008). The use of both would be expected to cause relatively increased time in the anagen or growth phase.

Combined use of Notch modulators (e.g., gamma-secretase inhibitors) and BMP antagonists as described herein may be more effective than either agent alone in applications designed to inhibit vascular remodeling or bone differentiation, because increasing evidence suggests both pathways function cooperatively to effect cell differentiation, and vascular cell migration (Kluppel et al. Bioessays 27:115-118, 2005). These therapies may be synergistic in the treatment of tumors in which one or both pathways is deranged (Katoh, Stem Cell Rev. 3:30-38, 2007).

Combined use of an Indian Hedgehog (IHH) antagonist and a BMP antagonist as described herein may inhibit pathologic bone formation. IHH is responsible for the commitment of bone precursors to chondrocyte or cartilage forming cells. Endochondral bone formation involves coordinated activity of both chondrogenesis (promoted by BMP signals and IHH signals) and their subsequent calcification by mineralization programs initiated by BMP signals (Seki et al. J. Biol. Chem. 279:18544-18549, 2004; Minina et al. Development 128:4523-4534, 2001). Coadministration of an IHH antagonist with a BMP antagonist as described herein, therefore, may be more effective in inhibiting pathological bone growth due to hyperactive BMP signaling (such as in FOP), or in any of the inflammatory or traumatic disorders of pathologic bone formation described above.

Strong experimental evidence exists for an effect of both Smo antagonism and BMP antagonism for treating glioblastoma. Compounds as described herein may be used in combination with Smo antagonists to treat glioblastoma.

E. Manufacture of a Medicament

In one aspect, the invention relates to methods for the manufacture of a medicament for modulating BMP signaling in a subject in need thereof, comprising combining a compound of the following formula (I):

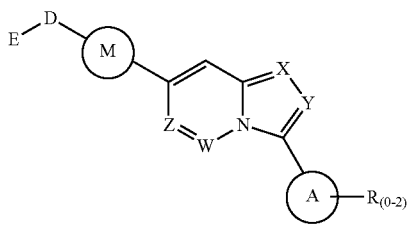

wherein:
W, X, Y, and Z are independently N or CH;
A is substituted or unsubstituted and selected from cycloalkyl, heterocycloalkyl, aryl or heteroaryl;
R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;
M is substituted or unsubstituted and is selected from aryl or heteroaryl;
D is selected from a bond, O, $CR_1R_2$ or NH or $NR_1$ or $NR_1R_2$ or $S(O)_{0-2}R_1R_2$;
E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;
$R_1$ is selected from H, alkyl, aryl, heteraryl, $COR_1$; and
$R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof, with a pharmaceutical carrier.

F. Uses of Compounds

In one aspect, the invention relates to uses of compounds for modulating BMP signaling in a subject in need thereof, wherein the compound has a structure represented by the following formula (I):

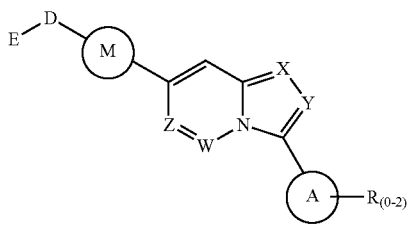

wherein:
W, X, Y, and Z are independently N or CH;
A is substituted or unsubstituted and selected from cycloalkyl, heterocycloalkyl, aryl or heteroaryl;
R is selected from H, $CF_3$, halogen, CN, alkyl, aryl, heteroaryl, $NR_1R_2$, $COR_1R_2$, $CR_1R_2$, $S(O)_{0-2}NR_1R_2$; $S(O)_{0-2}R_1R_2$;
M is substituted or unsubstituted and is selected from aryl or heteroaryl;
D is selected from a bond, O, $CR_1R_2$ or NH or $NR_1$ or $NR_1R_2$ or $S(O)_{0-2}R_1R_2$;
E is selected from H, $CF_3$, halogen, CN, alkyl, aryl, heteroaryl, $C_3$-$C_{12}$ cycloalkyl or $C_3$-$C_{12}$ cycloheteroalkyl or —$(CH_2)_x$—$C_3$-$C_{12}$ cycloalkyl or —$(CH_2)_x$—$C_3$-$C_{12}$ cycloheteroalkyl;

$R_1$ is selected from H, alkyl, aryl, heteraryl, $COR_1$; and
$R_2$ is selected from H, alkyl, aryl, heteraryl, $COR_1$, and further, $R_1$ and $R_2$ can form a $C_3$-$C_{12}$ cycloalkyl or $C_3$-$C_{12}$ cycloheteroalkyl containing O, N or S; or a pharmaceutically acceptable salt thereof, or a pharmaceutically acceptable derivative thereof.

In addition to being administered to patients in therapeutic methods, compounds as described herein can also be used to treat cells and tissues, as well as structural materials to be implanted into patients (see above), ex vivo. For example, the compounds can be used to treat explanted tissues that may be used, for example, in transplantation.

G. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

General.

All NMR spectra were recorded on a 400 MHz AMX Bruker NMR spectrometer. chemical shifts are reported in δ values in ppm downfield with the deuterated solvent as the internal standard. Data are reported as follows: chemical shift, multiplicity (s=singlet, d=doublet, t=triplet, q=quartet, br=broad, m=multiplet), integration, coupling constant (Hz). Low resolution mass spectra were obtained on an Agilent 1200 series 6130 mass spectrometer with electrospray ionization. High resolution mass spectra were recorded on a Waters Q-TOF API-US plus Acquity system with electrospray ionization. Analytical thin layer chromatography was performed on EM Reagent 0.25 mm silica gel 60-F plates. Analytical HPLC was performed on an Agilent 1200 series with UV detection at 215 nm and 254 nm along with ELSD detection. LC/MS: (Phenomenex-C18, 2.1×30 mm, 1 min gradient, 7%[0.1% TFA/$CH_3CN$]:93%[0.1% TFA/$H_2O$] to 95%[0.1% TFA/$CH_3CN$]. Preparative purification was performed on a custom HP1100 purification system (reference 16) with collection triggered by mass detection. Solvents for extraction, washing and chromatography were HPLC grade. All reagents were purchased from Aldrich Chemical Co. and were used without purification.

General Scheme I

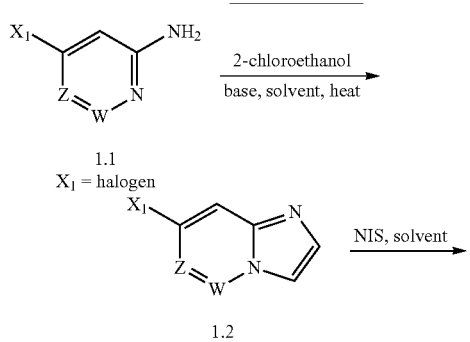

-continued

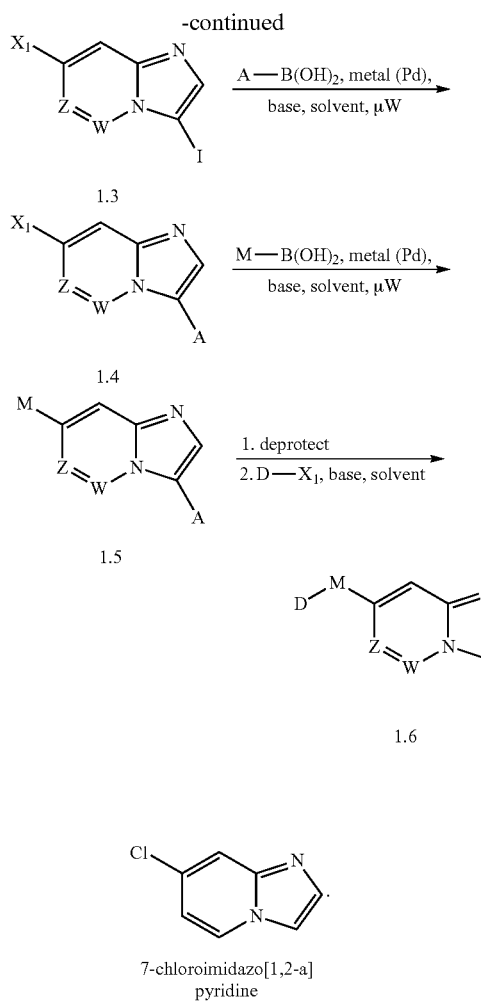

1.3

1.4

1.5

1.6

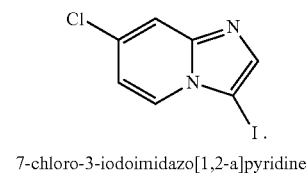

7-chloroimidazo[1,2-a]pyridine

To a mixture of 4-chloropyridin-2-amine (1.0 g, 7.78 mmol, 1.0 eq) and NaHCO$_3$ (1.31 g, 15.56 mmol, 2.0 eq) in EtOH (18 mL) was added chloroacetaldehyde, 50% wt in water, (1.48 mL, 11.67 mmol, 1.5 eq). The reaction mixture was heated to reflux. After 10 h, the solvent was removed under reduced pressure and the residue was partitioned between EtOAc: H$_2$O (1:1, 100 mL). The organic layer was washed with Brine (50 mL), dried (MgSO$_4$), filtered and concentrated. The material was taken through without further purification.

LCMS: R$_T$=0.123 min, >98% @ 215 and 254 nM, m/z=153.0 [M+H]$^+$.

7-chloro-3-iodoimidazo[1,2-a]pyridine

To a solution of 7-chloroimidazo[1,2-a]pyridine (7.78 mmol, 1.0 eq) in DMF (12 mL) at rt was added N-iodosuccinimide (1.84 g, 8.17 mmol, 1.05 eq). After 16 h, the brown slurry was diluted with H$_2$O (100 mL) and Brine (15 mL). The mixture was extracted with EtOAc (100 mL). The aqueous layer was re-extracted with EtOAc (100 mL) and the collected organic layers were washed with H$_2$O (2×20 mL), 10% sodium thiosulfate (20 mL), Brine (20 mL) and dried (MgSO$_4$). After filtration, the solution was concentrated. The residue was triturated with diethyl ether (15 mL) and filtered to afford an off-white solid (1.58 g, 73% yield over 2 steps).

LCMS: R$_T$=0.265 min, >98% @ 215 and 254 nM, m/z=279.0 [M+H]$^+$.

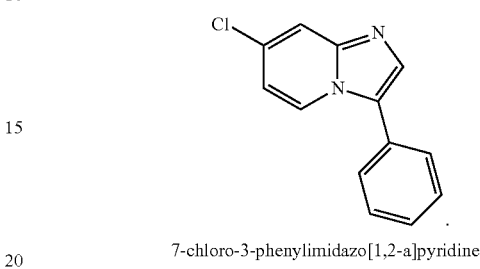

7-chloro-3-phenylimidazo[1,2-a]pyridine

In a μwave vial, 7-chloro-3-iodoimidazo[1,2-a]pyridine (0.39 g, 1.38 mmol, 1.0 eq), phenyl boronic acid (0.18 g, 1.45 mmol, 1.05 eq), and Pd(dppf)Cl$_2$ (50.5 mg, 0.07 mmol, 0.05 eq) were added. The solid mixture was evacuated under vacuo and purged with Argon (3×). To the mixture was added 1,4-dioxane (6 mL), followed by a solution of K$_3$PO$_4$ (0.59 g, 2.76 mmol, 2.0 eq) in H$_2$O (2.5 mL). The reaction was heated to 120° C. for 30 min under microwave irradiation. The reaction was added to EtOAc: H$_2$O (1:1, 120 mL). The organic layer was separated, washed with H$_2$O (2×25 mL), Brine (25 mL), dried (MgSO$_4$), filtered and concentrated. The material was purified by reverse-phase HPLC (15-40% acetonitrile: H$_2$O w/0.1% TFA) to provide 7-chloro-3-phenylimidazo[1,2-a]pyridine (0.30 g, 96% yield).

LCMS: R$_T$=0.458 min, >98% @ 215 and 254 nM, m/z=229.0 [M+H]$^+$.

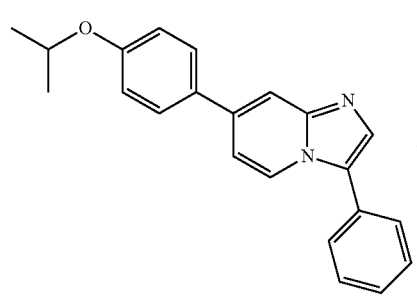

7-(4-isopropoxyphenyl)-3-phenylimidazo[1,2-a]pyridine

In a μwave vial, 7-chloro-3-phenylimidazo[1,2-a]pyridine (5) (25.0 mg, 0.11 mmol, 1.0 eq), boronic acid 6 (22.0 mg, 0.121 mmol, 1.1 eq), and Pd(dppf)Cl$_2$ (4.0 mg, 0.006 mmol, 0.05 eq) were added. The solid mixture was evacuated under vacuo and purged with Argon (3×). To the mixture was added 1,4-dioxane (2 mL), followed by a solution of K$_2$CO$_3$ (30.0 mg, 0.22 mmol, 2.0 eq) in H$_2$O (1.0 mL). The reaction was heated to 150° C. for 30 min under microwave irradiation. The reaction was added to EtOAc: H$_2$O (1:1, 20 mL). The organic layer was separated, washed with H$_2$O (5 mL), Brine (5 mL), dried (MgSO$_4$), filtered and concentrated. The material was purified by reverse-phase HPLC (30-65% acetonitrile: H₂O w/0.1% TFA) to afford 7-(4-isopropoxyphenyl)-3-phenylimidazo[1,2-a]pyridine (5.30 mg, 15% yield).

LCMS: $R_T$=0.714 min, >98% @ 215 and 254 nM, m/z=329.0 [M+H]⁺.

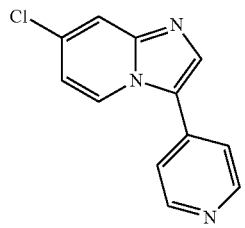

7-chloro-3-(pyridin-4-yl)
imidazo[1,2-a]pyridine

In a μwave vial, 7-chloro-3-iodoimidazo[1,2-a]pyridine (3) (0.31 g, 1.13 mmol, 1.0 eq), 4-pyridyl boronic acid (0.15 g, 1.24 mmol, 1.1 eq), and Pd(dppf)Cl₂ (41.0 mg, 0.06 mmol, 0.05 eq) were added. The solid mixture was evacuated under vacuo and purged with Argon (3×). To the mixture was added 1,4-dioxane (5 mL), followed by a solution of K₃PO₄ (0.48 g, 2.26 mmol, 2.0 eq) in H₂O (2.0 mL). The reaction was heated to 120° C. for 30 min under microwave irradiation. The reaction was added to EtOAc: H₂O (1:1, 120 mL). The organic layer was separated, washed with H₂O (2×25 mL), Brine (25 mL), dried (MgSO₄), filtered and concentrated. The material was taken through without further purification.

LCMS: $R_T$=0.147 min, >98% @ 215 and 254 nM, m/z=230.0 [M+H]⁺.

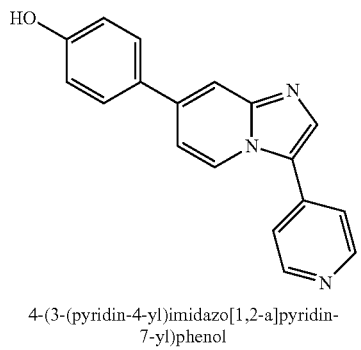

4-(3-(pyridin-4-yl)imidazo[1,2-a]pyridin-
7-yl)phenol

In a μwave vial, 7-chloro-3-(pyridin-4-yl)imidazo[1,2-a]pyridine (0.28 g, 1.23 mmol, 1.0 eq), 4-hydroxyphenyl boronic acid (0.19 g, 1.35 mmol, 1.1 eq), and Pd(dppf)Cl₂ (45.0 mg, 0.06 mmol, 0.05 eq) were added. The solid mixture was evacuated under vacuo and purged with Argon (3×). To the mixture was added 1,4-dioxane (5 mL), followed by a solution of K₂CO₃ (0.34 g, 2.46 mmol, 2.0 eq) in H₂O (2.0 mL). The reaction was heated to 150° C. for 30 min under microwave irradiation. The reaction was added to EtOAc: H₂O (1:1, 20 mL). The organic layer was separated, washed with H₂O (5 mL), Brine (5 mL), dried (MgSO₄), filtered and concentrated. The material was purified by reverse-phase HPLC (5-35% acetonitrile: H₂O w/0.1% TFA) to afford 4-(3-(pyridin-4-yl)imidazo[1,2-a]pyridin-7-yl)phenol (53.0 mg, 15% yield).

LCMS: $R_T$=0.343 min, >98% @ 215 and 254 nM, m/z=288.0 [M+H]⁺.

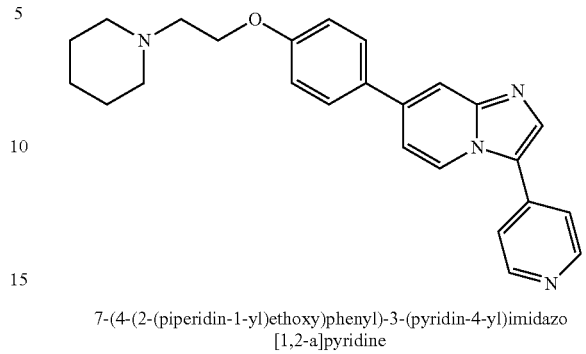

7-(4-(2-(piperidin-1-yl)ethoxy)phenyl)-3-(pyridin-4-yl)imidazo
[1,2-a]pyridine

To a μwave vial was added 4-(3-(pyridin-4-yl)imidazo[1,2-a]pyridin-7-yl)phenol (29.5 mg, 0.10 mmol, 1.0 eq), Cs₂CO₃ (134.0 mg, 0.411 mmol, 4.0 eq), KI (16.6 mg, 0.10 mmol, 1.0 eq), 1-(2-chloroethyl)piperidine hydrochloride (20.3 mg, 0.11 mmol, 1.1 eq) and DMF (1.5 mL). The rxn was subjected to microwave irradiation for 10 min at 120° C. The reaction was filtered through a Celite plug and the solution was purified by reverse-phase HPLC (5-35% acetonitrile: H₂O w/0.1% TFA) to afford 7-(4-(2-(piperidin-1-yl)ethoxy)phenyl)-3-(pyridin-4-yl)imidazo[1,2-a]pyridine (15.02 mg, 38% yield).

LCMS: $R_T$=0.404 min, >98% @ 215 and 254 nM, m/z=399.0 [M+H]⁺.

General Scheme II

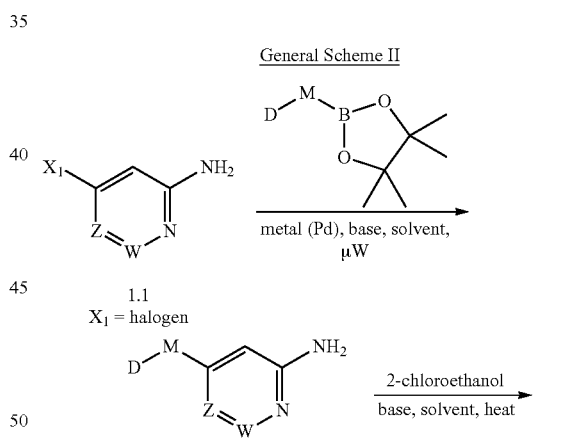

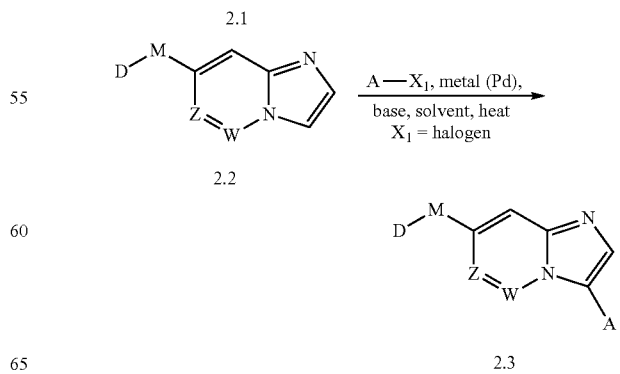

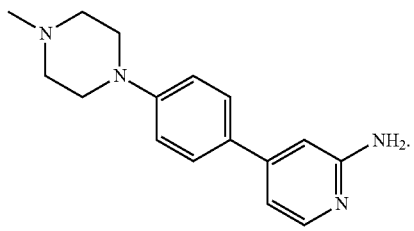

4-(4-(4-methylpiperazin-1-yl)phenyl)pyridin-2-amine

In a μwave vial, 4-bromopyridin-2-amine (0.50 g, 2.89 mmol, 1.0 eq), boronic ester (0.92 g, 3.03 mmol, 1.05 eq), and Pd(dppf)Cl$_2$ (106 mg, 0.15 mmol, 0.05 eq) were added. The solid mixture was evacuated under vacuo and purged with Argon (3×). To the mixture was added 1,4-dioxane (12 mL), followed by a solution of K$_3$PO$_4$ (1.23 g, 5.78 mmol, 2.0 eq) in H$_2$O (5.0 mL). The reaction was heated to 120° C. for 30 min under microwave irradiation. To the reaction was added EtOAc (15 mL) and the rxn was filtered. The solid was rinsed with cold EtOAc (2 mL). The material was taken through without further purification.

LCMS: R$_T$=0.285 min, >98% @ 215 nM and ELSD, m/z=269.1 [M+H]$^+$.

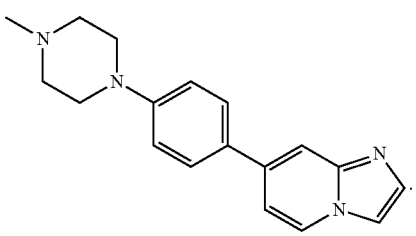

7-(4-(4-methylpiperazin-1-yl)phenyl)imidazo[1,2-a]pyridine

To a mixture of 4-(4-(4-methylpiperazin-1-yl)phenyl) pyridin-2-amine (2.89 mmol, 1.0 eq) and NaHCO$_3$ (0.49 g, 5.78 mmol, 2.0 eq) in EtOH (30 mL) was added chloroacetaldehyde, 50% wt in water, (0.56 mL, 4.34 mmol, 1.5 eq). The reaction mixture was heated to reflux. After 18 h, the solvent was removed under reduced pressure and the residue was partitioned between EtOAc: H$_2$O (1:1, 100 mL). The organic layer was washed with Brine (50 mL), dried (MgSO$_4$), filtered and concentrated. The material was taken through without further purification.

LCMS: R$_T$=0.343 min, >90% @ 215 nM and ELSD, m/z=293.1 [M+H]$^+$.

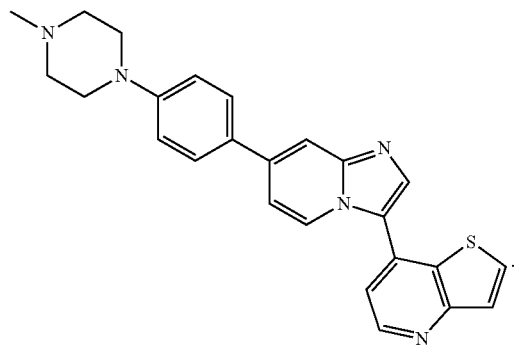

7-(7-(4-(4-methylpiperazin-1-yl)phenyl)imidazo[1,2-a]pyridin-3-yl)thieno[3,2-b]pyridine In a μwave vial, 7-(4-(4-methylpiperazin-1-yl)phenyl) imidazo[1,2-a]pyridine (23 mg, 0.08 mmol, 1.1 eq), 7-chlorothieno[3,2-b]pyridine (8 μL, 0.071 mmol, 1.0 eq), KOAc (14.0 mg, 0.143 mmol, 2.0 eq) and Pd(OAc)$_2$ (~1 mg, 0.001 eq) were added, followed by the addition of DMA (1.5 mL). The reaction was heated to 200° C. for 30 min under microwave irradiation. To the reaction was added DMSO (0.5 mL) and after filtration through a Celite plug, the solution was purified by reverse-phase HPLC (20-55% acetonitrile: H$_2$O w/0.1% TFA) to afford 7-(7-(4-(4-methylpiperazin-1-yl)phenyl)imidazo[1,2-a]pyridin-3-yl)thieno [3,2-b]pyridine (14.0 mg, 47% yield).

LCMS: R$_T$=0.361 min, >98% @ 215 nM and ELSD, m/z=370.1 [M+H]$^+$.

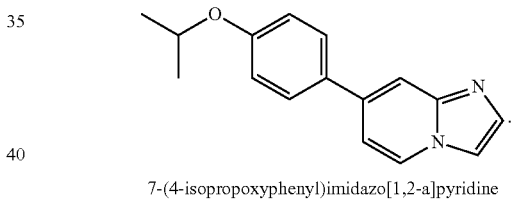

7-(4-isopropoxyphenyl)imidazo[1,2-a]pyridine

Compound 7-(4-isopropoxyphenyl)imidazo[1,2-a]pyridine was prepared in a similar manner to 7-(4-(4-methylpiperazin-1-yl)phenyl)imidazo[1,2-a]pyridine.

LCMS: R$_T$=0.578 min, >98% @ 220 and 254 nM, m/z=253.1 [M+H]$^+$.

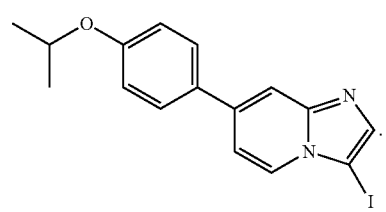

3-iodo-7-(4-isopropoxyphenyl)imidazo[1,2-a]pyridine

To a solution of compound 7-(4-isopropoxyphenyl)imidazo[1,2-a]pyridine (2.89 mmol, 1.0 eq) in DMF (20 mL) at rt was added N-iodosuccinimide (0.68 g, 3.03 mmol, 1.05 eq). After 16 h, the brown slurry was diluted with H$_2$O (100 mL) and Brine (15 mL). The mixture was extracted with EtOAc (100 mL). The aqueous layer was re-extracted with EtOAc (100 mL) and the collected organic layers were washed with H$_2$O (2×20 mL), 10% sodium thiosulfate (20 mL), Brine (20 mL) and dried (MgSO$_4$). After filtration, the solution was concentrated and the material was taken through without further purification.

LCMS: R$_T$=0.640 min, >95% @ 220 nM and ELSD, m/z=378.9 [M+H]$^+$.

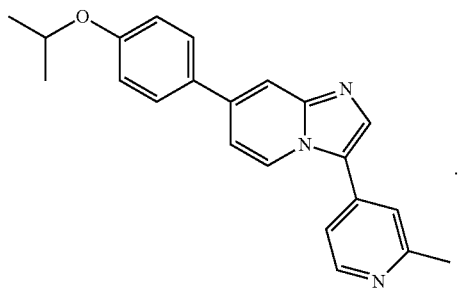

7-(4-isopropoxyphenyl)-3-(2-methylpyridin-4-yl)imidazo[1,2-a]pyridine

In a μwave vial, 3-iodo-7-(4-isopropoxyphenyl)imidazo[1,2-a]pyridine (35 mg, 0.093 mmol, 1.0 eq), (2-methylpyridin-4-yl)boronic acid (15 mg, 0.11 mmol, 1.2 eq), and Pd(dppf)Cl$_2$ (4.0 mg, 0.005 mmol, 0.05 eq) were added. The solid mixture was evacuated under vacuo and purged with Argon (3×). To the mixture was added 1,4-dioxane (2 mL), followed by a solution of K$_3$PO$_4$ (40 mg, 0.19 mmol, 2.0 eq) in H$_2$O (0.5 mL). The reaction was heated to 120° C. for 30 min under microwave irradiation. The reaction was added to EtOAc: H$_2$O (1:1, 20 mL). The organic layer was separated, washed with H$_2$O (2×25 mL), Brine (25 mL), dried (MgSO$_4$), filtered and concentrated. The residue was purified by reverse-phase HPLC (20-55% acetonitrile: H$_2$O w/0.1% TFA) to afford 7-(4-isopropoxyphenyl)-3-(2-methylpyridin-4-yl)imidazo[1,2-a]pyridine (4.3 mg, 14% yield).

LCMS: R$_T$=0.544 min, >98% @ 215 nM and ELSD, m/z=344.1 [M+H]$^+$.

| Example | Compound | Name | M + H |
|---|---|---|---|
| 1 | | 4-(2-(4-(3-(quinolin-4-yl)imidazo[1,2-a]pyridin-7-yl)phenoxy)ethyl)morpholine | 451 |
| 2 | | 5-(7-(4-isopropoxyphenyl)imidazo[1,2-a]pyridin-3-yl)isoquinoline | 380 |
| 3 | | 4-(2-(4-(3-(pyridin-4-yl)imidazo[1,2-a]pyridin-7-yl)phenoxy)ethyl)morpholine | 401 |

-continued

| Example | Compound | Name | M + H |
|---|---|---|---|
| 4 | | 7-(4-(2-(piperidin-1-yl)ethoxy)phenyl)-3-(pyridin-4-yl)imidazo[1,2-a]pyridine | 399 |
| 5 | | 4-(7-(2,3-dihydrobenzo[b][1,4]dioxin-6-yl)imidazo[1,2-a]pyridin-3-yl)quinoline | 380 |
| 6 | | 7-(2,3-dihydrobenzo[b][1,4]dioxin-6-yl)-3-(pyridin-4-yl)imidazo[1,2-a]pyridine | 330 |
| 7 | | 7-(4-(tert-butyl)phenyl)-3-(pyridin-4-yl)imidazo[1,2-a]pyridine | 328 |
| 8 | | 7-(4-isopropoxyphenyl)-3-(pyridin-4-yl)imidazo[1,2-a]pyridine | 330 |

-continued

| Example | Compound | Name | M + H |
|---|---|---|---|
| 9 | | 7-(4-phenoxyphenyl)-3-(pyridin-4-yl)imidazo[1,2-a]pyridine | 364 |
| 10 | | 5-(7-(4-isopropoxyphenyl)imidazo[1,2-a]pyridin-3-yl)quinoline | 380 |
| 11 | | 8-(7-(4-isopropoxyphenyl)imidazo[1,2-a]pyridin-3-yl)quinoline | 380 |
| 12 | | 7-(4-isopropoxyphenyl)-3-(naphthalen-1-yl)imidazo[1,2-a]pyridine | 379 |
| 13 | | 6-(7-(4-isopropoxyphenyl)imidazo[1,2-a]pyridin-3-yl)quinoxaline | 381 |

-continued

| Example | Compound | Name | M + H |
|---|---|---|---|
| 14 | | 3-(7-(4-isopropoxyphenyl)imidazo[1,2-a]pyridin-3-yl)quinoline | 380 |
| 15 | | 4-(3-phenylimidazo[1,2-a]pyridin-7-yl)aniline | 286 |
| 16 | | 6-(7-(4-isopropoxyphenyl)imidazo[1,2-a]pyridin-3-yl)isoquinoline | 380 |
| 17 | | 7-(7-(4-isopropoxyphenyl)imidazo[1,2-a]pyridin-3-yl)isoquinoline | 380 |
| 18 | | 4-(7-(4-isopropoxyphenyl)imidazo[1,2-a]pyridin-3-yl)isoquinoline | 380 |

| Example | Compound | Name | M + H |
|---|---|---|---|
| 19 | | 4-(7-(4-isopropoxyphenyl)imidazo[1,2-a]pyridin-3-yl)quinoline | 380 |
| 20 | | N-(4-(3-phenylimidazo[1,2-a]pyridin-7-yl)phenyl)picolinamide | 391 |
| 21 | | 4-(7-(4-(4-methylpiperazin-1-yl)phenyl)imidazo[1,2-a]pyridin-3-yl)quinoline | 420 |
| 22 | | 4-(7-(4-isopropoxyphenyl)imidazo[1,2-a]pyridin-3-yl)phenol | 345 |

-continued

| Example | Compound | Name | M + H |
|---|---|---|---|
| 23 | | 4-(7-(4-isopropoxyphenyl)imidazo[1,2-a]pyridin-3-yl)-N,N-dimethylaniline | 372 |
| 24 | | 6-(7-(4-isopropoxyphenyl)imidazo[1,2-a]pyridin-3-yl)quinoline | 380 |
| 25 | | 3-(2-chloropyridin-4-yl)-7-(4-isopropoxyphenyl)imidazo[1,2-a]pyridine | 364 |
| 26 | | 3-(2-fluoropyridin-4-yl)-7-(4-isopropoxyphenyl)imidazo[1,2-a]pyridine | 348 |
| 27 | | 7-chloro-4-(7-(4-isopropoxyphenyl)imidazo[1,2-a]pyridin-3-yl)quinoline | 414 |

-continued

| Example | Compound | Name | M + H |
|---|---|---|---|
| 28 | | 3-(2'-chloro-[2,4'-bipyridin]-4-yl)-7-(4-isopropoxyphenyl)imidazo[1,2-a]pyridine | 441 |
| 29 | | 7-(4-isopropoxyphenyl)-3-(pyrimidin-5-yl)imidazo[1,2-a]pyridine | 331 |
| 30 | | 4-(2-(4-(3-phenylimidazo[1,2-a]pyridin-7-yl)phenoxy)ethyl)morpholine | 400 |
| 31 | | 4-(3-phenylimidazo[1,2-a]pyridin-7-yl)phenol | 287 |
| 32 | | 7-(4-phenoxyphenyl)-3-phenylimidazo[1,2-a]pyridine | 363 |

-continued
| Example | Compound | Name | M + H |
|---|---|---|---|
| 33 | 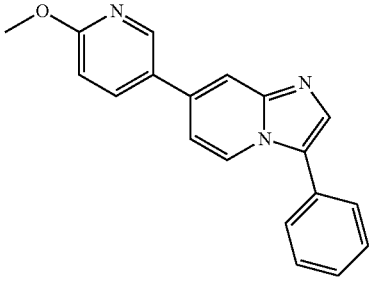 | 7-(6-methoxypyridin-3-yl)-3-phenylimidazo[1,2-a]pyridine | 302 |
| 34 | 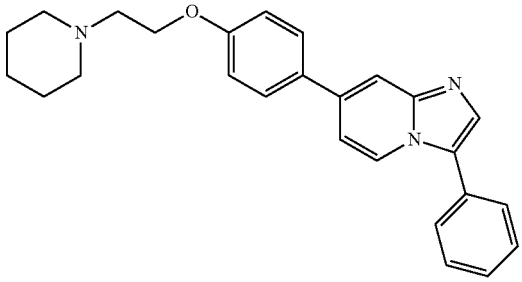 | 3-phenyl-7-(4-(2-(piperidin-1-yl)ethoxy)phenyl)imidazo[1,2-a]pyridine | 398 |
| 35 | 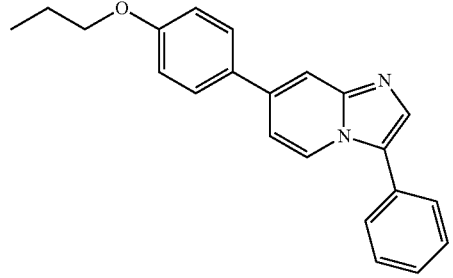 | 3-phenyl-7-(4-propoxyphenyl)imidazo[1,2-a]pyridine | 329 |
| 36 | 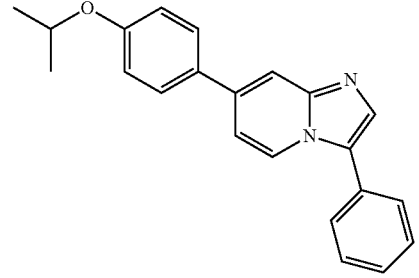 | 7-(4-isopropoxyphenyl)-3-phenylimidazo[1,2-a]pyridine | 329 |
| 37 | 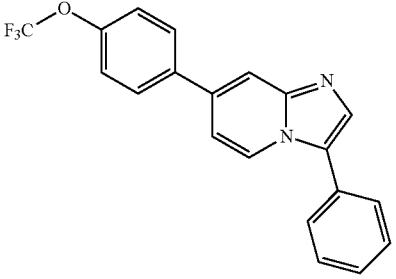 | 3-phenyl-7-(4-(trifluoromethoxy)phenyl)imidazo[1,2-a]pyridine | 355 |

-continued

| Example | Compound | Name | M + H |
|---|---|---|---|
| 38 | | 7-(4-isopropoxyphenyl)-3-phenylimidazo[1,2-a]pyridine | 329 |
| 39 | | 3-(1,5-dimethyl-1H-pyrazol-4-yl)-7-(4-isopropoxyphenyl)imidazo[1,2-a]pyridine | 347 |
| 40 | | 3-(3,5-dimethyl-1H-pyrazol-4-yl)-7-(4-isopropoxyphenyl)imidazo[1,2-a]pyridine | 347 |
| 41 | | 4-(7-(4-isopropoxyphenyl)imidazo[1,2-c]pyrimidin-3-yl)quinoline | 381 |
| 42 | | 7-(4-isopropoxyphenyl)-3-(1H-pyrazol-4-yl)imidazo[1,2-a]pyridine | 319 |

-continued

| Example | Compound | Name | M + H |
|---|---|---|---|
| 43 | | 3-(1-(4-fluorophenyl)-1H-pyrazol-4-yl)-7-(4-isopropoxyphenyl)imidazo[1,2-a]pyridine | 413 |
| 44 | | 7-(4-isopropoxyphenyl)-3-(3-methyl-1H-pyrazol-4-yl)imidazo[1,2-a]pyridine | 333 |
| 45 | | 7-(4-isopropoxyphenyl)-3-(2-methylpyridin-4-yl)imidazo[1,2-a]pyridine | 344 |
| 46 | | 3-(3-bromo-2-fluoropyridin-4-yl)-7-(4-isopropoxyphenyl)imidazo[1,2-a]pyridine | 427 |
| 47 | | 4-(7-(4-(4-methylpiperazin-1-yl)phenyl)imidazo[1,2-a]pyridin-3-yl)-7-(trifluoromethyl)quinoline | 488 |

-continued

| Example | Compound | Name | M + H |
|---|---|---|---|
| 48 | | 7-(4-(4-methylpiperazin-1-yl)phenyl)-3-(3-methylpyridin-4-yl)imidazo[1,2-a]pyridine | 384 |
| 49 | | 7-(4-(4-methylpiperazin-1-yl)phenyl)-3-(thiophen-3-yl)imidazo[1,2-a]pyridine | 375 |
| 50 | | 4-(7-(4-(4-methylpiperazin-1-yl)phenyl)imidazo[1,2-a]pyridin-3-yl)-2-(trifluoromethyl)quinoline | 488 |
| 51 | | 2-methyl-4-(7-(4-(4-methylpiperazin-1-yl)phenyl)imidazo[1,2-a]pyridin-3-yl)quinoline | 434 |

-continued

| Example | Compound | Name | M + H |
|---|---|---|---|
| 52 | | 5-(7-(4-isopropoxyphenyl)imidazo[1,2-a]pyridin-3-yl)thiazole | 336 |
| 53 | | 7-(4-isopropoxyphenyl)-3-(thiophen-3-yl)imidazo[1,2-a]pyridine | 335 |
| 54 | | 7-(4-isopropoxyphenyl)-3-(3-methylpyridin-4-yl)imidazo[1,2-a]pyridine | 344 |
| 55 | | 7-(4-isopropoxyphenyl)-3-(thiophen-2-yl)imidazo[1,2-a]pyridine | 335 |
| 56 | | 3-(4-fluorophenyl)-7-(4-(4-methylpiperazin-1-yl)phenyl)imidazo[1,2-a]pyridine | 387 |

-continued

| Example | Compound | Name | M + H |
|---|---|---|---|
| 57 | | 3-(benzo[b]thiophen-2-yl)-7-(4-(4-methylpiperazin-1-yl)phenyl)imidazo[1,2-a]pyridine | 425 |
| 58 | | 4-(7-(4-(4-methylpiperazin-1-yl)phenyl)imidazo[1,2-a]pyridin-3-yl)benzonitrile | 394 |
| 59 | | 5-(7-(4-(4-methylpiperazin-1-yl)phenyl)imidazo[1,2-a]pyridin-3-yl)brnzo[d]thiazole | 426 |
| 60 | | 7-(7-(4-(4-methylpiperazin-1-yl)phenyl)imidazo[1,2-a]pyridin-3-yl)thieno[2,3-b]pyrazine | 427 |

-continued
| Example | Compound | Name | M + H |
|---|---|---|---|
| 61 | 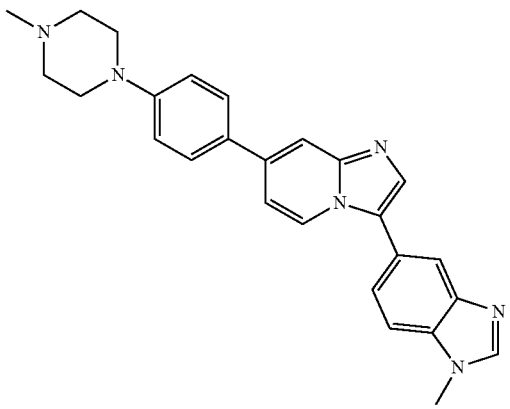 | 1-methyl-5-(7-(4-(4-methylpiperazin-1-yl)phenyl)imidazo[1,2-a]pyridin-3-yl)-1H-benzo[d]imidazole | 423 |
| 62 | 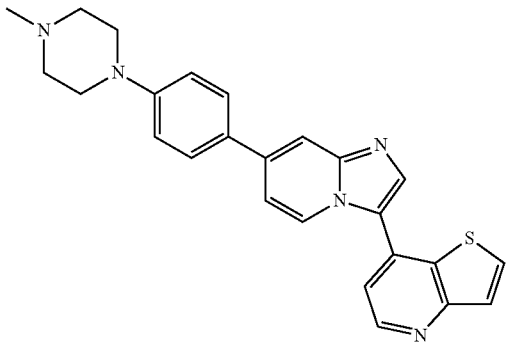 | 7-(7-(4-(4-methylpiperazin-1-yl)phenyl)imidazo[1,2-a]pyridin-3-yl)thieno[3,2-b]pyridine | 426 |
| 63 | 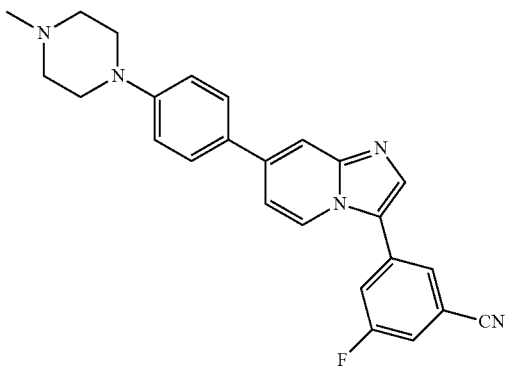 | 3-fluoro-5-(7-(4-(4-methylpiperazin-1-yl)phenyl)imidazo[1,2-a]pyridin-3-yl)benzonitrile | 412 |
| 64 | 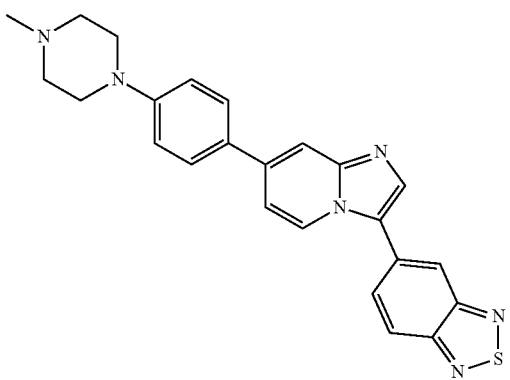 | 5-(7-(4-(4-methylpiperazin-1-yl)phenyl)imidazo[1,2-a]pyridin-3-yl)benzo[c][1,2,5]thiadiazole | 427 |

-continued
| Example | Compound | Name | M + H |
|---------|----------|------|-------|
| 65 | 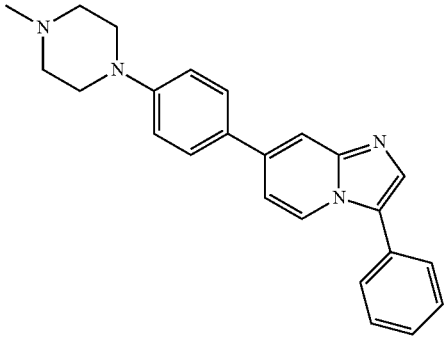 | 7-(4-(4-methylpiperazin-1-yl)phenyl)-3-phenylimidazo[1,2-a]pyridine | 369 |
| 66 | 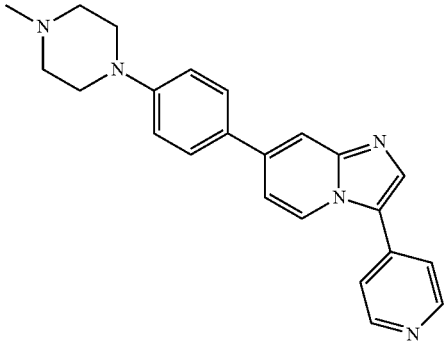 | 7-(4-(4-methylpiperazin-1-yl)phenyl)-3-(pyridin-4-yl)imidazo[1,2-a]pyridine | 370 |
| 67 | 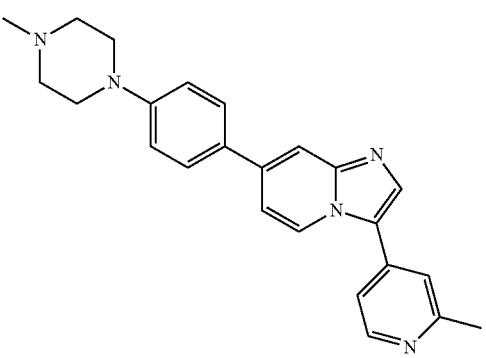 | 7-(4-(4-methylpiperazin-1-yl)phenyl)-3-(2-methylpyridin-4-yl)imidazo[1,2-a]pyridine | 384 |
| 68 | 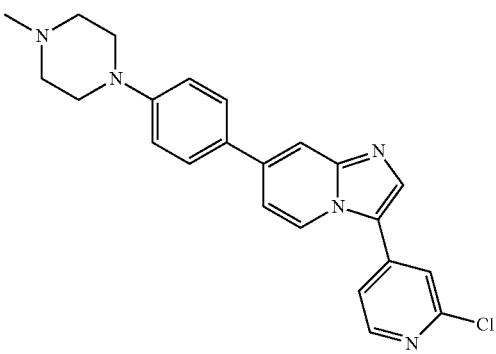 | 3-(2-chloropyridin-4-yl)-7-(4-(4-methylpiperazin-1-yl)phrnyl)imidazo[1,2-a]pyridine | 404 |

-continued

| Example | Compound | Name | M + H |
|---|---|---|---|
| 69 | | 7-(4-(4-methylpiperazin-1-yl)phenyl)-3-(pyridin-3-yl)imidazo[1,2-a]pyridine | 370 |
| 70 | | 4-(7-(4-(4-methylpiperazin-1-yl)phenyl)-[1,2,4]triazolo[4,3-a]pyridin-3-yl)quinoline | 421 |
| 71 | | 4-(2-(4-(3-(quinolin-4-yl)-[1,2,4]triazolo[4,3-a]pyridin-7-yl)phenoxy)ethyl)morpholine | 452 |
| 72 | | N,N-dimethyl-2-(4-(3-(quinolin-4-yl)-[1,2,4]triazolo[4,3-a]pyridin-7-yl)phenoxy)propan-1-amine | 424 |
| 73 | | 4-(7-(4-(2-(piperidin-1-yl)ethoxy)phenyl)-[1,2,4]triazolo[4,3-a]pyridin-3-yl)quinoline | 450 |

-continued

| Example | Name | M + H |
|---|---|---|
| 74 | 4-(7-(4-(2-(pyrrolidin-1-yl)ethoxy)phenyl)-[1,2,4]triazolo[4,3-a]pyridin-3-yl)quinoline | 436 |
| 75 | N,N-dimethyl-1-(4-(3-(quinoin-4-yl)-[1,2,4]triazolo[4,3-a]pyridin-7-yl)phenoxy)propan-2-amine | 424 |
| 76 | 4-(3-(quinolin-4-yl)-[1,2,4]triazolo[4,3-a]pyridin-7-yl)phenol | 339 |
| 77 | 4-(7-(4-methoxyphenyl)-[1,2,4]triazolo[4,3-a]pyridin-3-yl)quinoline | 353 |
| 78 | 4-(7-(4-propoxyphenyl)-[1,2,4]triazolo[4,3-a]pyridin-3-yl)quinoline | 381 |

-continued

| Example | Compound | Name | M + H |
|---|---|---|---|
| 79 | | 4-(3-(quinolin-4-yl)-[1,2,4]triazolo[4,3-a]pyridin-7-yl)phenyl acetate | 381 |
| 80 | | 4-(7-(4-butoxyphenyl)-[1,2,4]triazolo[4,3-a]pyridin-3-yl)quinoline | 395 |
| 81 | | 4-(3-(quinolin-4-yl)-[1,2,4]triazolo[4,3-a]pyridin-7-yl)phenylbenzoate | 443 |
| 82 | | 4-(7-(4-(cyclopentyloxy)phenyl)-[1,2,4]triaxolo[4,3-a]pyridin-3-yl)quinoline | 407 |
| 83 | | 4-(7-(4-isopropoxyphenyl)-[1,2,4]triazolo[4,3-a]pyridin-3-yl)quinoline | 381 |

-continued

| Example | Compound | Name | M + H |
|---|---|---|---|
| 84 | | 4-(7-(4-ethoxyphenyl)-[1,2,4]triazolo[4,3-a]pyridin-3-yl)quinoline | 367 |
| 85 | | 4-(7-(4-(allyloxy)phenyl)-[1,2,4]triazolo[4,3-a]pyridin-3-yl)quinoline | 379 |
| 86 | | 4-(7-(4-(sec-butoxy)phenyl)-[1,2,4]triazolo[4,3-a]pyridin-3-yl)quinoline | 395 |
| 87 | | 1-cyclopentyl-4-(3-(quinolin-4-yl)-[1,2,4]triazolo[4,3-a]pyridin-7-yl)pyridin-2(1H)-one | 408 |
| 88 | | 1-ethyl-4-(3-(quinolin-4-yl)-[1,2,4]triazolo[4,3-a]pyridin-7-yl)pyridin-2(1H)-one | 368 |

-continued

| Example | Compound | Name | M + H |
|---|---|---|---|
| 89 | | 1-isopropyl-4-(3-(quinolin-4-yl)-[1,2,4]triazolo[4,3-a]pyridin-7-yl)pyridin-2(1H)-one | 382 |
| 90 | | 1-methyl-4-(3-(quinolin-4-yl)-[1,2,4]triazolo[4,3-a]pyridin-7-yl)pyridin-2(1H)-one | 354 |
| 91 | | 1-butyl-4-(3-(quinolin-4-yl)-[1,2,4]triazolo[4,3-a]pyridin-7-yl)pyridin-2(1H)-one | 396 |
| 92 | | 1-propyl-4-(3-(quinolin-4-yl)-[1,2,4]triazolo[4,3-a]pyridin-7-yl)pyridin-2(1H)-one | 382 |

-continued

| Example | Compound | Name | M + H |
|---|---|---|---|
| 93 | | 1-allyl-4-(3-(quinolin-4-yl)-[1,2,4]triazolo[4,3-a]pyridin-7-yl)pyridin-2(1H)-one | 380 |
| 94 | | 4-(3-(quinolin-4-yl)-[1,2,4]triazolo[4,3-a]pyridin-7-yl)pyridin-2(1H)-one | 340 |
| 95 | | 1-(sec-butyl)-4-(3-(quinolin-4-yl)-[1,2,4]triazolo[4,3-a]pyridin-7-yl)pyridin-2(1H)-one | 396 |

| Example | R | $R_1$ | BMP4 Cell $IC_{50}$ (nM) |
|---|---|---|---|
| 1 | morpholinoethyl | quinolin-4-yl | 62 |

-continued
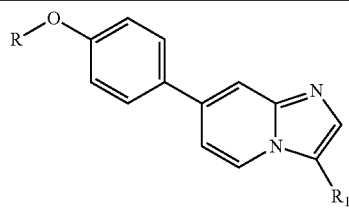
| Example | R | R₁ | BMP4 Cell IC$_{50}$ (nM) |
|---|---|---|---|
| 2 | | 4-pyridyl | |
| 3 | | phenyl | |
| 4 | 2-(piperidin-1-yl)ethyl | 4-pyridyl | |
| 5 | | phenyl | |
| 6 | isobutyl | quinolin-4-yl | 6,100 |
| 7 | | isoquinolin-5-yl | |
| 8 | | 4-pyridyl | |
| 9 | | quinolin-5-yl | |

-continued
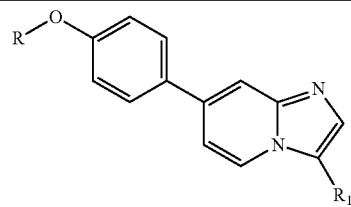
| Example | R | R₁ | BMP4 Cell IC₅₀ (nM) |
|---|---|---|---|
| 10 | | 8-quinolinyl | >10,000 |
| 11 | | 1-naphthyl | |
| 12 | | 7-quinoxalinyl | Inactive |
| 13 | | 3-quinolinyl | inactive |
| 14 | | 6-isoquinolinyl | Inactive |
| 15 | | 7-isoquinolinyl | Negative |
| 16 | | 4-isoquinolinyl | Inactive |

-continued
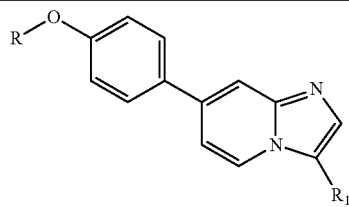
| Example | R | R₁ | BMP4 Cell IC$_{50}$ (nM) |
|---|---|---|---|
| 17 | isobutyl* | 4-hydroxyphenyl* | Inactive |
| 18 | | 4-(dimethylamino)phenyl* | Negative |
| 19 | | quinolin-6-yl* | Negative |
| 20 | | 2-chloropyridin-4-yl* | 970 |
| 21 | | 2-fluoropyridin-4-yl* | 1,250 |
| 22 | | 7-chloroquinolin-4-yl* | >10,000 |
| 23 | | 2'-methyl-[2,4'-bipyridin]-4-yl* | Negative |

-continued
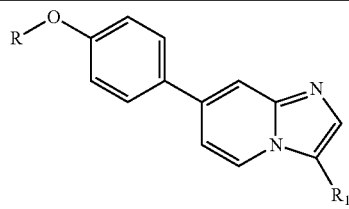
| Example | R | R₁ | BMP4 Cell IC₅₀ (nM) |
|---|---|---|---|
| 24 | | pyrimidin-5-yl | Potentiates @ 1-10 uM |
| 25 | | phenyl | Potentiates @ 1-10 uM |
| 26 | | 1,5-dimethyl-1H-pyrazol-4-yl | Potentiates @ 0.5-10 uM |
| 27 | | 3,5-dimethyl-1H-pyrazol-4-yl | Negative |
| 28 | | 1H-pyrazol-4-yl | 730 |
| 29 | | 1-(4-fluorophenyl)-1H-pyrazol-4-yl | inactive |
| 30 | | 3-methyl-1H-pyrazol-4-yl | >10,000 |
| 31 | | 2-methylpyridin-4-yl | 670 |

-continued
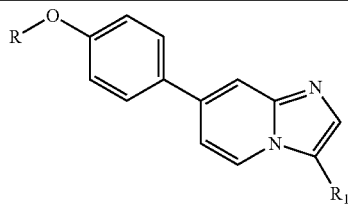
| Example | R | R₁ | BMP4 Cell IC$_{50}$ (nM) |
|---|---|---|---|
| 32 | | 3-bromo-2-fluoropyridin-4-yl | Negative |
| 33 | | thiazol-5-yl | >10,000 |
| 34 | | thiophen-3-yl | Potentiates @ 0.1-10 uM |
| 35 | | 3-methylpyridin-4-yl | Potentiates @ 1 uM but decrease @ 10 uM |
| 36 | | thiophen-2-yl | Potentiates @ 0.1-10 uM |
| 37 | CF₃ | phenyl | Potentiates @ 1-10 uM |
| 38 | n-propyl | phenyl | Potentiates @ 0.5-10 uM |
| 39 | methyl | phenyl | Potentiates @ 0.1-10 uM |
| 40 | phenyl | phenyl | Negative |

-continued
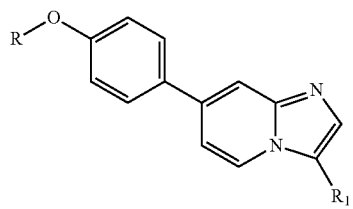
| Example | R | R₁ | BMP4 Cell IC$_{50}$ (nM) |
|---|---|---|---|
| 41 | 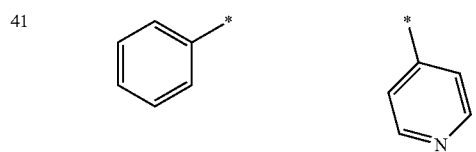 | | |
| 42 | 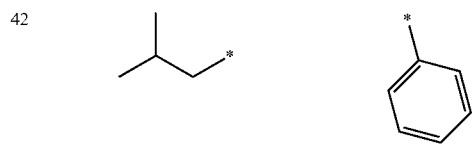 | | |
| 43 | 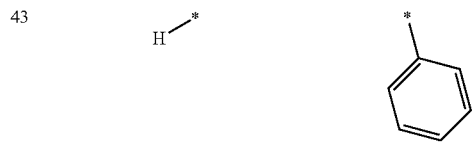 | | |
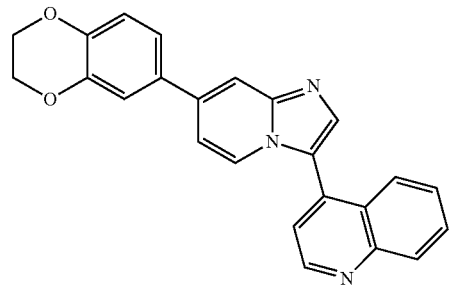 [SMILES: c1ccc2c(-c3cnc4cc(-c5ccc6c(c5)OCCO6)ccn34)ccnc2c1]
2890
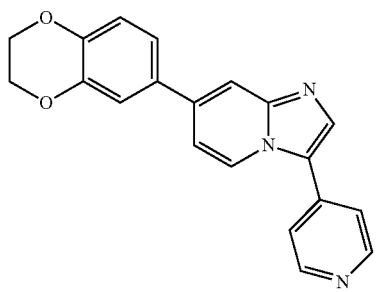 [SMILES: c1cc(-c2cnc3cc(-c4ccc5c(c4)OCCO5)ccn23)ccn1]

-continued
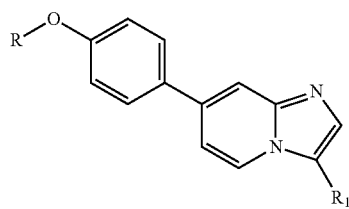
| Example | R | R₁ | BMP4 Cell IC₅₀ (nM) |
|---|---|---|---|
| | | | |
| | | | Actually induces/ potentiates at 0.5-10 uM (5-25-2012) |
| | | | Actually induces/ potentiates BMP reproter (5-31-2012, set 9) |
| | | | 8100 |

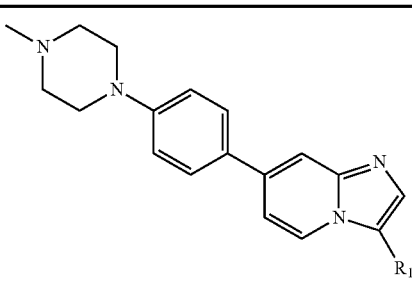
| Example | R₁ | BMP4 Cell IC$_{50}$ (nM) |
|---|---|---|
| 44 | 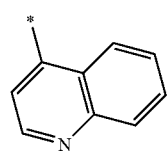 | <10 |
| 45 | 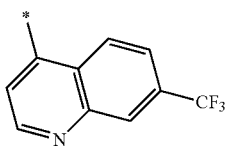 | >10,000 (TFA) |
| 46 | 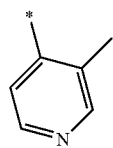 | 5,000 (TFA) |
| 47 | 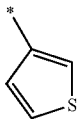 | 5,000 (TFA) |
| 48 | 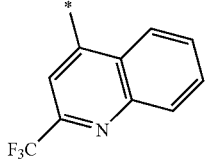 | inhibits at 10 uM |
| 49 | 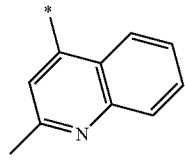 | 4.5 |
| 50 | 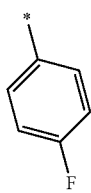 | Inhibits at 10 uM |
-continued
| Example | R₁ | BMP4 Cell IC$_{50}$ (nM) |
|---|---|---|
| 51 | 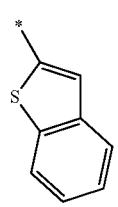 | No inhibition to 10 μM |
| 52 | 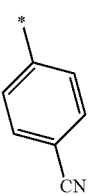 | PARTIAL INHIBITION |
| 53 | 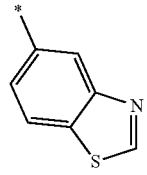 | Inhibits at 10 uM |
| 54 |  | 59 |
| 55 | 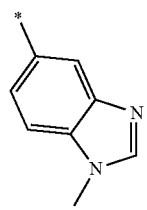 | No inhibition to 10 uM |
| 56 | 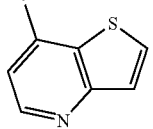 | 11.6 |

139
-continued

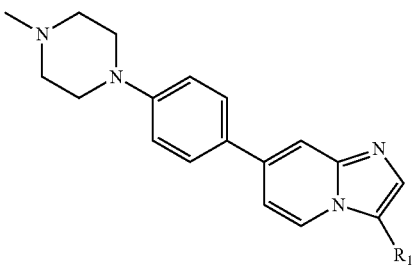

| Example | R₁ | BMP4 Cell IC₅₀ (nM) |
|---|---|---|
| 57 | 3-fluoro-5-cyanophenyl | 10,000 |
| 58 | benzothiadiazolyl | No inhibition to 10 uM. |
| 59 | phenyl | Induces at 0.1-1 uM. Partially inhibits @ 5 uM. KILLS at 10 uM |
| 60 | 4-pyridyl | 100 |
| 61 | 2-methyl-4-pyridyl | 40 |
| 62 | 2-chloro-4-pyridyl | 58 |
| 63 | 3-pyridyl | Inhibits at 10 uM, but not at 5 uM |

140
-continued

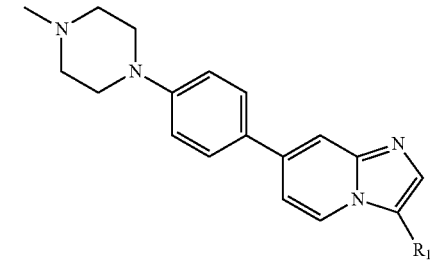

| Example | R₁ | BMP4 Cell IC₅₀ (nM) |
|---|---|---|
| 64 | 8-fluoroquinolin-4-yl | <10 (TFA) |
| 65 | 8-trifluoromethylquinolin-4-yl | Potent: Inhibits 50% @ 5 uM, fully @ 10 uM |
| 66 | pyrazolo[1,5-a]pyrimidinyl | Active at 10 uM |
| 67 | benzofuran-3-yl | Weakly Potent: Inhibits @ 5 uM, fully @ 10 uM (#26, 10-24-2012) |
| 69 | furo[3,2-b]pyridin-3-yl | Weakly Potent: Inhibits @ 5 uM, fully @ 10 uM (#26, 10-24-2012) |
| 69 | benzothiophen-3-yl | 1280 (TFA) |
| 70 | 1,5-naphthyridin-4-yl | <10 |

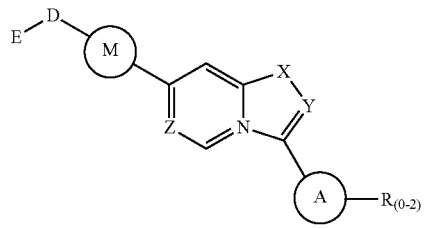

(I)

wherein:
X, Y, and Z are independently N or CH;
A is substituted or unsubstituted and selected from cycloalkyl, heterocycloalkyl, aryl or heteroaryl;
R is selected from H, $CF_3$, halogen, CN, alkyl, aryl, heteroaryl, or $NR_1R_2$;
M is substituted or unsubstituted and is selected from aryl or heteroaryl;
D is selected from a bond, O, $CR_1R_2$, NH, $NR_1$ or $NR_1R_2$;
E is absent or selected from H, $CF_3$, halogen, CN, alkyl, aryl, heteroaryl, $C_3$-$C_{12}$ cycloalkyl, $C_3$-$C_{12}$ cycloheteroalkyl, —$(CH_2)_x$—$C_3$-$C_{12}$ cycloalkyl, or —$(CH_2)_x$—$C_3$-$C_{12}$ cycloheteroalkyl;
$R_1$ is absent or selected from H, alkyl, aryl, or heteroaryl;
$R_2$ is selected from H, alkyl, aryl, heteroaryl, $COR_1$, or, $R_1$ and $R_2$ can form a $C_3$-$C_{12}$ cycloalkyl or $C_3$-$C_{12}$ cycloheteroalkyl containing O, N or S; and
x is an integer from 2 to 500; or
a pharmaceutically acceptable salt thereof

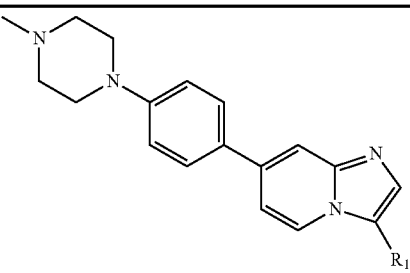

| Example | $R_1$ | BMP4 Cell $IC_{50}$ (nM) |
|---|---|---|
| 71 | (quinoline with F) | 16.6 |
| 72 | (quinoline) | inhibition at 10 uM |

| | BMP Type 1 receptor (nM) | | | | | |
|---|---|---|---|---|---|---|
| Entry | ALK2/ACVR1 | ALK1/ACVR1 | ALK3/BMPRR1A | ALK4/ACVR1B | ALK5/TGFBR1 | ALK6/BMPR1B |
| 1 | 53.1 | 49.6 | 52 | 31,000 | 23,000 | 151.2 |
| 5 | 270.0 | | | | | |
| 21 | 24.0 | 6.4 | 7.9 | ND | 3960 | 11 |
| 25 | 155.0 | 87 | 118 | ND | 13,600 | 340 |
| 26 | 265.0 | | | | >100,000 | |
| 30 | 645.1 | | | | >100,000 | |
| 42 | 1970.0 | 494 | 92 | ND | >100,000 | 895 |
| 45 | 149.0 | | | | 3490 | |
| 51 | 26.5 | | | | | |
| 60 | 1.3 | | 40.1 | | | |
| 62 | 14.4 | | 50.8 | | | |
| 66 | 46.0 | | | | | |
| 67 | 20.0 | | | | | |
| 68 | 33.2 | | 40.6 | | | |

The invention now being generally described, it will be more readily understood by reference to the following examples which are included merely for purposes of illustration of certain aspects and embodiments of the present invention, and are not intended to limit the invention.

We claim:

1. A method of treating a disease state associated with modulating the BMP signaling pathway in a subject, comprising administering to a subject suffering from the disease state at least one compound having a structure represented by the following formula (I):

and wherein the disease state is selected from anemia, iron deficiency anemia or anemia of chronic disease, fibrodysplasia ossificans progressiva (FOP), breast cancer, prostate cancer, bone cancer, lung cancer, renal cancer, inflammatory bowel disease, pathological bone function, ectopic bone formation, maladaptive bone formation, hypertension, ventricular hypertrophy, atherosclerosis, acute megakaryoblastic leukemia, heart disease, myocardial ischemic injury, vascular calcification, aortic valve calcification, ventricular hypertrophy, liver damage, liver disease, Duchenne muscular dystrophy, hereditary spastic paraplegias, retinopathy of prematurity, diabetic retinopathy, wet macular degeneration, diabetic nephropathy, or renal fibrosis.

2. The method of claim 1, wherein X, Y and Z together help form:

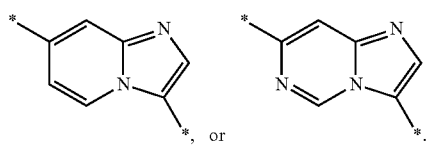, or

3. The method of claim 1, wherein X, Y and Z together help form:

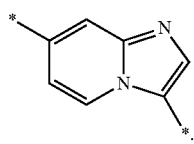

4. The method of claim 1, wherein

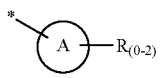

is:

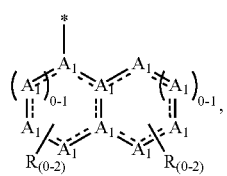

wherein $A_1$ is independently O, S, $CR_1R_2$ or $NR_1$.

5. The method of claim 1, wherein M is optionally substituted with one or more R, and is selected from $C_3$-$C_{12}$ cycloalkyl, $C_3$-$C_{12}$ cycloalkenyl, aryl, heteroaryl, $C_3$-$C_{12}$ heterocycloalkyl, or $C_3$-$C_{12}$ heterocycloalkenyl.

6. The method of claim 1, wherein M is optionally substituted phenyl or pyridine.

7. The method of claim 1, wherein M, D, and E together form:

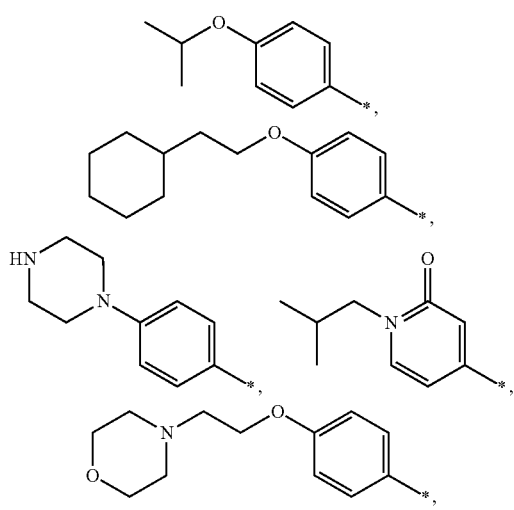

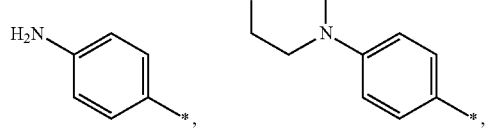
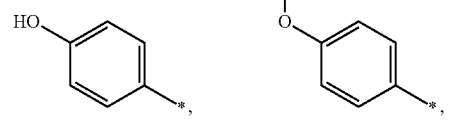
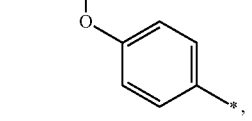
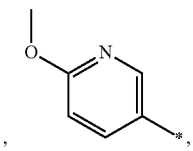
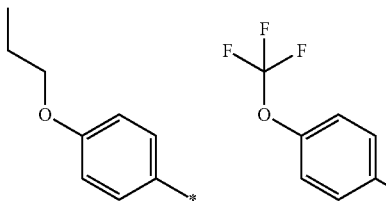
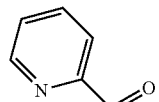
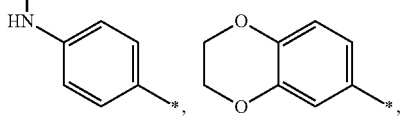
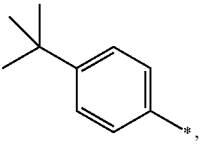
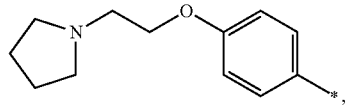
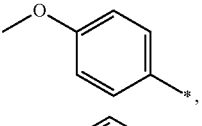
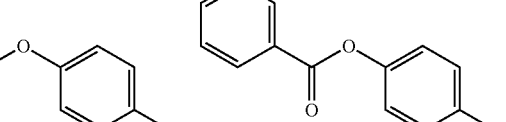
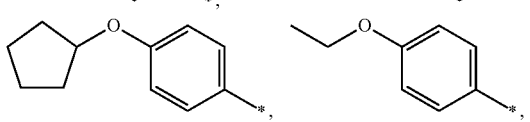

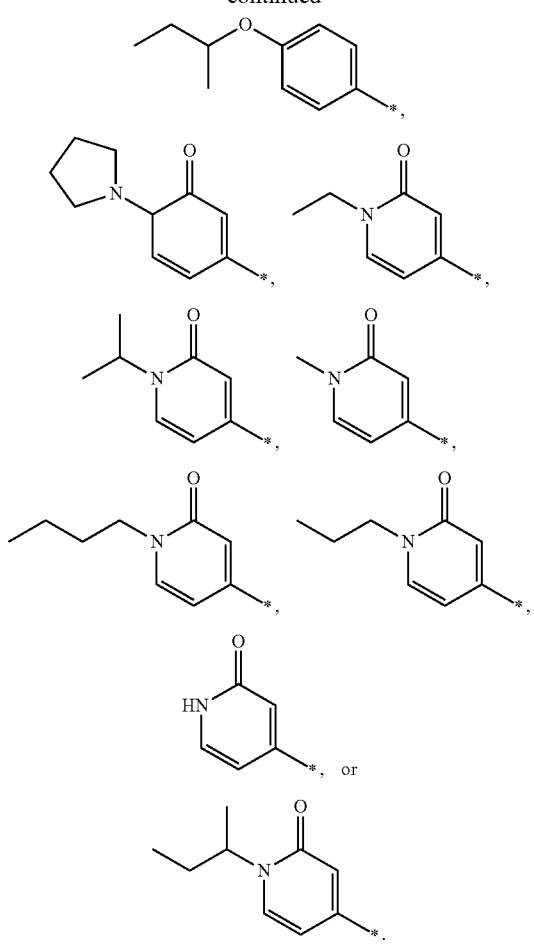
8. The method of claim 1, wherein A is chosen from the following:
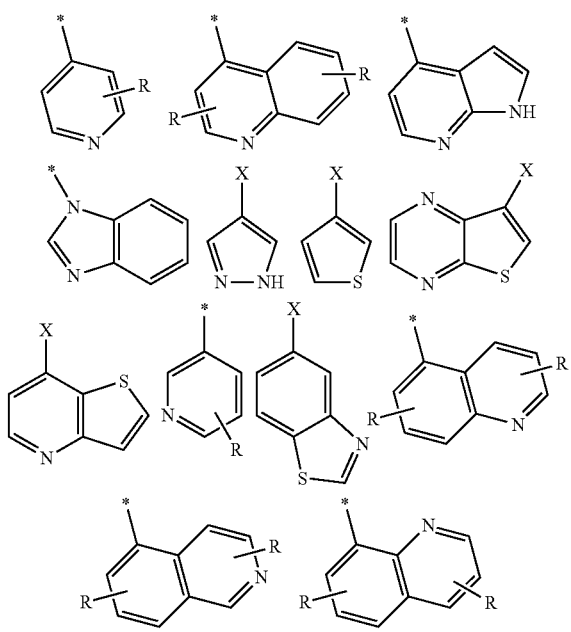
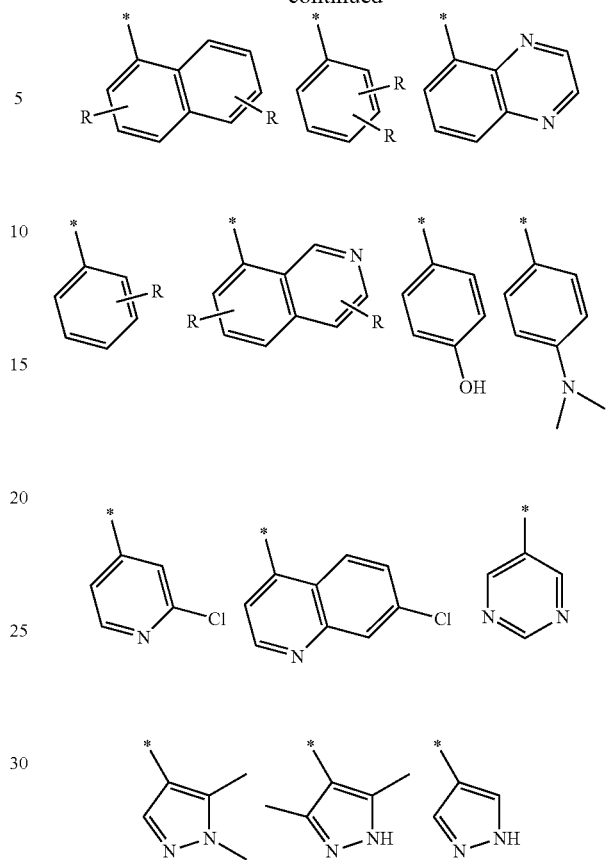
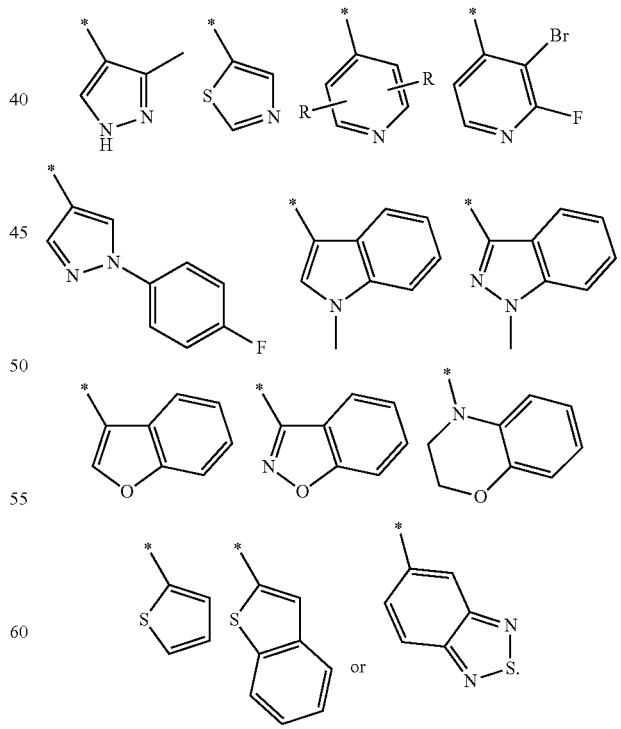
9. The method of claim 1, wherein the compound of formula I has the structure:

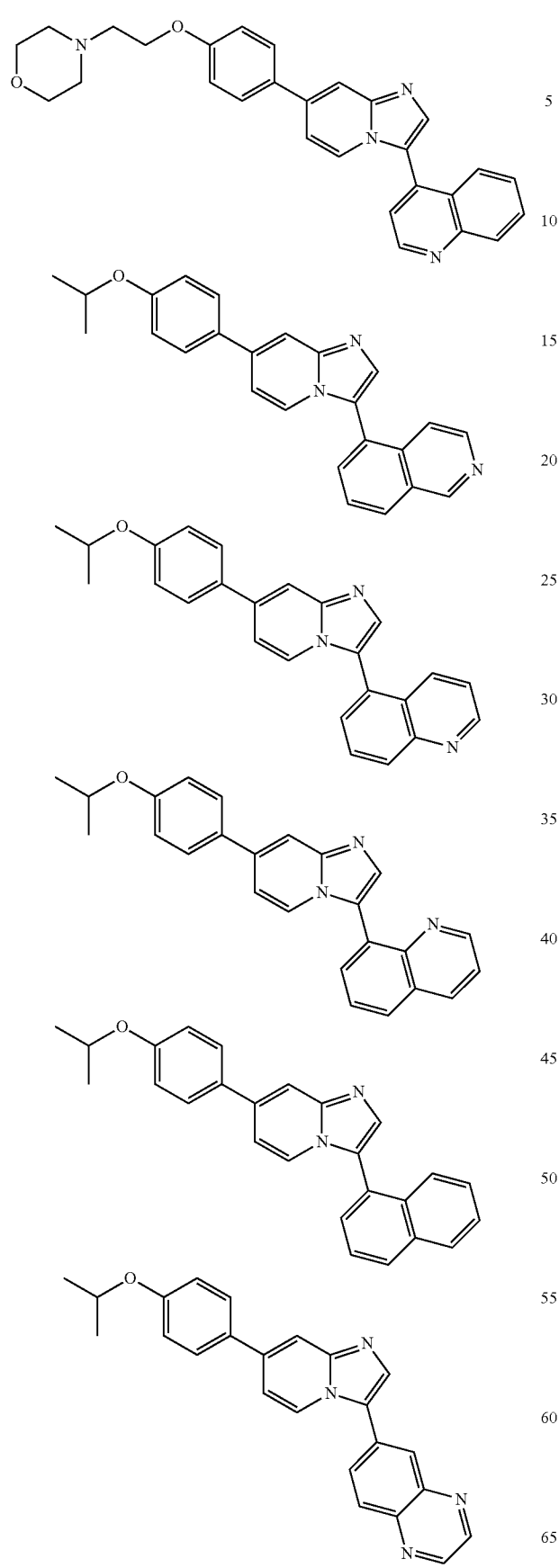
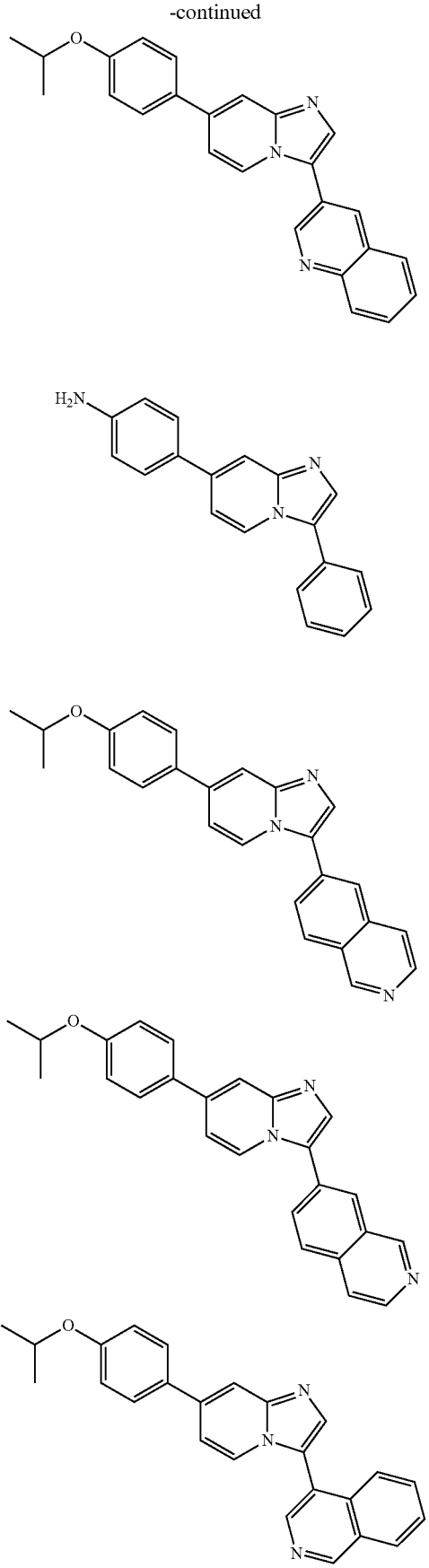

149
-continued
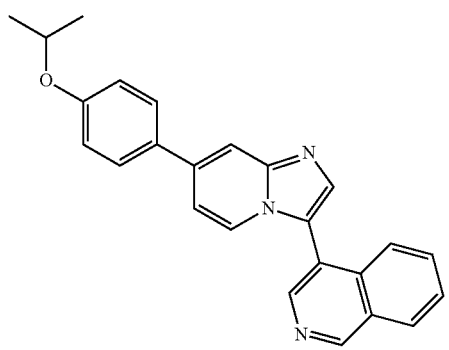
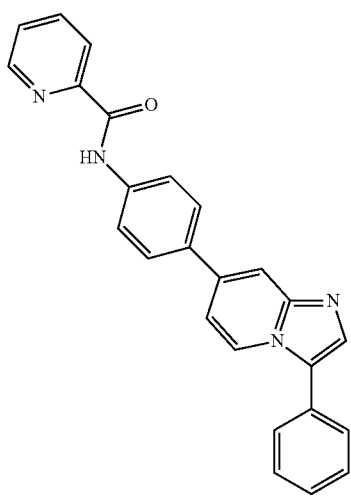
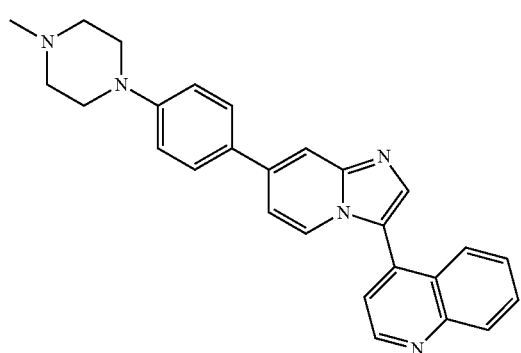 [SMILES: CN1CCN(c2ccc(-c3ccn4c(-c5ccnc6ccccc56)cnc4c3)cc2)CC1]
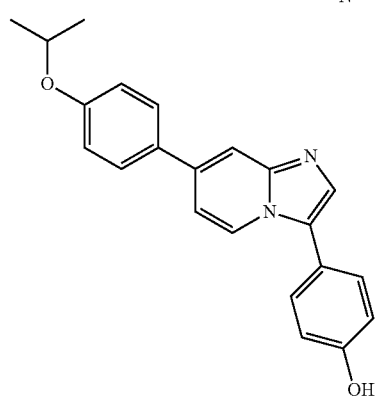
150
-continued
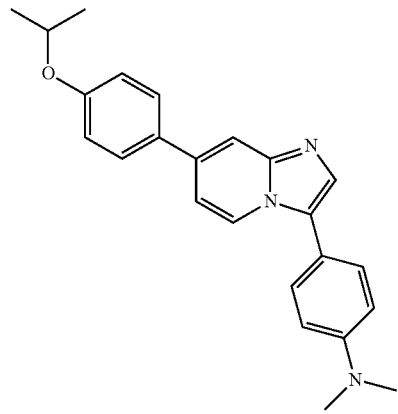
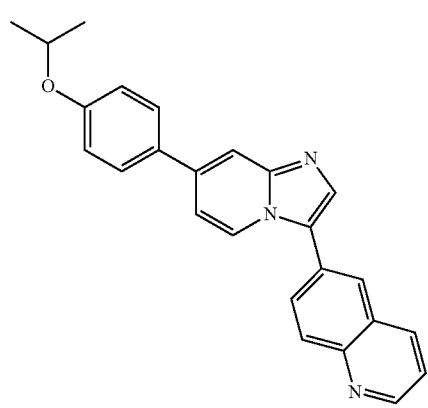
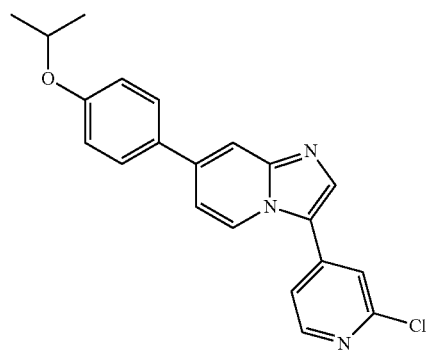
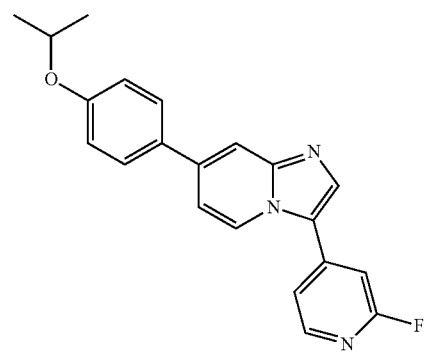

151
-continued
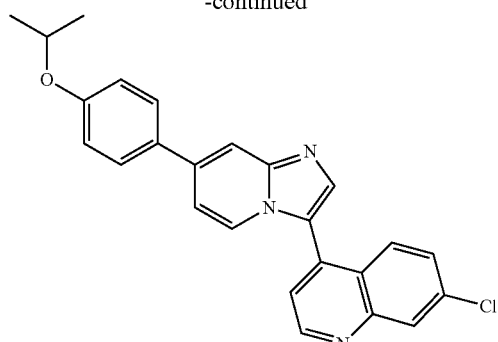
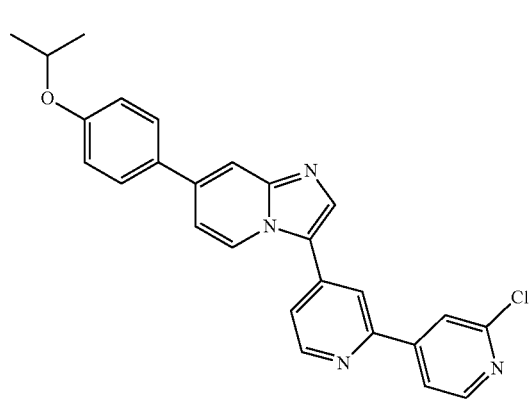
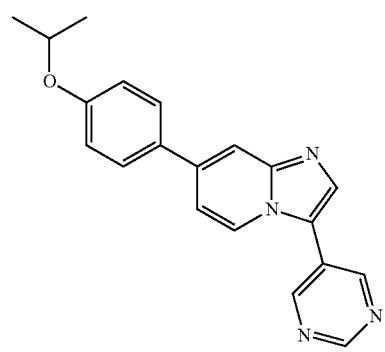
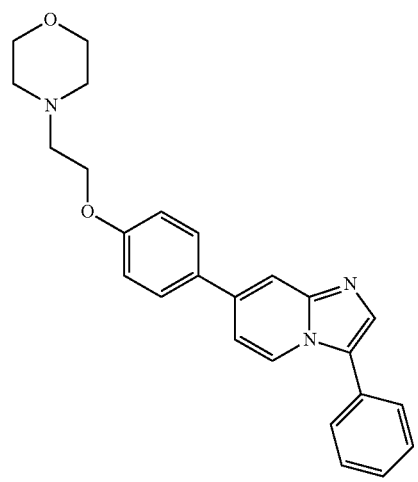
152
-continued
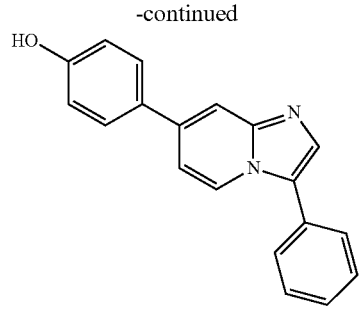
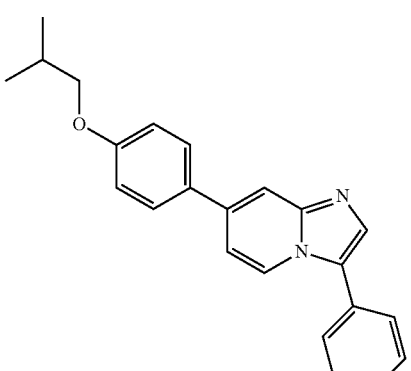
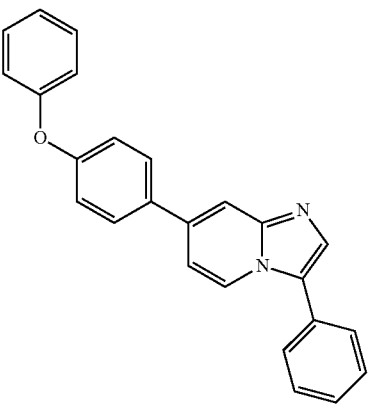
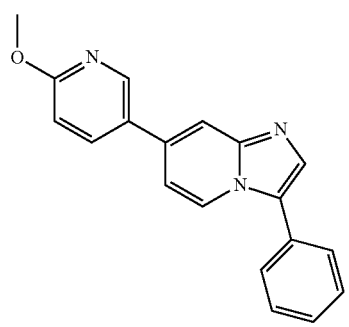

153
-continued
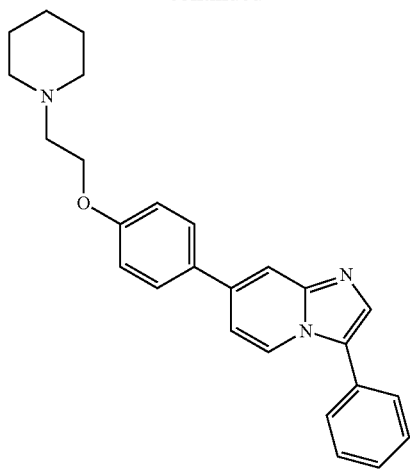
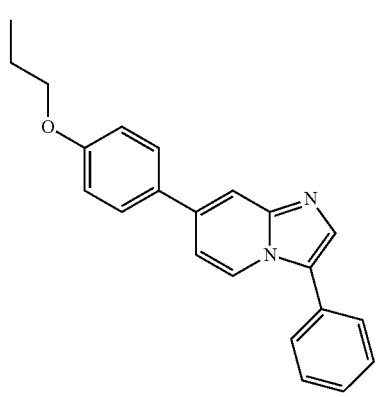
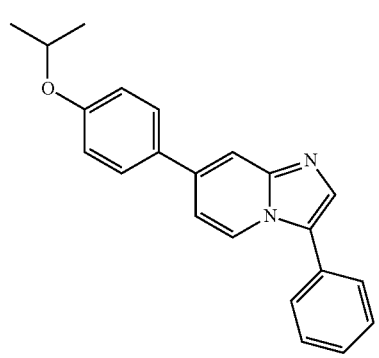
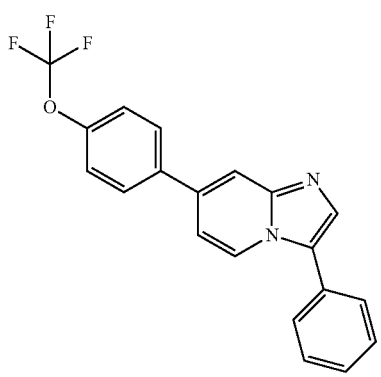
154
-continued
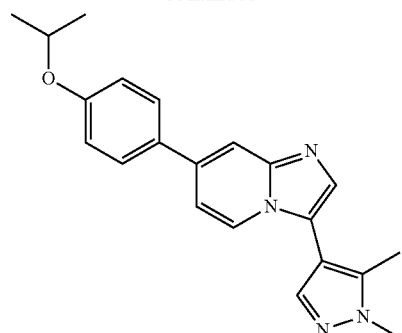
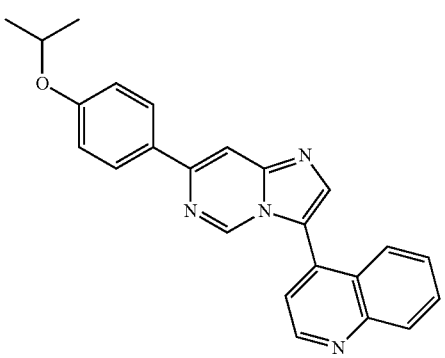
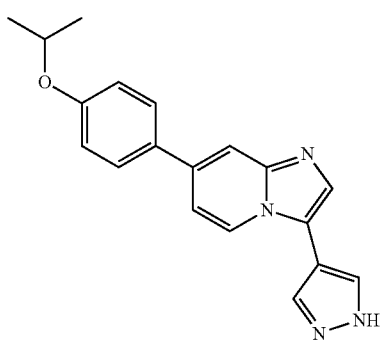

155
-continued
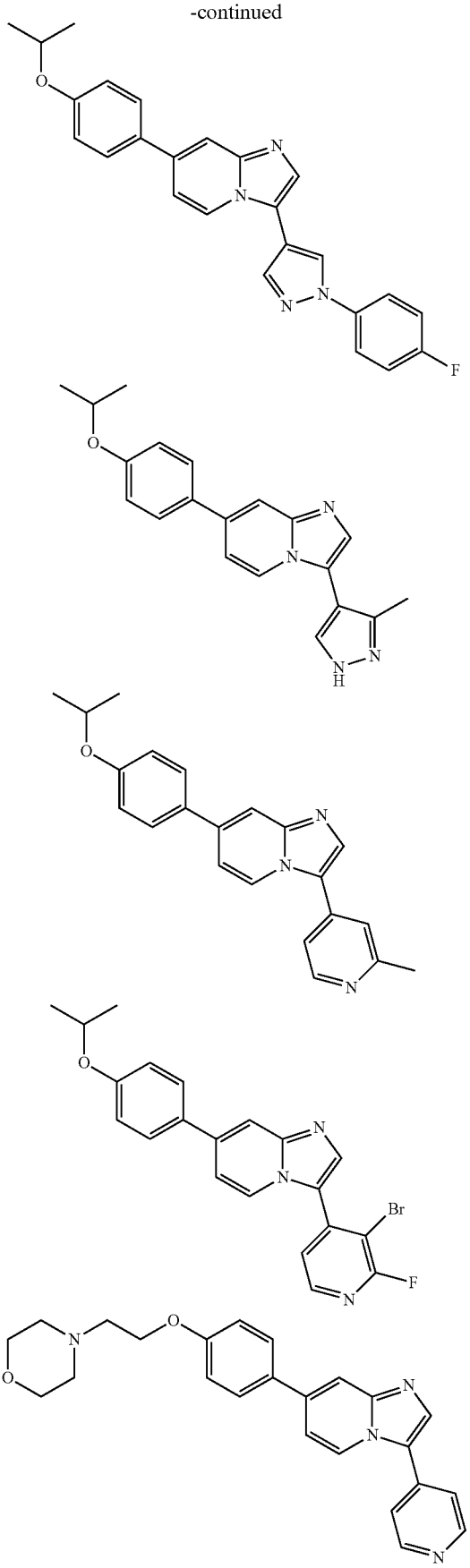
156
-continued
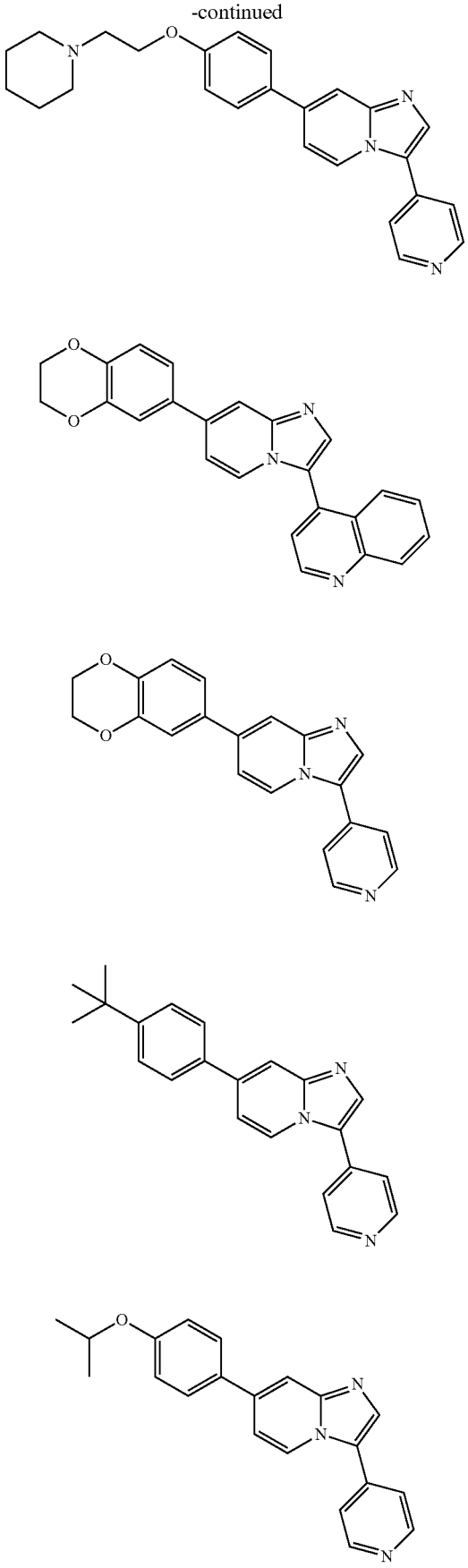

157
-continued
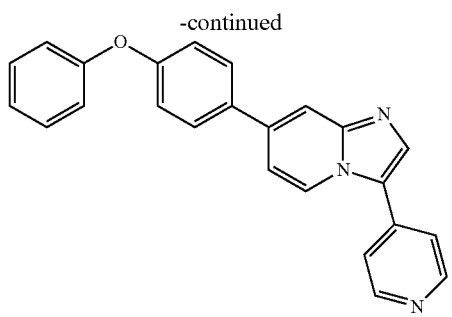
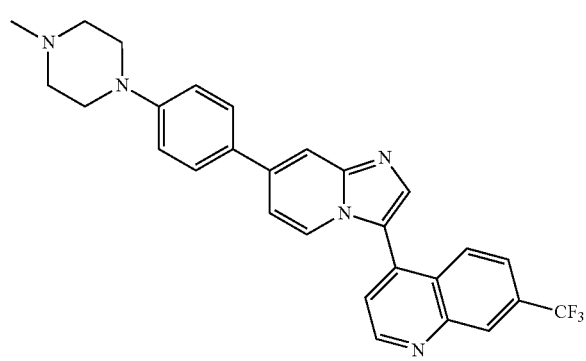
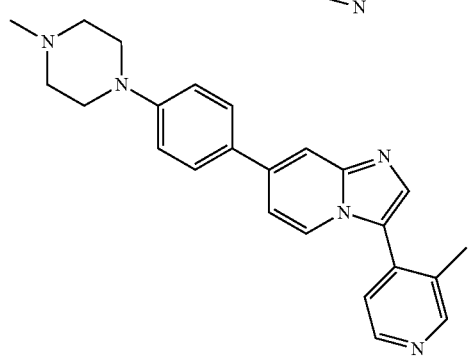
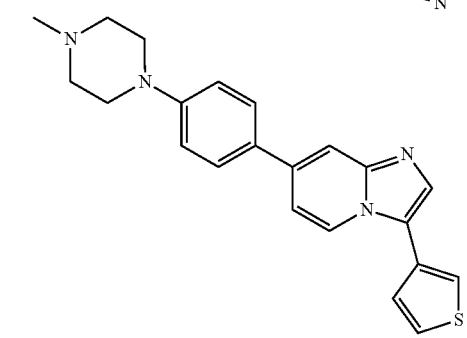
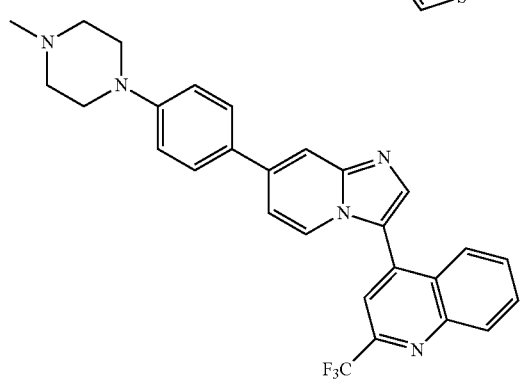
158
-continued
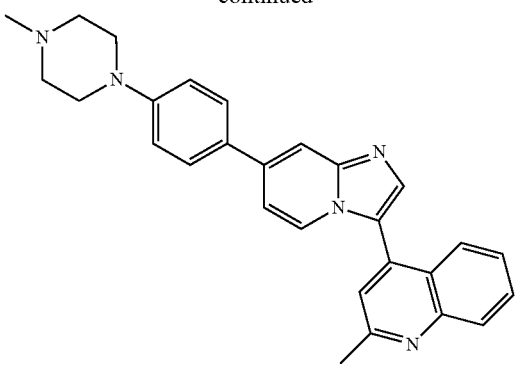
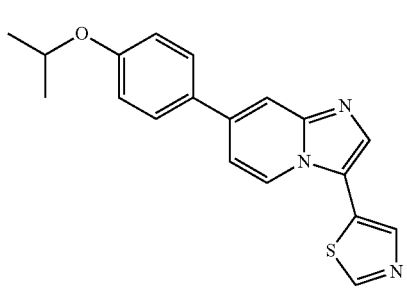
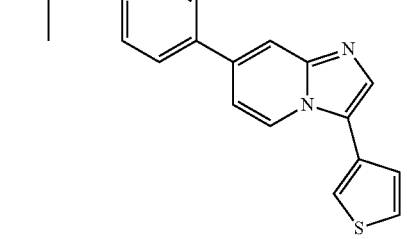
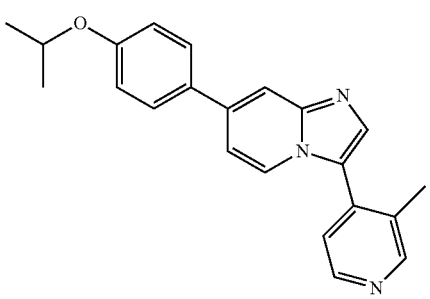
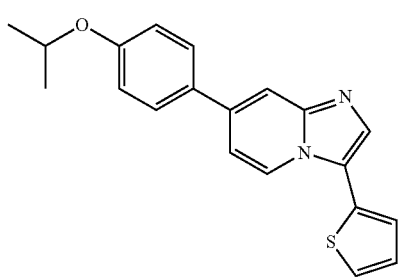

159
-continued
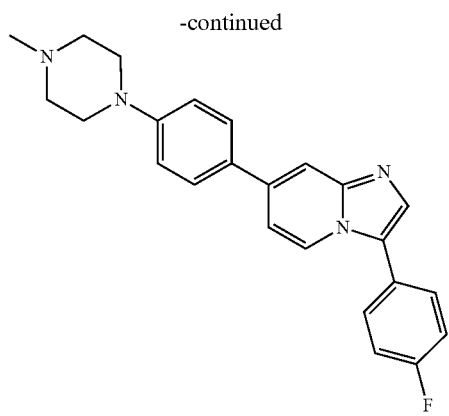
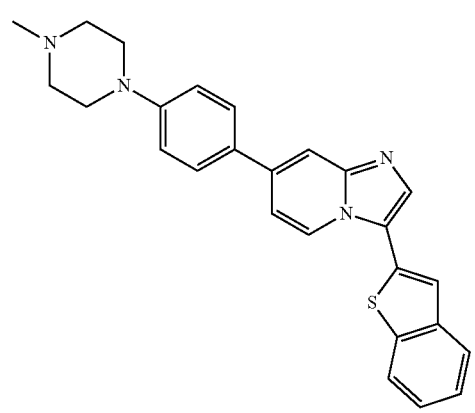
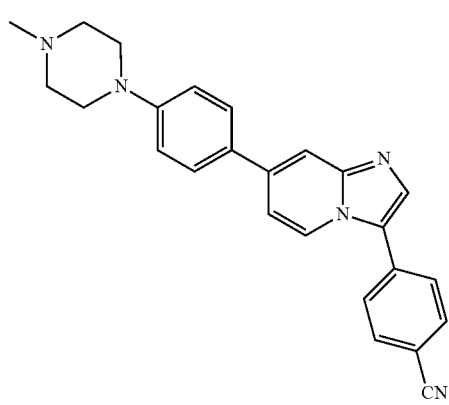
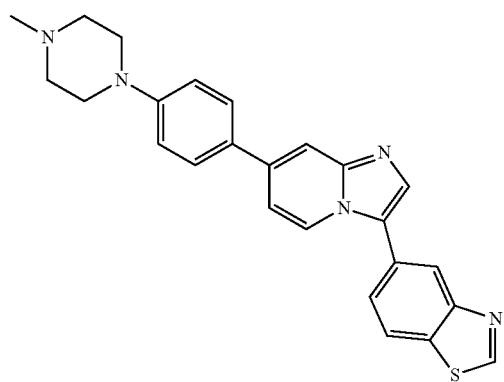
160
-continued
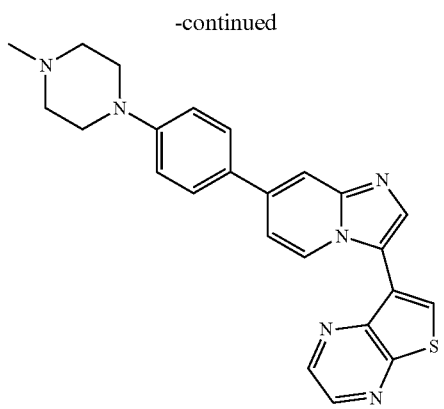
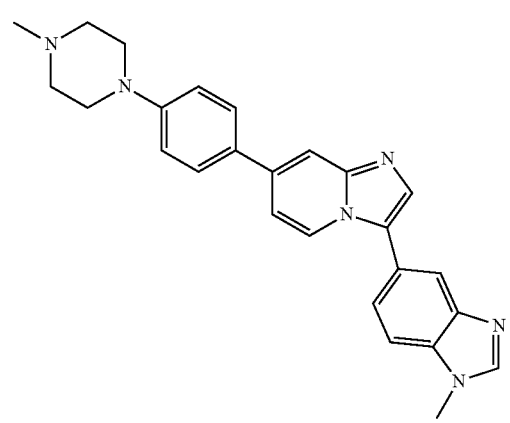
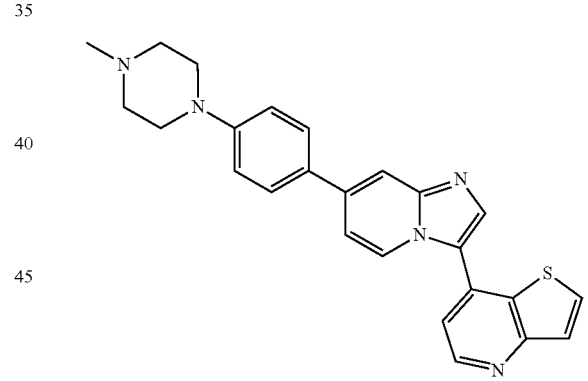
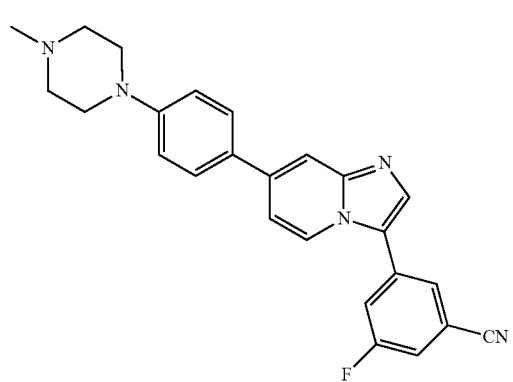

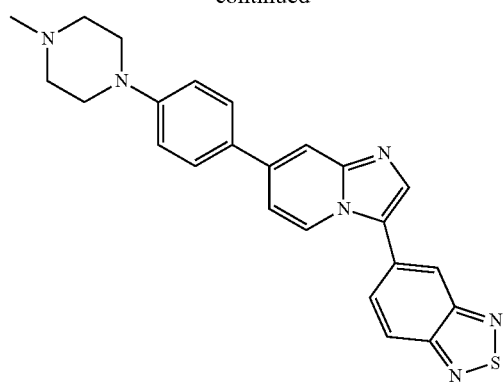
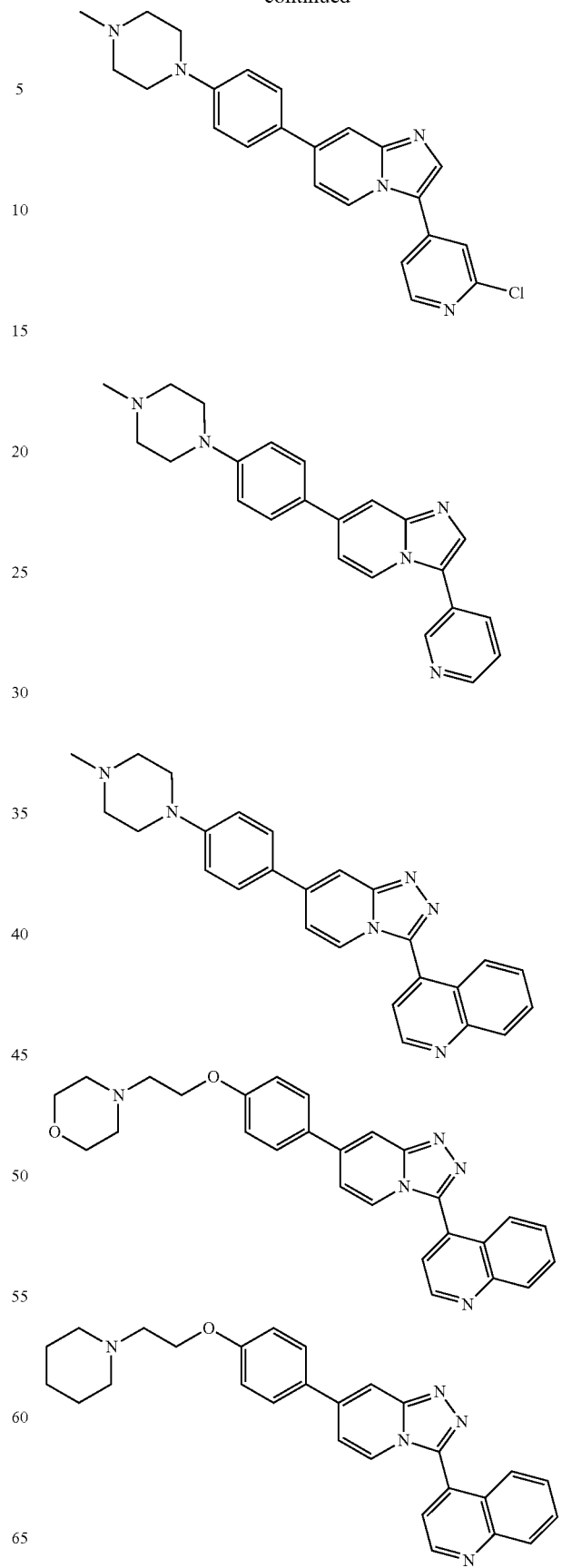

163
-continued
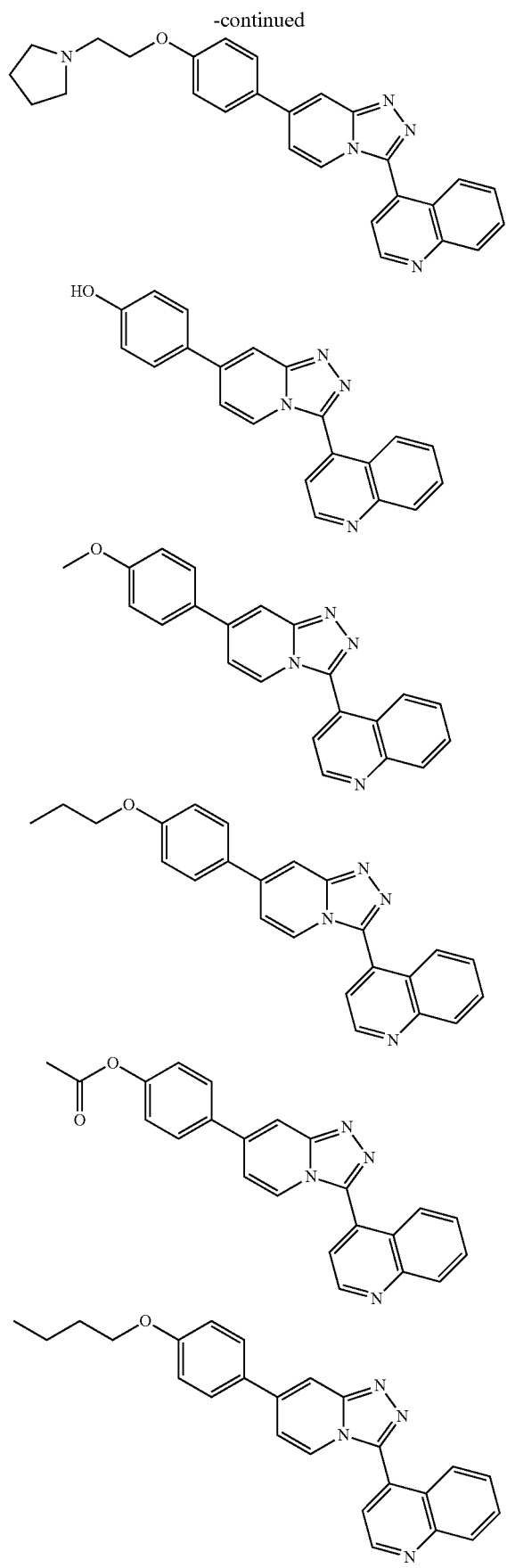
164
-continued
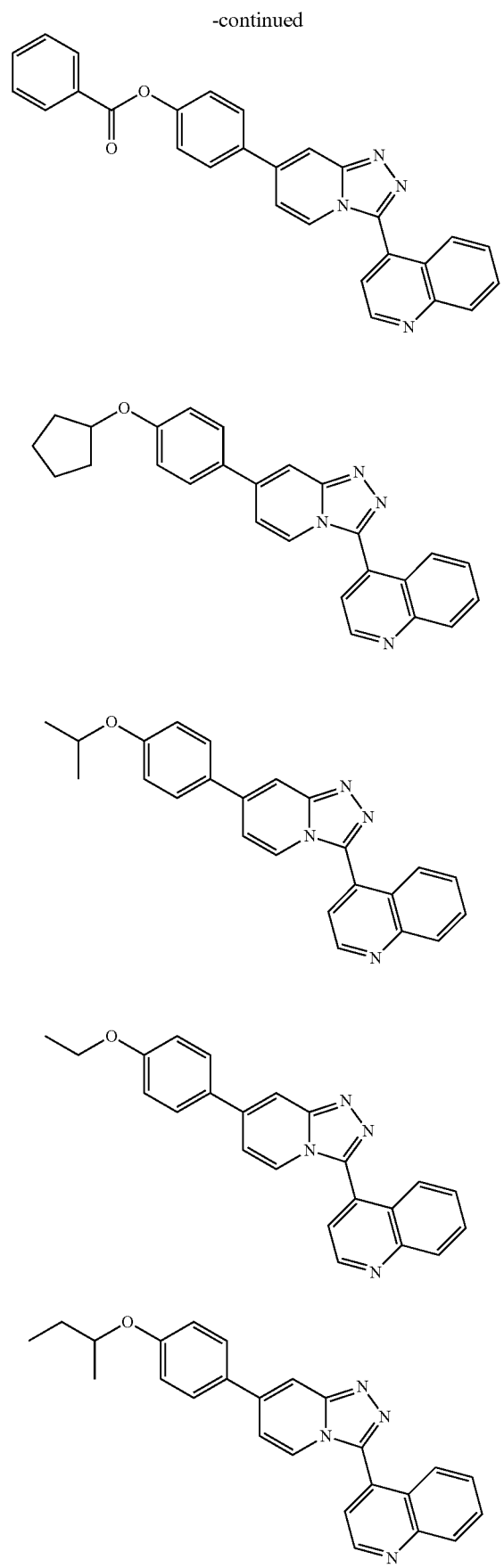

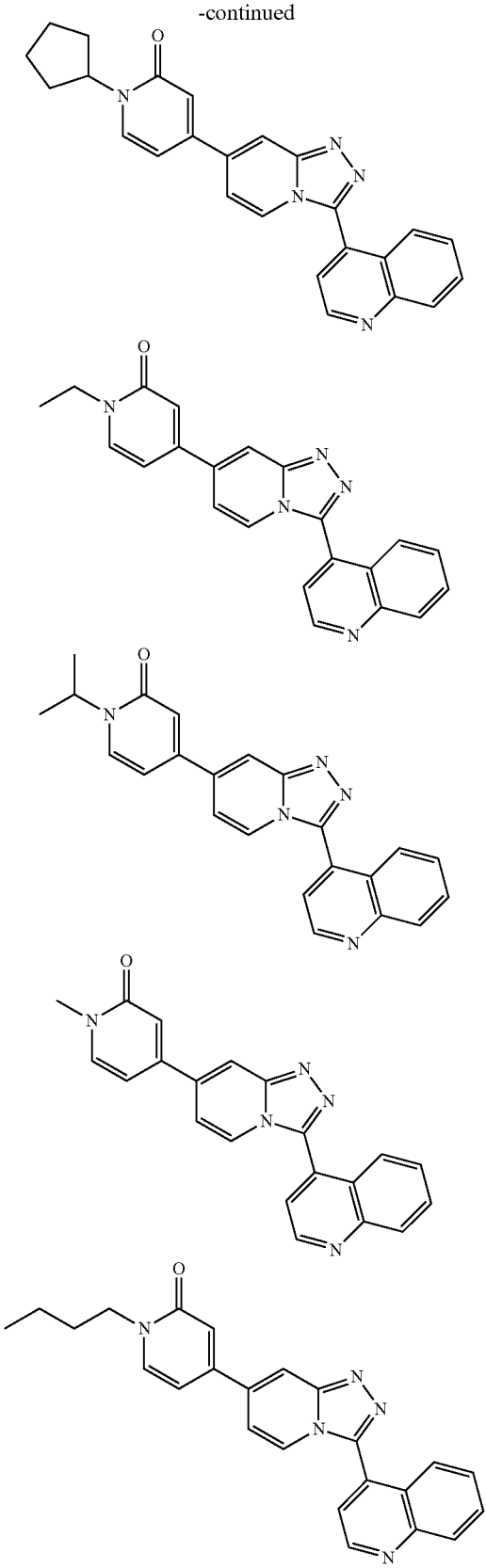

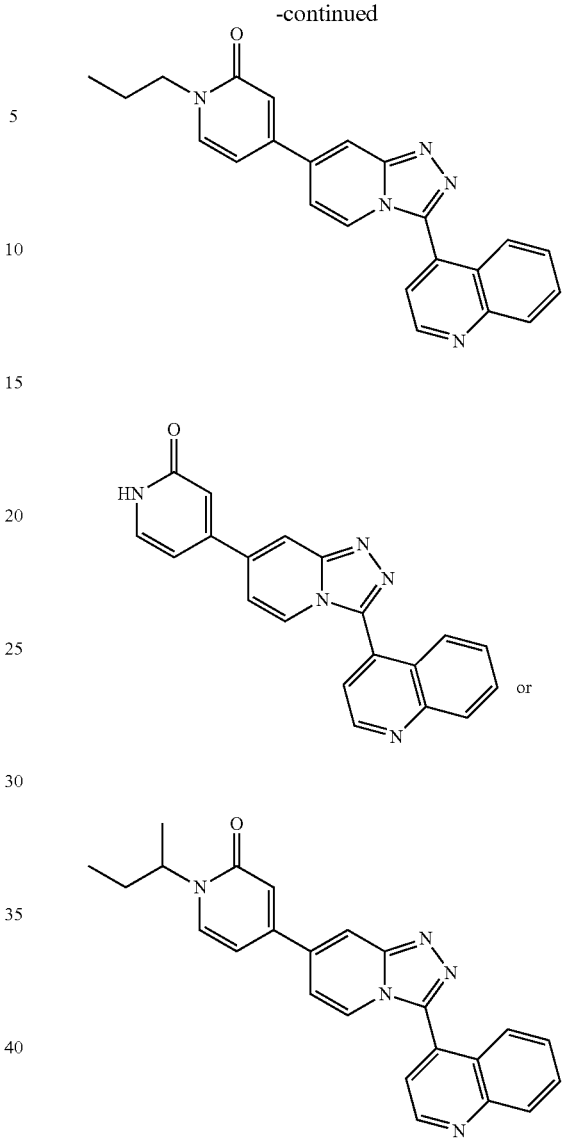

or a pharmaceutically acceptable salt thereof.

10. The method of claim 1, wherein the disease state is anemia.

11. The method of claim 10, wherein the anemia is iron deficiency anemia or anemia of chronic disease.

12. The method of claim 1, wherein the disease state is fibrodysplasia ossificans progressiva (FOP).

13. The method of claim 1, wherein the disease state is breast cancer, prostate cancer, bone cancer, lung cancer, or renal cell cancer.

14. The method of claim 1, wherein the disease state is pathologic bone function, ectopic bone formation or maladaptive bone formation.

15. The method of claim 1, wherein the disease state is acute megakaryoblastic leukemia.

* * * * *

UNITED STATES PATENT AND TRADEMARK OFFICE
CERTIFICATE OF CORRECTION

PATENT NO. : 10,196,392 B2
APPLICATION NO. : 15/652100
DATED : February 5, 2019
INVENTOR(S) : Hopkins et al.

Page 1 of 1

It is certified that error appears in the above-identified patent and that said Letters Patent is hereby corrected as shown below:

In the Specification

Insert as the first paragraph, the following:
-- Government Support
This invention was made with government support under grant numbers HL104040, HL100398, and GM118557 awarded by the National Institutes of Health. The government has certain rights in the invention. --

Signed and Sealed this
Tenth Day of December, 2019

Andrei Iancu
*Director of the United States Patent and Trademark Office*